US006537764B1

(12) United States Patent
Gerard et al.

(10) Patent No.: US 6,537,764 B1
(45) **Date of Patent: *Mar. 25, 2003**

(54) METHOD OF IDENTIFYING INHIBITORS OF C—C CHEMOKINE RECEPTOR 3

(75) Inventors: Craig J. Gerard; Norma P. Gerard, both of Dover; Charles R. Mackay, Watertown; Paul D. Ponath, Boston; Theodore W. Post, Newton; Shixin Qin, Lexington, all of MA (US)

(73) Assignees: Children's Medical Center Corporation, Boston, MA (US); Millennium Pharmaceuticals, Inc., Cambridge, MA (US); Brigham & Women's Hospital, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/720,565

(22) Filed: Sep. 30, 1996

Related U.S. Application Data

(63) Continuation-in-part of application No. PCT/US96/00608, filed on Jan. 19, 1996, which is a continuation-in-part of application No. 08/375,199, filed on Jan. 19, 1995.

(51) Int. Cl.[7] ....................... G01N 33/53; G01N 33/566

(52) U.S. Cl. ......................... 435/7.21; 435/7.1; 435/7.2

(58) Field of Search ............................... 536/23.4, 23.5; 435/69.1, 69.7, 325, 320.1, 7.2, 7.1, 7.21; 530/300, 350; 436/501, 536

(56) References Cited

U.S. PATENT DOCUMENTS

| | | | | |
|---|---|---|---|---|
| 5,225,538 | A | | 7/1993 | Capon et al. |
| 5,284,746 | A | * | 2/1994 | Sledziewski et al. |
| 5,470,571 | A | * | 11/1995 | Herlyn et al. |
| 5,652,133 | A | | 7/1997 | Murphy |

FOREIGN PATENT DOCUMENTS

| | | | | |
|---|---|---|---|---|
| DE | 43 32 256 | C1 | * | 9/1993 |
| EP | 0 475 746 | A1 | * | 3/1992 |
| EP | 0 578 962 | A2 | * | 1/1994 |
| WO | WO 92/01810 | | * | 2/1992 |
| WO | WO 94/05695 | | * | 3/1994 |
| WO | WO 94/11504 | | * | 5/1994 |
| WO | WO 94/12635 | | * | 9/1994 |
| WO | WO 94/20142 | | * | 9/1994 |
| WO | WO 94/28931 | | * | 12/1994 |
| WO | WO 95/08576 | | * | 3/1995 |
| WO | WO 95/31467 | | * | 11/1995 |
| WO | WO 96/22371 | | | 7/1996 |
| WO | WO 97/21812 | | | 6/1997 |
| WO | WO 97/22698 | | | 6/1997 |

OTHER PUBLICATIONS

Neote, et al. Cell, vol. 72, pp 415–425, Feb. 1993.*
Chaudhuri, et al. J. Biol. Chem., vol. 269, pp 7835–7838, 1994.*
Henderson et al. TiPS, vol. 13, pp 145–152, 1992.*
Navia, et al. Immunolo. Today, vol. 14, pp 295–301, Jun. 1993.*
GenEmbl Acc No. L09230, 1993.*
Ngo et al. The Protein Folding Problem and Tertiary Structure Prediction, Merz & LeGrand, Birkhauser Boston, pp. 491–495, 1994.*
Chaudhuri, A. et al. J. Biol. Chem. 269 (11): 7835–7838, Mar. 1994.
Debets, R. et al. Immunology Today 15 (10): 455–458, Oct. 1994.
Henderson, B. et al. TiPS 13: 145–152, Apr. 1992.
Navia, M. et al. Immunology Today 14 (6) 295, Jun. 1993.
Yamagami, S., et al., "cDNA Cloning and Functional Expression of a Human Monocyte Chemoattractant Protein 1 Receptor," *Biochemical Biophysical Research Communications,* 202(2):1156–1162 (1994).
Springer, Timothy A., "Traffic Signals for Lymphocyte Recirculation and Leukocyte Emigration: The Multistep Paradigm", *Cell,* 76:301–314, (1994).
Murphy, Philip M., "The Molecular Biology of Leukocyte Chemoattractant Receptors", *Annu. Rev. Immunol.,* 12:593–633 (1994).
Baggiolini M., and Dahinden Clemens A., "CC chemokines in allergic inflammation", *Immunology Today,* 15(3):127–133, (1994).
Gerard N.P., and Gerard, C., "The chemotactic receptor for human C5a anaphylatoxin", *Nature,* 349:614–617, (1991).
Neote, K., et al., "Molecular Cloning, Functional Expression, and Signaling Characteristics of a C–C Chemokine Receptor", *Cell,* 72:415–425, (1993).
Gao, J–L., et al., "Structure and Functional Expression of the Human Macrophage Inflammatory Protein 1α/RANTES Receptor", *J. of Exp. Med.,* 177:1421–1427, (1993).
Charo, I.F., et al., "Molecular cloning and functional expression of two monocyte chemoattractant protein 1 receptors reveals alternative splicing of the carboxyl–terminal tails", *Proc. Natl. Acad. Sci. USA,* 91:2752–2756 (1994).

(List continued on next page.)

*Primary Examiner*—Christina Chan
*Assistant Examiner*—Marianne DiBrino
(74) *Attorney, Agent, or Firm*—Hamilton, Brook, Smith & Reynolds, P.C.

(57) ABSTRACT

The present invention relates to a method of identifying an inhibitor of a mammalian (e.g., human) C—C chemokine receptor 3 (CCR3), comprising combining (a) a compound to be tested, (b) a host cell expressing a recombinant protein comprising a mammalian CCR3, and (c) a ligand of said receptor, under conditions suitable for binding of ligand to said receptor, and detecting or measuring the formation of a receptor-ligand complex. Inhibition of complex formation by the compound is indicative that the compound is an inhibitor.

83 Claims, 36 Drawing Sheets

OTHER PUBLICATIONS

Van Riper, G., et al., "Induction, Characterization, and Functional Coupling of the High Affinity Chemokine Receptor for RANTES and Macrophage Inflammatory Protein–1α upon Differentiation of an Eosinophilic HL–60 Cell Line", *J. of Immunol.,* 152:4055–4061 (1994).

Bischoff, S.C., et al., "RANTES and related chemokines activate human basophil granulocytes through different G protein–coupled receptors", *Eur. J. Immunol.,* 23:761–767, (1993).

Dahinden, C.A., et al., "Monocyte Chemotactic Protein 3 Is a Most Effective Basophil– and Eosinophil–activating Chemokine", *J. Exp. Med.,* 179:751–756 (1994).

Lefkowitz, R.J., "Turned on to ill effect", *Nature,* 365:603–604, (1993).

Clapham, D.E., "Mutations in G Protein–Linked Receptors: Novel Insights on Disease", *Cell,* 75:1237–1239, (1993).

Ponath, P.D., "C–C Chemokine Receptor 3: Identification of a Major Eosinophil Chemotactic Cytokine Receptor", In: Conference Schedule for conference entitled "On the Cutting Edge of Anti–Inflammatory Drug Discovery", (Jan., 1995).

Combadiere, C., et al., "Cloning and Functional Expression of a Human Eosinophil CC Chemokine Receptor", *J. of Biol. Chem.,* 270(27):16491–16494, (1995).

Combadiere, C., et al., Correction, "Cloning and functional expression of a human Eosinophil CC Chemokine Receptor", *J. Biol. Chem.,* 270:16491, (1995).

Post, T.W., et al., "Molecular Characterization of Two Murine Eosinophil β Chemokine Receptors", *J. of Immunol.,* 155:5299–5305, (1995).

Gao, J–L., and Murphy, P.M., "Cloning and Differential Tissue–specific Expression of Three Mouse β Chemokine Receptor–like Genes, Including the Gene for a Functional Macrophage Inflammatory Protein–1α Receptor", *J. of Biol. Chem.,* 270(29):17494–17501, (1995).

Ponath, P.D., et al., "Molecular Cloning and Characterization of a Human Eotaxin Receptor Expressed Selectively on Eosinophils", *J. Exp. Med.,* 183:2437–2448, (1996).

Daugherty B.L., et al., "Cloning, Expression, and Characterization of the Human Eosinophil Eotaxin Receptor", *J. Exp. Med.,* 183:2349–2354, (1996).

Kitaura, M., et al., "Molecular Cloning of Human Eotaxin, an Eosinophil–selective CC Chemokine, and Identification of a Specific Eosinophil Eotaxin Receptor, CC Chemokine Receptor 3", *J. of Biol. Chem.,* 271(13):7725–7730, (1996).

Jose, P.J., et al., "Eotaxin: A Potent Eosinophil Chemoattractant Cytokine Detected in a Guinea Pig Model of Allergic Airways Inflammation", *J. Exp. Med.,* 179:881–887, (1994).

Förster, R., et al., "A general method for screening mAbs specific for G–protein coupled receptors as exemplified by using epitope tagged BLR1–transfected 293 cells and solid–phase cell ELISA", *Biochem. and Biophys. Res. Comm.,* 196(3):1496–1503, (1993).

Ponath, P.D., et al., "Cloning of the Human Eosinophil Chemoattractant, Eotaxin Expression, Receptor Binding, and Functional Properties Suggest a Mechanism for the Selective Recruitment of Eosinophils", *Jour. of Clinical Invest.,* 97(3):604–612, (1996).

Sabroe, I., et al., "Cloning and Characterization of the Guinea Pig Eosinophil Eotaxin Receptor, C–C Chemokine Receptor–3: Blockade Using a Monoclonal Antibody In Vivo," *The Journal of Immunology,* 161:6139–6147 (1998).

Szigeti, V., and Miller R.H., "A Cell Surface Antigen Expressed by Astrocytes and Their Precursors," *GLIA,* 8:20–32 (1993).

Gillaspy, G.E., et al., "Antigenic and Differentiative Heterogeneity Among Human Glioblastomas," *Cancer Letters,* 68:215–224 (1993).

Lyon, J.A., et al., "Monoclonal Antibody Characterization of the 195–Kilodalton Major Surface Glycoprotein of *Plasmodium falciparum* Malaria Schizonts and Merozoites: Identification of Additional Processed Products and a Serotype–Restricted Repetitive Epitope," *J. Immunol.,* 138(3):895–901 (1987).

Forssmann, U., et al., "Eotaxin–2, a Novel CC Chemokine that is Selective for the Chemokine Receptor CCR3, and Acts Like Eotaxin on Human Eosinophil and Basophil Leukocytes," *J. Exp. Med.,* 185(12):2171–2176 (1997).

Heath, H., et al., "Chemokine Receptor Usage by Human Eosinophils," *J. Clin. Invest.,* 99(2):178–184 (1997).

* cited by examiner

```
SEQUENCE RANGE:  1 to 1689

             10          20          30           40
     *      *     *     *     *     *     *      *     *
AAT CCT TTT CCT GGC ACC TCT GAT ATC CTT TTG AAA TTC ATG TTA

    50         60          70          80          90
     *      *     *     *     *     *     *      *     *
AAG AAT CCC TAG GCT GCT ATC ACA TGT GGC ATC TTT GTT GAG TAC

            100         110         120          130
     *      *     *     *     *     *     *      *     *
ATG AAT AAA TCA ACT GGT GTG TTT TAC GAA GGA TGA TTA TGC TTC

   140         150         160         170          180
     *      *     *     *     *     *     *      *     *
ATT GTG GGA TTG TAT TTT TCT TCT TCT ATC ACA GGG AGA AGT GAA

            190         200         210          220
     *      *     *     *     *     *     *      *     *
ATG ACA ACC TCA CTA GAT ACA GTT GAG ACC TTT GGT ACC ACA TCC
Met Thr Thr Ser Leu Asp Thr Val Glu Thr Phe Gly Thr Thr Ser

   230         240         250         260          270
     *      *     *     *     *     *     *      *     *
TAC TAT GAT GAC GTG GGC CTG CTC TGT GAA AAA GCT GAT ACC AGA
Tyr Tyr Asp Asp Val Gly Leu Leu Cys Glu Lys Ala Asp Thr Arg

            280         290         300          310
     *      *     *     *     *     *     *      *     *
GCA CTG ATG GCC CAG TTT GTG CCC CCG CTG TAC TCC CTG GTG TTC
Ala Leu Met Ala Gln Phe Val Pro Pro Leu Tyr Ser Leu Val Phe

   320         330         340         350          360
     *      *     *     *     *     *     *      *     *
ACT GTG GGC CTC TTG GGC AAT GTG GTG GTG GTG ATG ATC CTC ATA
Thr Val Gly Leu Leu Gly Asn Val Val Val Val Met Ile Leu Ile

            370         380         390          400
     *      *     *     *     *     *     *      *     *
AAA TAC AGG AGG CTC CGA ATT ATG ACC AAC ATC TAC CTG CTC AAC
Lys Tyr Arg Arg Leu Arg Ile Met Thr Asn Ile Tyr Leu Leu Asn

   410         420         430         440          450
     *      *     *     *     *     *     *      *     *
CTG GCC ATT TCG GAC CTG CTC TTC CTC GTC ACC CTT CCA TTC TGG
Leu Ala Ile Ser Asp Leu Leu Phe Leu Val Thr Leu Pro Phe Trp

            460         470         480          490
     *      *     *     *     *     *     *      *     *
ATC CAC TAT GTC AGG GGG CAT AAC TGG GTT TTT GGC CAT GGC ATG
Ile His Tyr Val Arg Gly His Asn Trp Val Phe Gly His Gly Met
```

Fig. 1A

```
 500          510           520          530          540
  *     *      *     *      *     *      *     *     *
TGT AAG CTC CTC TCA GGG TTT TAT CAC ACA GGC TTG TAC AGC GAG
Cys Lys Leu Leu Ser Gly Phe Tyr His Thr Gly Leu Tyr Ser Glu

          550          560          570           580
  *     *      *     *      *     *      *     *     *
ATC TTT TTC ATA ATC CTG CTG ACA ATC GAC AGG TAC CTG GCC ATT
Ile Phe Phe Ile Ile Leu Leu Thr Ile Asp Arg Tyr Leu Ala Ile

 590          600           610          620          630
  *     *      *     *      *     *      *     *     *
GTC CAT GCT GTG TTT GCC CTT CGA GCC CGG ACT GTC ACT TTT GGT
Val His Ala Val Phe Ala Leu Arg Ala Arg Thr Val Thr Phe Gly

          640          650          660           670
  *     *      *     *      *     *      *     *     *
GTC ATC ACC AGC ATC GTC ACC TGG GGC CTG GCA GTG CTA GCA GCT
Val Ile Thr Ser Ile Val Thr Trp Gly Leu Ala Val Leu Ala Ala

 680          690           700          710          720
  *     *      *     *      *     *      *     *     *
CTT CCT GAA TTT ATC TTC TAT GAG ACT GAA GAG TTG TTT GAA GAG
Leu Pro Glu Phe Ile Phe Tyr Glu Thr Glu Glu Leu Phe Glu Glu

          730          740          750           760
  *     *      *     *      *     *      *     *     *
ACT CTT TGC AGT GCT CTT TAC CCA GAG GAT ACA GTA TAT AGC TGG
Thr Leu Cys Ser Ala Leu Tyr Pro Glu Asp Thr Val Tyr Ser Trp

 770          780           790          800          810
  *     *      *     *      *     *      *     *     *
AGG CAT TTC CAC ACT CTG AGA ATG ACC ATC TTC TGT CTC GTT CTC
Arg His Phe His Thr Leu Arg Met Thr Ile Phe Cys Leu Val Leu

          820          830          840           850
  *     *      *     *      *     *      *     *     *
CCT CTG CTC GTT ATG GCC ATC TGC TAC ACA GGA ATC ATC AAA ACG
Pro Leu Leu Val Met Ala Ile Cys Tyr Thr Gly Ile Ile Lys Thr

 860          870           880          890          900
  *     *      *     *      *     *      *     *     *
CTG CTG AGG TGC CCC AGT AAA AAA AAG TAC AAG GCC ATC CGG CTC
Leu Leu Arg Cys Pro Ser Lys Lys Lys Tyr Lys Ala Ile Arg Leu

          910          920          930           940
  *     *      *     *      *     *      *     *     *
ATT TTT GTC ATC ATG GCG GTG TTT TTC ATT TTC TGG ACA CCC TAC
Ile Phe Val Ile Met Ala Val Phe Phe Ile Phe Trp Thr Pro Tyr

 950          960           970          980          990
  *     *      *     *      *     *      *     *     *
AAT GTG GCT ATC CTT CTC TCT TCC TAT CAA TCC ATC TTA TTT GGA
Asn Val Ala Ile Leu Leu Ser Ser Tyr Gln Ser Ile Leu Phe Gly
```

Fig. 1B

```
         1000         1010         1020          1030
    *     *     *     *     *     *     *     *     *
AAT GAC TGT GAG CGG ACG AAG CAT CTG GAC CTG GTC ATG CTG GTG
Asn Asp Cys Glu Arg Thr Lys His Leu Asp Leu Val Met Leu Val

  1040         1050          1060         1070         1080
    *     *     *     *     *     *     *     *     *
ACA GAG GTG ATC GCC TAC TCC CAC TGC TGC ATG AAC CCG GTG ATC
Thr Glu Val Ile Ala Tyr Ser His Cys Cys Met Asn Pro Val Ile

         1090         1100         1110          1120
    *     *     *     *     *     *     *     *     *
TAC GCC TTT GTT GGA GAG AGG TTC CGG AAG TAC CTG CGC CAC TTC
Tyr Ala Phe Val Gly Glu Arg Phe Arg Lys Tyr Leu Arg His Phe

  1130         1140          1150         1160         1170
    *     *     *     *     *     *     *     *     *
TTC CAC AGG CAC TTG CTC ATG CAC CTG GGC AGA TAC ATC CCA TTC
Phe His Arg His Leu Leu Met His Leu Gly Arg Tyr Ile Pro Phe

         1180         1190         1200          1210
    *     *     *     *     *     *     *     *     *
CTT CCT AGT GAG AAG CTG GAA AGA ACC AGC TCT GTC TCT CCA TCC
Leu Pro Ser Glu Lys Leu Glu Arg Thr Ser Ser Val Ser Pro Ser

  1220         1230          1240         1250         1260
    *     *     *     *     *     *     *     *     *
ACA GCA GAG CCG GAA CTC TCT ATT GTG TTT TAG GTA GAT GCA GAA
Thr Ala Glu Pro Glu Leu Ser Ile Val Phe ***

         1270         1280         1290         1300
    *     *     *     *     *     *     *     *     *
AAT TGC CTA AAG AGG AAG GAC CAA GGA GAT NAA GCA AAC ACA TTA

  1310         1320          1330         1340         1350
    *     *     *     *     *     *     *     *     *
AGC CTT CCA CAC TCA CCT CTA AAA CAG TCC TTC AAA CCT TCC AGT

         1360         1370         1380          1390
    *     *     *     *     *     *     *     *     *
GCA ACA CTG AAG CTC TTA AGA CAC TGA AAT ATA CAC ACA GCA GTA

  1400         1410          1420         1430         1440
    *     *     *     *     *     *     *     *     *
GCA GTA GAT GCA TGT ACC CTA AGG TCA TTA CCA CAG GCC AGG GCT

         1450         1460         1470          1480
    *     *     *     *     *     *     *     *     *
GGG CAG CGT ACT CAT CAT CAA CCT AAA AAG CAG AGC TTT GCT TCT

  1490         1500          1510         1520         1530
    *     *     *     *     *     *     *     *     *
CTC TCT AAA ATG AGT TAC CTA TAT TTT AAT GCA CCT GAA TGT TAG
```

Fig. 1C

```
        1540           1550            1560             1570
     *       *      *       *       *      *       *       *      *
ATA GTT ACT ATA TGC CGC TAC AAA AAG GTA AAA CTT TTT ATA TTT

 1580           1590             1600            1610             1620
     *       *      *       *       *      *       *       *      *
TAT ACA TTA ACT TCA GCC AGC TAT TAT ATA AAT AAA ACA TTT TCA

        1630           1640            1650             1660
     *       *      *       *       *      *       *       *      *
CAC AAT ACA ATA AGT TAA CTA TTT TAT TTT CTA ATG TGC CTA GTT

 1670           1680
     *       *      *       *
CTT TCC CTG CTT AAT GAA AAG CTT
```

Figure 2A:
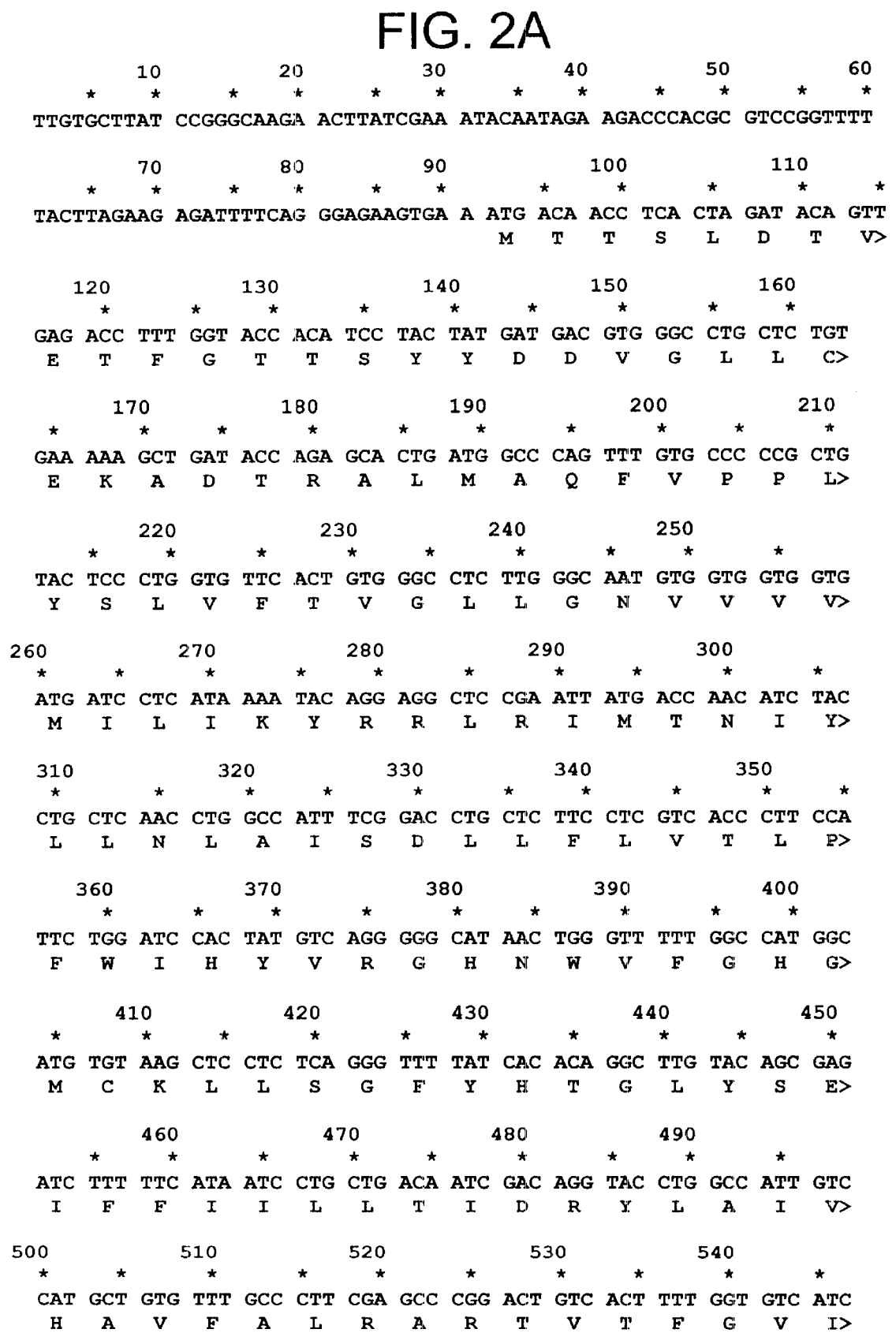

```
         10        20        30        40        50        60
TTGTGCTTAT CCGGGCAAGA ACTTATCGAA ATACAATAGA AGACCCACGC GTCCGGTTTT

         70        80        90          100          110
TACTTAGAAG AGATTTTCAG GGAGAAGTGA A ATG ACA ACC TCA CTA GAT ACA GTT
                                   M   T   T   S   L   D   T   V>

   120          130          140          150          160
GAG ACC TTT GGT ACC ACA TCC TAC TAT GAT GAC GTG GGC CTG CTC TGT
 E   T   F   G   T   T   S   Y   Y   D   D   V   G   L   L   C>

     170          180          190          200          210
GAA AAA GCT GAT ACC AGA GCA CTG ATG GCC CAG TTT GTG CCC CCG CTG
 E   K   A   D   T   R   A   L   M   A   Q   F   V   P   P   L>

       220          230          240          250
TAC TCC CTG GTG TTC ACT GTG GGC CTC TTG GGC AAT GTG GTG GTG GTG
 Y   S   L   V   F   T   V   G   L   L   G   N   V   V   V   V>

260          270          280          290          300
ATG ATC CTC ATA AAA TAC AGG AGG CTC CGA ATT ATG ACC AAC ATC TAC
 M   I   L   I   K   Y   R   R   L   R   I   M   T   N   I   Y>

310          320          330          340          350
CTG CTC AAC CTG GCC ATT TCG GAC CTG CTC TTC CTC GTC ACC CTT CCA
 L   L   N   L   A   I   S   D   L   L   F   L   V   T   L   P>

   360          370          380          390          400
TTC TGG ATC CAC TAT GTC AGG GGG CAT AAC TGG GTT TTT GGC CAT GGC
 F   W   I   H   Y   V   R   G   H   N   W   V   F   G   H   G>

     410          420          430          440          450
ATG TGT AAG CTC CTC TCA GGG TTT TAT CAC ACA GGC TTG TAC AGC GAG
 M   C   K   L   L   S   G   F   Y   H   T   G   L   Y   S   E>

       460          470          480          490
ATC TTT TTC ATA ATC CTG CTG ACA ATC GAC AGG TAC CTG GCC ATT GTC
 I   F   F   I   I   L   L   T   I   D   R   Y   L   A   I   V>

500          510          520          530          540
CAT GCT GTG TTT GCC CTT CGA GCC CGG ACT GTC ACT TTT GGT GTC ATC
 H   A   V   F   A   L   R   A   R   T   V   T   F   G   V   I>
```

FIG. 2B

```
550         560         570         580         590
 *     *     *     *     *     *     *     *     *     *
ACC AGC ATC GTC ACC TGG GGC CTG GCA GTG CTA GCA GCT CTT CCT GAA
 T   S   I   V   T   W   G   L   A   V   L   A   A   L   P   E>

   600         610         620         630         640
     *     *     *     *     *     *     *     *     *
TTT ATC TTC TAT GAG ACT GAA GAG TTG TTT GAA GAG ACT CTT TGC AGT
 F   I   F   Y   E   T   E   E   L   F   E   E   T   L   C   S>

      650         660         670         680         690
 *     *     *     *     *     *     *     *     *     *
GCT CTT TAC CCA GAG GAT ACA GTA TAT AGC TGG AGG CAT TTC CAC ACT
 A   L   Y   P   E   D   T   V   Y   S   W   R   H   F   H   T>

        700         710         720         730
     *     *     *     *     *     *     *     *     *
CTG AGA ATG ACC ATC TTC TGT CTC GTT CTC CCT CTG CTC GTT ATG GCC
 L   R   M   T   I   F   C   L   V   L   P   L   L   V   M   A>

740         750         760         770         780
 *     *     *     *     *     *     *     *     *     *
ATC TGC TAC ACA GGA ATC ATC AAA ACG CTG CTG AGG TGC CCC AGT AAA
 I   C   Y   T   G   I   I   K   T   L   L   R   C   P   S   K>

790         800         810         820         830
 *     *     *     *     *     *     *     *     *     *
AAA AAG TAC AAG GCC ATC CGG CTC ATT TTT GTC ATC ATG GCG GTG TTT
 K   K   Y   K   A   I   R   L   I   F   V   I   M   A   V   F>

   840         850         860         870         880
     *     *     *     *     *     *     *     *     *
TTC ATT TTC TGG ACA CCC TAC AAT GTG GCT ATC CTT CTC TCT TCC TAT
 F   I   F   W   T   P   Y   N   V   A   I   L   L   S   S   Y>

      890         900         910         920         930
 *     *     *     *     *     *     *     *     *     *
CAA TCC ATC TTA TTT GGA AAT GAC TGT GAG CGG AGC AAG CAT CTG GAC
 Q   S   I   L   F   G   N   D   C   E   R   S   K   H   L   D>

        940         950         960         970
     *     *     *     *     *     *     *     *     *
CTG GTC ATG CTG GTG ACA GAG GTG ATC GCC TAC TCC CAC TGC TGC ATG
 L   V   M   L   V   T   E   V   I   A   Y   S   H   C   C   M>

980         990         1000        1010        1020
 *     *     *     *     *     *     *     *     *     *
AAC CCG GTG ATC TAC GCC TTT GTT GGA GAG AGG TTC CGG AAG TAC CTG
 N   P   V   I   Y   A   F   V   G   E   R   F   R   K   Y   L>

1030        1040        1050        1060        1070
 *     *     *     *     *     *     *     *     *     *
CGC CAC TTC TTC CAC AGG CAC TTG CTC ATG CAC CTG GGC AGA TAC ATC
 R   H   F   F   H   R   H   L   L   M   H   L   G   R   Y   I>
```

FIG. 2C

```
 1080           1090           1100           1110          1120
    *      *      *      *      *      *      *      *      *
CCA TTC CTT CCT AGT GAG AAG CTG GAA AGA ACC AGC TCT GTC TCT CCA
 P   F   L   P   S   E   K   L   E   R   T   S   S   V   S   P>

       1130          1140           1150          1160         1170
 *      *      *      *      *      *      *      *      *      *
TCC ACA GCA GAG CCG GAA CTC TCT ATT GTG TTT TAG G TAGATGCAGA
 S   T   A   E   P   E   L   S   I   V   F   *>

     1180         1190
   *      *      *      *
AAATTGCCTA AAGAGGAAGG ACC
```

METHOD OF IDENTIFYING INHIBITORS OF C—C CHEMOKINE RECEPTOR 3

RELATED APPLICATIONS

This application is a continuation-in-part of International Application PCT/US96/00608, (designating the United States), with an International filing date of Jan. 19, 1996, which is a continuation-in-part of U.S. Ser. No. 08/375,199, filed Jan. 19, 1995, the teachings of which are each incorporated herein by reference in their entirety.

GOVERNMENT SUPPORT

Work described herein was supported in whole or in part by a U.S. government grant. The U.S. government has certain rights in this invention.

BACKGROUND

Chemokines, also referred to as intecrines, are soluble, low molecular weight members of the cytokine family which have chemoattractant function. Chemokines are capable of selectively inducing chemotaxis of the formed elements of the blood (other than red blood cells), including leukocytes such as monocytes, macrophages, eosinophils, basophils, mast cells, and lymphocytes, such as T cells, B cells, and polymorphonuclear leukocytes (neutrophils)). In addition to stimulating chemotaxis, other changes can be selectively induced by chemokines in responsive cells, including changes in cell shape, transient rises in the concentration of intracellular free calcium ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines characterized to date are related in primary structure. They share four conserved cysteines, which form disulphide bonds. cDNA cloning and biochemical characterization of several chemokines has revealed that the proteins have a leader sequence of 20–25 amino acids, which is cleaved upon secretion to yield a mature protein of approximately 92–99 amino acids. Based on the conserved cysteine motif, the family is divided into two branches, designated as the C—C chemokines (β chemokines) and the C—X—C chemokines (α chemokines), in which the first two conserved cysteines are adjacent or are separated by an intervening residue, respectively. Baggiolini, M. and C. A. Dahinden, *Immunology Today*, 15: 127–133 (1994)).

The C—X—C chemokines include a number of chemoattractants which are potent chemoattractants and activators of neutrophils, such as interleukin 8 (IL-8), PF4 and neutrophil-activating peptide 2 (NAP-2). The C—C chemokines include molecules such as human monocyte chemotactic proteins 1–3 (MCP-1, MCP-2 and MCP-3), RANTES (Regulated on Activation, Normal T Expressed and Secreted), and the macrophage inflammatory proteins 1α and 1β (MIP-1α and MIP-1β), which have been characterized as chemoattractants and activators of monocytes or lymphocytes, but do not appear to be chemoattractants for neutrophils. For example, recombinant RANTES is a chemoattractant for monocytes, as well as for memory T cells in vitro (Schall, T. J. et al., *Nature*, 347: 669–671 (1990)). More recently a chemokine called lymphotactin with a single cysteine pair in the molecule has been identified which attracts lymphocytes (Kelner, G. S., et al., *Science*, 266: 1395–1359 (1994)).

The C—C chemokines are of great interest because of their potential role in allergic inflammation. For example, MCP-1 induces exocytosis of human basophils, resulting in release of high levels of inflammatory mediators, such as histamine and leukotriene $C_4$. Similarly, there is great interest in the receptors for the C—C chemokines, which trigger these cellular events in response to chemokine binding. A receptor for C—C chemokines has recently been cloned and is reported to bind MIP-1α and RANTES. Accordingly, this MIP-1α/RANTES receptor was designated C—C chemokine receptor 1 (CKR-1; Neote, K. et al., *Cell*, 72: 415–425 (1993); Horuk, R. et al., WO 94/11504, published May 26, 1994; Gao, J.-I. et al., *J. Exp. Med.*, 177: 1421–1427 (1993)). An MCP-1 receptor has also been cloned (Charo, I. F. et al., *Proc. Natl. Acad. Sci. USA*, 91: 2752 (1994)). This receptor, designated CKR-2, is reported to bind MCP-1 with high affinity and MCP-3 with lower affinity (Charo, I. F., et al., *Proc. Natl. Acad. Sci. USA*, 91: 2752–2756 (1994)). CKR-2 has been shown to exist in two isoforms resulting from the use of an alternative splice site in isoform A producing a distinct cytoplasmic tail. Isoform B, which is not spliced in this region, has been shown to be a functional receptor for MCP-1 and MCP-3 in binding and signal transduction assays (Charo, I. F., et al., *Proc. Natl. Acad. Sci. USA*, 91: 2752–2756 (1994); Myers, S. J., et al., *J. Biol. Chem.*, 270: 5786–5792 (1995)). More recently, a new receptor called CKR-4 has been described; cRNA from this receptor was reported to produce a $Ca^{2+}$ activated chloride current in response to MCP-1, MIP-1α, and RANTES when injected in to *X. laevis* oocytes (Power, C. A., et al., *J. Biol. Chem.*, 270: 19495–19500 (1995)).

The MCP-1 receptor (CKR-2) and C—C chemokine receptor 1 are predicted to belong to a superfamily of seven transmembrane spanning G-protein coupled receptors (Gerard C., and Gerard, N. P., *Annu. Rev. Immunol.*, 12: 775–808 (1994); Gerard C., and Gerard N. P., *Curr. Opin. Immunol.*, 6: 140–145 (1994)). This family of G-protein coupled (serpentine) receptors comprises a large group of integral membrane proteins, containing seven transmembrane-spanning regions. The ligands of these receptors include a diverse group of molecules, including small biogenic amine molecules, such as epinephrine and norepinephrine, peptides, such as substance P and neurokinins, and larger proteins, such as chemokines. The receptors are coupled to G proteins, which are heterotrimeric regulatory proteins capable of binding GTP and mediating signal transduction from coupled receptors, for example, by the production of intracellular mediators.

The cloning and sequencing of two IL-8 receptor cDNAs reveals that these C—X—C receptor proteins also share sequence similarity with seven transmembrane-spanning G protein-coupled receptor proteins (Murphy P. M. and H. L. Tiffany, *Science*, 253: 1280–1283 (1991); Murphy et al., WO 93/06299; Holmes, W. E. et al., *Science*, 253: 1278–1280 (1991)). Additional receptors for chemotactic proteins such as anaphylatoxin C5a and bacterial formylated tripeptide fMLP have been characterized by cloning and been found to encode receptor proteins which also share sequence similarity to these seven transmembrane-spanning proteins (Gerard, N. P. and C. Gerard, *Nature*, 349: 614–617 (1991); Boulay, F. et al., *Biochemistry*, 29: 11123–11133 (1990)). Although a number of other proteins with significant sequence similarity and similar tissue and leukocyte subpopulation distribution to known chemokine receptors have been identified and cloned, the ligands for these receptors remain undefined. Thus, these proteins are referred to as orphan receptors.

The isolation and characterization of additional genes and the encoded receptors, and the characterization of the corresponding ligands, is essential to an understanding of the interaction of chemokines with their target cells and the events stimulated by this interaction, including chemotaxis and cellular activation of leukocytes.

SUMMARY OF THE INVENTION

The present invention relates to isolated and/or recombinant nucleic acids which encode a mammalian (e.g., human) receptor protein designated C—C Chemokine Receptor 3 (CKR-3 or CCR3). The invention further relates to recombinant nucleic acid constructs, such as plasmids or retroviral vectors, which contain a nucleic acid which encodes a receptor protein of the present invention, or portions of said receptor. The nucleic acids and constructs can be used to produce recombinant receptor proteins. In another embodiment, the nucleic acid encodes an antisense nucleic acid which can hybridize with a second nucleic acid encoding a receptor of the present invention, and which, when introduced into cells, can inhibit the expression of receptor.

Another aspect of the present invention relates to proteins or polypeptides, referred to herein as isolated, recombinant mammalian CKR-3 receptors. The recombinant CKR-3 receptors or polypeptides can be produced in host cells as described herein. In one embodiment, a receptor protein is characterized by high affinity binding of one or more chemokines, such as eotaxin, RANTES and/or MCP-3, and/or the ability to stimulate a (one or more) cellular response(s) (e.g., chemotaxis, exocytosis, release of one or more inflammatory mediators).

Antibodies reactive with the receptors can be produced using the receptors or portions thereof as immunogen or cells expressing receptor protein or polypeptide, for example. Such antibodies or fragments thereof are useful in therapeutic, diagnostic and research applications, including the purification and study of the receptor proteins, identification of cells expressing surface receptor, and sorting or counting of cells.

Also encompassed by the present invention are methods of identifying ligands of the receptor, as well as inhibitors (e.g., antagonists) or promoters (agonists) of receptor function. In one embodiment, suitable host cells which have been engineered to express a receptor protein or polypeptide encoded by a nucleic acid introduced into said cells are used in an assay to identify and assess the efficacy of ligands, inhibitors or promoters of receptor function. Such cells are also useful in assessing the function of the expressed receptor protein or polypeptide.

According to the present invention, ligands, inhibitors and promoters of receptor function can be identified and further assessed for therapeutic effect. Ligands and promoters can be used to stimulate normal receptor function where needed, while inhibitors of receptor function can be used to reduce or prevent receptor activity. Thus, the present invention provides a new strategy of anti-inflammatory therapy, useful in a variety of inflammatory and autoimmune diseases, comprising administering an inhibitor of receptor function to an individual (e.g., a mammal). In contrast, stimulation of receptor function by administration of a ligand or promoter to an individual provides a new approach to selective stimulation of leukocyte function, which is useful, for example, in the treatment of parasitic infections.

BRIEF DESCRIPTION OF THE DRAWINGS

FIGS. 1A–1D illustrates the nucleotide sequence determined from a genomic clone encoding a human CKR-3 protein also referred to as Eos L2 receptor (SEQ ID NO:1), and the predicted amino acid sequence of the protein encoded by the open-reading frame (SEQ ID NO:2).

FIGS. 2A–2C illustrates the nucleotide sequence determined from the cDNAs encoding a human CKR-3 receptor (SEQ ID NO:3), and the predicted amino acid sequence of the protein encoded by the open-reading frame (SEQ ID NO:4).

FIG. 9A, eosinophils; FIG. 9B, T Cells; FIG. 9C, monocytes; FIG. 9D, neutrophils. Dead cells were excluded based on propidium iodide staining.

FIG. 11A) or to human eosinophils (FIG. 11B). Cells were incubated with 0.6 nM $^{125}$-labeled eotaxin and various concentrations of unlabeled eotaxin (O), RANTES (▼), or MCP-3 (□). After 60 minutes at room temperature, cell pellets were washed and counted. Scatchard plots of unlabeled eotaxin competition were calculated from the data (FIG. 11C, E5 cell line; FIG. 11D, eosinophils).

DETAILED DESCRIPTION OF THE INVENTION

Figure 3:
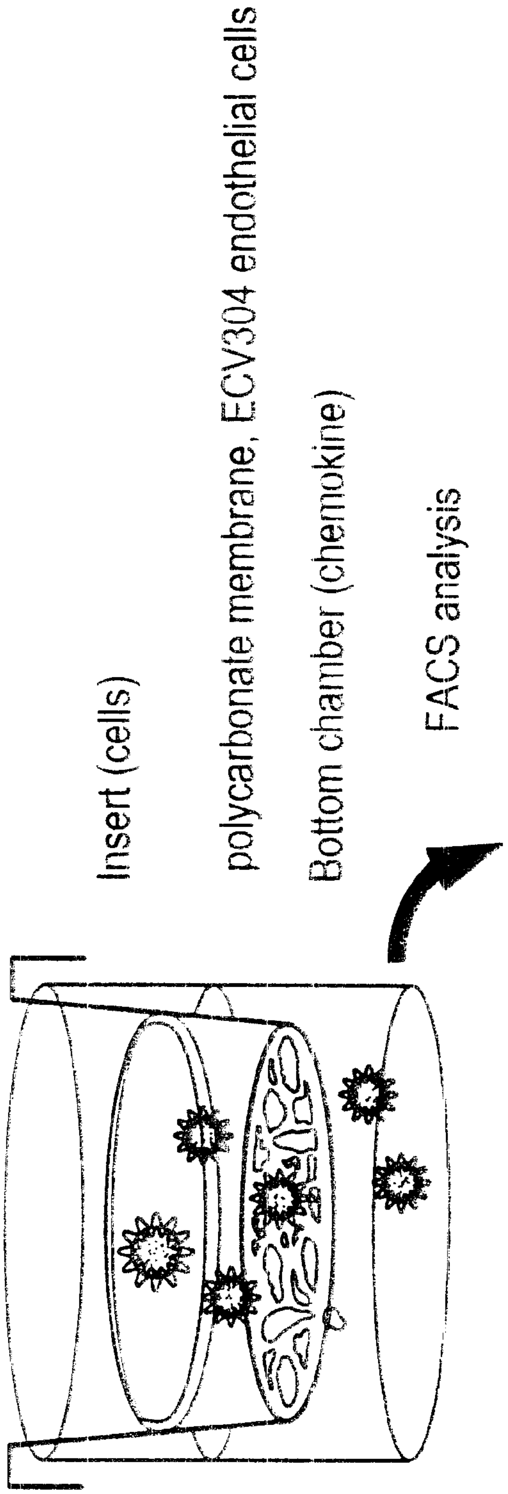
FIG. 3 is an illustration of one type of transendothelial chemotaxis assay. A culture insert is placed into a container, such as a well in a 24-well plate, creating a first and second chamber within the well. ECV304 endothelial cells are grown in a monolayer on the polycarbonate membrane on the inner side of the insert. Cells to be assessed for a response to a substance (e.g., a chemokine) are introduced into the top chamber and the substance is introduced into the bottom chamber. Chemotaxis can be assessed by detecting cells which migrate through the endothelial layer into the bottom chamber, by removing the insert and detecting or counting cells by a suitable method. For example, cells in the bottom chamber can be collected and assessed by flow cytometry (e.g., FACS analysis, light scattering).

As described herein, nucleic acids encoding a novel human receptor, designated Eos L2 or C—C chemokine receptor 3 (CKR-3), also referred to herein as "CCR3", have been isolated. Both human genomic and cDNA clones have been characterized. The cDNA clone was isolated from an eosinophil cDNA library constructed from eosinophils obtained from a patient with hypereosinophilic syndrome. Sequence analysis of the clones revealed a gene containing an open reading frame of 1065 nucleotides encoding a predicted protein of 355 amino acids (FIGS. 1A–1D and 2A–2C; SEQ ID NOS: 2 and 4), which shares amino acid sequence similarity with other C—C chemokine receptors, which are believed to be G protein-coupled receptors and to have a similar structure of seven transmembrane spanning regions.

The predicted proteins encoded by CKR-3 genomic and cDNA clones contain four cysteine residues, one in each of the extracellular domains at positions 24, 106, 183 and 273 (SEQ ID NOS:2 and 4). Cysteines at these positions are conserved in all chemokine receptors, including CKR-1, CKR-2, CKR-4, IL8-RA and IL8-RB. In addition, this receptor contains an amino acid motif, DRYLAIVHA (residues 130–138) (SEQ ID NOS: 2 and 4), which is also highly conserved among C—X—C and C—C chemokine receptors and is predicted to be intracellular. There are two consensus sites for protein kinase C phosphorylation (Kishimoto, A., et al., *J. Biol. Chem.*, 260: 12492–12499 (1985); Woodgett, J. R., *Eur. J. Biochem.*, 161: 177–184 (1986)), one in the third intracellular loop at AA position 231, and one in the cytoplasmic tail at AA position 333. In addition, there are eight serine/threonine residues in the cytoplasmic tail, which may serve as phosphorylation sites for G-protein coupled receptor kinases such as those isolated from neutrophils (Haribabu, B. and R. Snyderman, *Proc. Natl. Acad. Sci. USA*, 90: 9398 (1993)) or other related family members (Benovic, J. L., and Gomez, J., *J. Biol. Chem.*, 268: 19521–19527 (1993); Kunapuli, P., and Benovic, J. L., *Proc. Natl. Acad. Sci. USA*, 90: 5588–5594 (1993)). Serine/threonine rich cytoplasmic tails are also a common feature of chemokine receptors. Unlike CKR-1, CKR-2, CKR-4, IL-8RA and IL-8RB receptors, CKR-3 does not contain sites for N-linked glycosylation in any extracellular domain. The CKR-3 receptor protein is distinct from C—C chemokine receptor 1, also referred to as the MIP-1α/RANTES receptor.

The nucleic acid sequences obtained from genomic and cDNA libraries were co-linear, with the following exceptions. Upstream of the initiation codon the two sequences diverge (at position 78 of FIG. 2A). The genomic clone appears to have an intron which separates the promoter and most of the 5' untranslated region from the coding region. This genomic arrangement is similar to that found in other seven transmembrane-spanning chemoattractant receptors (Gerard, N. P., et al., *Biochemistry,* 32: 1243–1250 (1993); Murphy, P. M., et al., *Gene*, 133: 285–290 (1993)) including IL-8 RA and RB (Ahuja, S. K., et al., *J. Biol. Chem.*, 269: 26381–89 (1994); Sprenger, H., et al., *J. Biol. Chem.*, 269: 11065–11072 (1994); Sprenger, H., et al., *J. Immunol.*, 153: 2524–2532 (1994)) and CKR-1 (Gao, J. L., et al., *J. Exp. Med.*, 177: 1421–1427 (1993)). Furthermore, examination of the genomic sequence around the point of divergence reveals a canonical splice acceptor sequence.

Initial sequence information revealed two regions in which the CDNA sequence appeared to be shifted in frame, resulting from an insertion of a base followed by the deletion of a base, or the deletion of a base followed by the insertion of a base. These alterations resulted in four contiguous amino acid differences in the predicted proteins at positions 263–266 and 276–279, respectively. Other differences led to amino acid differences at positions 182, 196, 197, and 315 of the predicted proteins. The nucleotide sequence presented in SEQ ID NO:5 is a consensus sequence, which includes regions which were sequenced in both clones, and was constructed by simple alignment (base for base) of the initial nucleic acid sequences. SEQ ID NO:6, in which the inital amino acid differences between the cDNA and genomic clones are indicated by Xaa, represents the predicted protein of SEQ ID NO:5. However, further sequence analysis revealed that nucleotide sequences of the open reading frames appear to differ only at a position corresponding to nucleotides 918–919 of FIG. 2B. The genomic clone has a CG at this position, while the cDNA clone has a GC at this position. Thus, the genomic clone codes for threonine (ACG) at position 276 and the cDNA clone codes for serine (AGC) at position 276. The difference may be due to a sequencing ambiguity, or an error introduced into the cDNA during reverse transcription. Alternatively, the conservative subsitution (serine/threonine) could be due to polymorphism between individuals. Another alternative is that the differences are due to mutation of the receptor gene in the eosinophils of the patient from which RNA for CDNA library construction was obtained.

Monoclonal and polyclonal antibodies specific for a C—C chemokine receptor 3 of human origin were produced using an N-terminal synthetic peptide of the receptor. FACS (fluorescence activated cell sorting) analysis using one of the monoclonal antibodies (LS26-5H12) revealed significant expression of this receptor on human eosinophils, but not on leukocytes including monocytes, neutrophils, lymphocytes, T cells, T cell blasts (produced by activation with CD3 MAb) (FIGS. 9A–9D). This pattern of expression was confirmed by Northern analysis with RNA from highly purified leukocyte subsets. However, in some experiments, CKR-3 mRNA or receptor was detected in T lymphocytes; accordingly, it is possible that CKR-3 is expressed on a subset of T lymphocytes (Example 5). In addition, as described herein, a monclonal antibody specific for the C—C chemokine receptor 3 of human origin was produced (Example 10). The mAb, termed 7B11, is an antibody antagonist of C—C chemokine receptor 3 of human origin and the functions of the receptor. The 7B11 hybridoma cell line was deposited on Sep. 25, 1996 under the terms of the Budapest Treaty at the American Type Culture Collection, 10801 University Blvd., Manassas, Va., 20110-2209 under Accession Number HB-12195

Genomic and cDNA clones were also expressed in a variety of systems. Antibody was used to detect expression of receptor from the genomic clone on transfected mammalian cells and baculovirus-transfected insect cells. Stable transfectants of mammalian cells expressing CKR-3 were constructed, and the encoded receptor was shown to bind radiolabeled eotaxin specifically and with high affinity, comparable to the binding affinity observed with eosinophils. Studies with transfected mammalian cells indicated that the receptor also binds RANTES and MCP-3 specifically and with high affinity, but not other CC or CXC chemokines tested. Consistent with the binding data, as shown herein, receptor transfectants generated in a murine B cell lymphoma line migrated in chemotaxis assays in response to eotaxin, RANTES, and MCP-3, but not to any other chemokines tested. When expressed in several heterologous systems, the human receptor did not significantly bind to MIP-1α under the conditions used. Moreover, chemotaxis and ligand binding assays using eosinophils indicate that RANTES and MCP-3 bind eosinophils through a receptor, which is distinct from C—C chemokine receptor 1, the MIP-1α/RANTES receptor.

The role of MIP-1α as an eosinophil chemoattractant has been controversial. Some investigators detect chemotactic responses (Rot, A., et al., *J. Exp. Med.*, 176: 1489–1495 (1995)), whereas others do not (FIG. 4, Example 1; Ebisawa, M., et al., *J. Immunol.*, 153: 2153–2160 (1994); and Ponath, P. D., et al., , *J. Clin. Invest.*, (1996)(in press)). Interestingly, MIP-1α is an eosinophil chemoattractant in the mouse, and this appears to be mediated through the murine CKR-3 homologue, which also binds and signals with murine eotaxin (Post, T. W., et al., *J. Immunol.*, 155: 5299–5305 (1995); the teachings of which are incorporated herein by reference in their entirety).

Using the proteins and antibodies of the present invention, additional ligands, as well as additional cell types (e.g., leukocytes, such as basophils) which express CKR-3 receptor, can be identified. For example, as described herein, using 7B11, it has been demonstrated that basophils express CCR3. The ability of other chemokines to bind mammalian CKR-3 receptors can be assessed according to the present invention.

The cloning and characterization of clones encoding a novel receptor, and the isolation and characterization of the novel CKR-3 receptor which demonstrably binds and mediates chemotaxis in response to chemokines such as eotaxin, RANTES and MCP-3, suggests that this receptor is a member of a family of seven transmembrane spanning G protein-coupled receptors which are involved in selective leukocyte chemotaxis and activation in response to chemokines. The CKR-3 or CCR3 receptor and its mammalian homologs are distinct from the MIP-1α/RANTES receptor and the MCP-1 receptor (i.e., are receptors other than C—C chemokine receptor 1 (CKR-1) and MCP-1 receptor (CKR-2) and their homologs).

Because of the role of chemokine receptors in the selective induction of leukocyte chemotaxis and leukocyte activation in response to chemoattractants, chemokine receptors play a fundamental role in leukocyte migration, and particularly in migration associated with inflammation. Chemokines, produced at sites of inflammation and infection, specifically recruit selected leukocyte subtypes from the circulation to the site of inflammation in the tissues. Subsequent to chemokine binding to a leukocyte chemokine receptor, integrin activation occurs, and leukocytes adhere firmly to the endothelial cell wall via leukocyte integrins and endothelial cell adhesion molecules. The leukocytes become flat in shape, and migrate through the endothelium towards sites of inflammation in the tissues. The specificity of a leukocyte for a tissue or inflammatory site is, in many cases, determined at the level of the chemokine-receptor interaction, rather than at the level of the adhesion interaction between integrin and cellular adhesion molecules.

RANTES and MCP-3 are among the most potent chemotactic cytokines for eosinophils and basophils. In addition, RANTES is reported to be a chemoattractant for memory T cells, a subpopulation of T lymphocytes. As shown herein, RANTES and MCP-3 can induce chemotaxis of eosinophils. CKR-3 receptor proteins described herein also bind RANTES and MCP-3 with high affinity.

As is further shown herein, CKR-3 binds eotaxin specifically and with high affinity (comparable to the binding affinity observed with eosinophils), and the CKR-3 receptor is highly restricted in its expression. Although a number of chemoattractants have been identified for eosinophils, such as RANTES and MCP-3 (Baggiolini, M. and Dahinden, C. A., *Immunol. Today*, 15: 127–33 (1994); Dahinden, C. A., et al., *J. Exp. Med.*, 179: 751–756 (1994); Kameyoshi, Y, et al., *J. Exp. Med.*, 176: 587–592 (1992); Rot, A., et al., *J. Exp. Med.*, 176: 1489–1495 (1995)), as well as PAF, C5a, and IL-16 (Wardlaw, A. J., et al., *J. Clin. Invest.*, 78: 1701–1706 (1986); Gerard, N. P., et al., *J. Biol. Chem.*, 264: 1760–1765 (1989); Rand, T. H., et al., *J. Exp. Med.*, 173: 1521–1528 (1991)), these chemoattracants also induce the migration of other leukocyte cell types. In contrast, the chemokine eotaxin, a potent eosinophil chemoattractant originally identified in guinea pigs and subsequently in mouse and human, is selectively chemotactic for eosinophils (Jose, P. J., et al., *Biochem. Biophys. Res. Commun.*, 205: 788–794 (1994); Jose, P. J., et al., *J. Exp. Med.*, 179: 881–887 (1994); Rothenburg, M. E. et al., *Proc. Natl. Acad. Sci. U.S.A.*, 92:

8960–8964 (1995); Ponath, P. D., et al., *J. Clin. Invest.*, 97(3):604–612 (1996)). In addition, eotaxin binds to and signals through CKR-3 with a high degree of fidelity, in contrast to chemokines such as MCP-3, which binds CKR-1 and CKR-2 (Ben-Baruch, A., et al., *J. Biol. Chem.*, 270: 22123–22128 (1995)) in addition to CKR-3, or MIP-1α, which binds CKR-1 and CKR-4 (Neote, K., et al., *Cell*, 72: 415–425 (1993); Power, C. A., et al., *J. Biol. Chem.*, 270: 19495–19500 (1995)). The restricted expression of CKR-3 on eosinophils, and the fidelity of eotaxin binding to CKR-3, provides a potential mechanism for the selective recruitment and migration of eosinophils within tissues. In this regard, the production of eotaxin within a tissue can lead to selective eosinophil recruitment; eotaxin injection into the skin of rhesus monkeys leads to selective eosinophil migration. In addition, eotaxin was shown to recruit eosinophils in vivo at a 10-fold lower dose than RANTES, similar to the in vitro chemotaxis of CKR-3 transfectants (Ponath, P. D., et al., *J. Clin. Invest.*, 97 (3):604–612 (1996)).

Modulation of mammalian CKR-3 receptor function according to the present invention, through the inhibition or promotion of receptor function, such as binding, signalling or stimulation of a cellular response, provides an effective and selective way of inhibiting or promoting leukocyte-mediated inflammatory action, particularly that of eosinophils, basophils, and/or T cells. Ligands, inhibitors and promoters of CKR-3 receptor function, such as those identified as described herein, can be used to modulate leukocyte function for therapeutic purposes.

Eosinophils do not express the MIP-1α receptor, and do not express significant amounts of MCP-1 receptor. In addition, as noted above, eotaxin and RANTES are some of the most potent chemoattractants for eosinophils, and eotaxin and RANTES bind specifically and with high affinity to the CKR-3 receptor. As a major eosinophil and lymphocyte chemokine receptor, the CKR-3 receptor is an important target for interfering with or promoting eosinophil, basophil, and/or T lymphocyte function. Compounds which inhibit or promote CKR-3 receptor function, such as ligands, inhibitors and promoters identified according to the present method, are particularly useful for modulating eosinophil, basophil, and/or T cell function for therapeutic purposes.

For example, as described herein, anti-CCR3 antibody 7B11, inhibits eosinophil degranulation induced by binding of eotaxin to CCR-3 (Exmaple 11). As also demonstrated herein, 7B11 inhibits basophil chemotaxis to eotaxin and MCP-4, as well as histamine release by basophils in response to chemokines (Example 13).

| Chemokine receptor | other names | ligands defined to date |
|---|---|---|
| CCR1 | CC CKR1 | MIP-1α, RANTES, MCP-3 |
| CCR2a,b | MCP-1Ra,b | MCP-1, MCP-3, MCP-4 |
| CCR3 | CKR-3 | eotaxin, RANTES, MCP-2,3,4 |
| CCR4 | | RANTES, MIP-1α, MCP-1 |
| CCR5 | CC CKR5 | RANTES, MIP-1α, MIP-1β |
| CXCR1 | IL-8 RA, IL-8 R1 | IL-8 |
| CXCR2 | IL-8 RB, IL-8 R2 | IL-8, GROα, NAP-2, ENA-78 |
| CXCR3 | none | IP-10, Mig |
| CXCR4 | Fusin/humstr/Lestr | SDF-1 |

Nucleic Acids, Constructs and Vectors

The present invention relates to isolated and/or recombinant (including, e.g., essentially pure) nucleic acids having sequences which encode a mammalian (e.g., human) receptor protein designated Eos L2 or C—C Chemokine Receptor 3 (CKR-3, also referred to herein as CCR3) or a portion of said receptor. In one embodiment, the nucleic acid or portion thereof encodes a protein or polypeptide having at least one function characteristic of a mammalian C—C chemokine receptor (e.g., a mammalian CKR-3 receptor), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response (e.g., stimulation of chemotaxis, exocytosis or inflammatory mediator release by leukocytes, integrin activation). The present invention also relates more specifically to isolated and/or recombinant nucleic acids or a portion thereof comprising sequences which encode a mammalian CKR-3 receptor or a portion thereof.

The invention further relates to isolated and/or recombinant nucleic acids that are characterized by (1) their ability to hybridize to: (a) a nucleic acid having the sequence SEQ ID NO:1, SEQ ID NO:3 or SEQ ID NO:5, (b) a the complement of any one of SEQ ID NOS:1, 3 or 5, (c) a portion of the foregoing comprising the coding region (nucleotides 181–1245 of SEQ ID NO:1, nucleotides 92–1156 of SEQ ID NO:3, or nucleotides 15–1079 of SEQ ID NO:5), or the RNA counterpart of any one of the foregoing, wherein U is substituted for T; or (2) by their ability to encode a polypeptide having the amino acid sequence SEQ ID NO:2, SEQ ID NO:4 or SEQ ID NO:6 or a functional equivalents thereof (i.e., a polypeptide having ligand binding activity for one or more natural or physiological ligand(s) of the receptor and/or stimulatory function responsive to ligand binding, such that it can stimulate a cellular response (e.g., stimulation of chemotaxis, exocytosis or inflammatory mediator release by leukocytes); or (3) by both characteristics.

In one embodiment, the percent amino acid sequence identity between SEQ ID NOS:2, 4 or 6 and functional equivalents thereof is at least about 70% (≧70%). In a preferred embodiment, functional equivalents of SEQ ID NOS:2, 4 or 6 share at least about 80% sequence identity with SEQ ID NOS:2, 4 or 6, respectively. More preferably, the percent amino acid sequence identity between SEQ ID NOS:2, 4 or 6 and functional equivalents thereof is at least about 90%, and still more preferably, at least about 95%. Isolated and/or recombinant nucleic acids meeting these criteria comprise nucleic acids having sequences identical to sequences of naturally occurring mammalian CKR-3 receptors and portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated by hybridization under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are incorporated herein by reference (see also Example 2). Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for homology.

Isolated and/or recombinant nucleic acids that are characterized by their ability to hybridize to a nucleic acid having the sequence SEQ ID NOS: 1, 3 or 5 or the complements of any one of SEQ ID NOS: 1, 3 or 5 (e.g. under high or moderate stringency conditions) may further encode a protein or polypeptide having at least one function characteristic of a mammalian C—C chemokine receptor (e.g., a mammalian CKR-3 receptor), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response (e.g., stimulation of chemotaxis, exocytosis or inflammatory mediator release by leukocytes, integrin activation).

The signalling function of a protein or polypeptide encoded by hybridizing nucleic acid can be detected by enzymatic assays for G protein activity responsive to receptor binding (e.g., exchange of GTP for GDP on the G protein a subunit, using membrane fractions). G protein coupling can be further assessed, for example, using assays in which stimulation by G protein is blocked by treatment or pretreatment of cells or a suitable cellular fraction (e.g., membranes) with specific inhibitors of G proteins, such as *Bordetella pertussis* toxin (Bischoff, S. C. et al., *Eur. J. Immunol.* 23: 761–767 (1993); Sozzani, S. et al., *J. Immunol.* 147: 2215–2221 (1991)).

The stimulatory function of a protein or polypeptide encoded by hybridizing nucleic acid can be detected by standard assays for chemotaxis or mediator release, using cells expressing the protein or polypeptide (e.g., assays which monitor chemotaxis, exocytosis (e.g., of enzymes such as eosinophil peroxidase,. β-glucuronidase) or mediator release in response to a ligand (e.g., a chemokine such as eotaxin, RANTES or MCP-3) or a promoter.

The binding function of a protein or polypeptide encoded by hybridizing nucleic acid can be detected in binding or binding inhibition assays using membrane fractions containing receptor or cells expressing receptor, for instance (see e.g., Example 9; Van Riper et al., *J. Exp. Med.*, 177: 851–856 (1993); Sledziewski et al., U.S. Pat. No. 5,284,746 (Feb. 8, 1994)). Thus, the ability of the encoded protein or polypeptide to bind a ligand, such as eotaxin, RANTES or MCP-3, an inhibitor and/or promoter, can be assessed. Functions characteristic of a mammalian CKR-3 receptor may also be assessed by other suitable methods (see below).

These methods, alone or in combination with other suitable methods can also be used in procedures for the identification and/or isolation of nucleic acids which encode a polypeptide having the amino acid sequence SEQ ID NO: 2, 4, 6 or functional equivalents thereof, and having an activity detected by the assay. Portions of the isolated nucleic acids which encode polypeptide portions of SEQ ID NO: 2, 4 or 6 having a certain function can be also identified and isolated in this manner.

Nucleic acids of the present invention can be used in the production of proteins or polypeptides. For example, a nucleic acid containing all or part of the coding sequence for a mammalian CKR-3 receptor, or DNA which hybridizes to the sequence SEQ ID NO: 1, 3 or 5, or the complement of any one of SEQ ID NO: 1, 3 or 5, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Antisense Constructs

In another embodiment, the nucleic acid is an antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell using methods known in the art or other suitable methods, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of SEQ ID NO:1, 3 or 5. For example, antisense nucleic acid can be complementary to a target nucleic acid having the sequence of SEQ ID NO: 5 or a portion thereof sufficient to allow hybridization. In another embodiment, the antisense nucleic acid is wholly or partially complementary to and can hybridize with a target nucleic acid which encodes a mammalian CKR-3 receptor (e.g., human Eos L2 receptor).

Antisense nucleic acids are useful for a variety of purposes, including research and therapeutic applications. For example, a construct comprising an antisense nucleic acid can be introduced into a suitable cell to inhibit receptor expression. Such a cell provides a valuable control cell, for instance in assessing the specificity of receptor-ligand interaction with the parent cell or other related cell types. In another aspect, such a construct is introduced into some or all of the cells of a mammal. The antisense nucleic acid inhibits receptor expression, and inflammatory processes mediated by CKR-3 receptors in the cells containing the construct can be inhibited. Thus, an inflammatory disease or condition can be treated using an antisense nucleic acid of the present invention. Suitable laboratory animals comprising an antisense construct can also provide useful models for deficiencies of leukocyte function, and of eosinophil deficiency in particular, and provide further information regarding CKR-3 receptor function. Such animals can provide valuable models of infectious disease, useful for elucidating the role of leukocytes, such as eosinophils and/or T lymphocytes, in host defenses.

Mammalian Nucleic Acids

Because advances in the understanding and treatment of human inflammatory and autoimmune diseases and of parasitic infections would be of tremendous benefit, human CKR-3 or CCR3 was the species selected for most of the experimental work described herein. However, the approaches described to isolate and manipulate the genomic and cDNAs of human CKR-3 (Eos L2), to construct vectors and host strains, and to produce and use the receptor or fragments thereof, can be applied to other mammalian species, including, but not limited to primate (e.g., a primate other than a human, such as a monkey (e.g., cynomolgus monkey)), bovine (e.g., cows), ovine (e.g., sheep), equine (e.g., horses), canine (e.g., dog), feline (e.g., domestic cat) and rodent (e.g., guinea pig, murine species such as rat, mouse) species. The human CKR-3 cDNA or genomic clones described here, or sufficient portions thereof, whether isolated and/or recombinant or synthetic, including fragments within the coding sequence produced by PCR, can be used as probes to detect and/or recover homologous CKR-3 genes (homologs) or other related receptor genes (e.g., novel C—C chemokine receptor genes) from other mammalian species (e.g., by hybridization, PCR or other suitable techniques). This can be achieved using the procedures described herein or other suitable methods.

Proteins and Peptides

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in mammalian cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or polypeptide has at least one function characteristic of a mammalian CKR-3 receptor, such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response (e.g., stimulation of chemotaxis, exocytosis or inflammatory mediator release by leukocytes, integrin activation). As such, these proteins are referred to as CKR-3 proteins of mammalian origin or mammalian chemokine receptor 3 proteins, and include, for example, naturally occurring mammalian CKR-3 receptors, variants of those proteins and/or portions thereof. Such variants include polymorphic variants and natural or artificial mutants, differing by the addition, deletion or substitution of one or more amino acid residues, or modified polypeptides in which one or more residues is modified, and mutants comprising one or more modified residues. An example would be a mammalian CKR-3 receptor protein which binds eotaxin.

In a particularly preferred embodiment, like naturally occurring mammalian CKR-3 receptor proteins or polypeptides, the mammalian CKR-3 receptors of the present invention have ligand binding function for one or more natural or physiological ligand(s) and/or stimulatory function responsive to ligand binding, such that they can stimulate a cellular response (e.g., stimulation of chemotaxis, exocytosis or inflammatory mediator release by leukocytes). For example, in the case of a human chemokine receptor 3 protein, an isolated human CKR-3 protein will bind one or more natural or physiological ligand(s). As shown herein, an isolated human CKR-3 protein binds eotaxin and RANTES specifically and with high affinity, and specifically binds MCP-3. In one embodiment, a human CKR-3 receptor protein or polypeptide also triggers chemotaxis, exocytosis or inflammatory mediator release by leukocytes in response to ligand binding.

The invention further relates to fusion proteins, comprising a mammalian CKR-3 receptor protein or polypeptide (as described above) as a first moiety, linked to a second moiety not occurring in the mammalian CKR-3 receptor as found in nature. Thus, the second moiety can be an amino acid or polypeptide. The first moiety can be in an N-terminal location, C-terminal location or internal to the fusion protein. In one embodiment, the fusion protein comprises a human CKR-3 receptor as the first moiety, and a second moiety comprising a linker sequence and affinity ligand (e.g., an enzyme, an antigen, epitope tag).

Fusion proteins can be produced by a variety of methods. For example, some embodiments can be produced by the insertion of a CKR-3 gene or portion thereof into a suitable expression vector, such as PBLUESCRIPT II SK+/− (Stratagene), pGEX-4T-2 (Pharmacia) and pET-15b (Novagen). The resulting construct is then introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)). In addition, affinity labels provide a means of detecting CKR-3 receptor proteins or polypeptides present in a fusion protein. For example, the cell surface expression or presence in a particular cell fraction of a fusion protein comprising an antigen or epitope affinity label can be detected by means of an appropriate antibody (see, e.g., Example 3).

The invention also relates to isolated and/or recombinant portions of a CKR-3 receptor of mammalian origin, such as a fragment of a human CKR-3 receptor. As is described in more detail below, portions of a mammalian CKR-3 receptor can be produced (e.g., synthetic peptides) and used to produce antibodies. In one embodiment, an isolated and/or recombinant portion (e.g., a peptide) of a selected mammalian CKR-3 receptor has at least one immunological property. As used herein, with reference to a portion of a receptor, an immunological property includes immunoreactivity (bound by antibodies raised against a mammalian CKR-3 receptor protein of the present invention, including a portion thereof), immunogenicity (induces an antibody response against itself when used in a suitable immunization protocol), and/or cross-reactivity (induces antibodies reactive with a selected mammalian receptor). Furthermore, portions of a CKR-3 receptor having at least one function characteristic of mammalian CKR-3 receptors, such as binding activity, signalling activity, or stimulatory function (stimulation of a cellular response), can also be produced. Extensive studies on the structure and function of mammalian G protein-coupled receptors provide the basis for being able to divide mammalian CKR-3 receptors into functional domains (see e.g., Lefkowitz et al., *J. Biol. Chem.*, 263: 4993–4996 (2988); Panayotou and Waterfield, *Curr. Opinion Cell Biol.*, 1: 167–176 (1989)). Furthermore, portions of the receptor can be produced which have full or partial function on their own, or which when joined with another portion of a second receptor (though fully, partially, or nonfunctional alone), constitute a functional protein having at least one function characteristic of a mammalian CKR-3 receptor (e.g., ligand-, inhibitor- or promoter-binding function). (See, e.g., Sledziewski et al., U.S. Pat. No. 5,284, 746 regarding the construction and use of hybrid G protein-coupled receptors useful in detecting the presence of ligand in a test sample).

Method of Producing Recombinant Mammalian CKR-3 Receptors

Another aspect of the invention relates to a method of producing a mammalian CKR-3 receptor or a portion thereof. Constructs suitable for the expression of a mammalian CKR-3 receptor or a portion thereof are also provided. The constructs can be introduced into a suitable host cell. Cells expressing a recombinant mammalian CKR-3 receptor or a portion thereof can be isolated and maintained in culture. Such cells are useful for a variety of purposes such as the production of protein for characterization, isolation and/or purification, and in binding assays for the detection of ligands, or inhibitors or promoters of ligand binding. Suitable host cells can be procaryotic, including bacterial cells such as *E. coli, B. subtilis* and or other suitable bacteria, or eucaryotic, such as fungal or yeast cells (e.g., *Pichia pastoris*, Aspergillus species, *Saccharomyces cerevisiae, Schizosaccharomyces pombe, Neurospora crassa*), or other lower eucaryotic cells, and cells of higher eucaryotes such as those from insects (e.g., Sf9 insect cells) or mammals (e.g., 293 cells, Chinese hamster ovary cells (CHO)). (See, e.g., Ausubel, F. M. et al., eds. *Current Protocols in Molecular Biology*, Greene Publishing Associates and John Wiley & Sons Inc., (1993)).

Host cells which produce a recombinant mammalian CKR-3 receptor protein, portion thereof, or fusion protein can be produced as follows. A nucleic acid encoding all or part of the coding sequence for a mammalian CKR-3 receptor or fusion protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

The transcriptional and/or translational signals of a selected CKR-3 receptor can be used to direct expression. Alternatively, suitable expression vectors are available. Suitable vectors for expression of a nucleic acid encoding all or part of the coding sequence for a mammalian CKR-3 receptor or fusion protein can contain a number of additional components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence (for membrane targeting encoded e.g., by the vector, receptor or other source).

A promoter can be provided for expression in a suitable host cell. Promoters can be constitutive or inducible. For example, a promoter can be operably linked to a nucleic acid encoding the receptor protein, portion thereof or fusion protein, such that it is capable of directing expression of the encoded polypeptide. A variety of suitable promoters for procaryotic (e.g., lac, tac, T3, T7 promoters for *E. coli*) and eukaryotic (e.g., yeast alcohol dehydrogenase (ADH1), SV40, CMV) hosts are available.

In addition, the expression vectors typically comprise a selectable marker for selection of host cells carrying the vector and an origin or replication, in the case of replicable expression vector. Genes encoding products which confer antibiotic or drug resistance are common selectable markers and may be used in prokaryotic (e.g., β-lactamase gene (ampicillin resistance), Tet gene for tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

When the nucleic acid encoding the receptor protein or polypeptide is inserted into the vector, operably linked to one or more of these components, and the resulting construct is introduced into host cells maintained under conditions suitable for expression, the receptor protein or polypeptide is produced. The construct can be introduced into cells by a method appropriate to the host cell selected (e.g., transformation, transfection, electroporation, infection). For production of receptor, host cells comprising the construct are maintained under conditions appropriate for expression, e.g., in the presence of inducer (e.g., n-butyrate), suitable media supplemented with appropriate salts, growth factors, antibiotic, nutritional supplements, etc.

Antibodies

The invention further relates to antibodies reactive with a CKR-3 receptor or portion thereof. In one embodiment, antibodies are raised against an isolated and/or recombinant mammalian CKR-3 protein including portions thereof (e.g., a peptide). In a preferred embodiment, the antibodies specifically bind CKR-3 (CCR3) receptor(s) or a portion thereof. Antibodies which can inhibit one or more functions characteristic of a mammalian CKR-3 (CCR3), such as a binding activity, a signalling activity, and/or stimulation of a cellular response are also encompassed by the present invention, such as an antibody which can inhibit binding of a ligand (i.e., one or more ligands) to CKR-3 (CCR3) and/or one or more functions mediated by CKR-3 (CCR3) in response to a ligand. For example, monoclonal antibody 7B11 can inhibit binding of eotaxin, RANTES, MCP-2, MCP-3 and MCP-4 to human CKR-3 (CCR3). Furthermore, 7B11 can inhibit functions mediated by human CKR-3 (CCR3), including chemokine-induced calcium flux, eosinophil and basophil chemotaxis, histamine release and release of other granule components.

In a particularly preferred embodiment, the antibodies of the present invention have specificity for human CKR-3 (CCR3), and have an epitopic specificity similar to that of murine 7B11 monoclonal antibody described herein. Antibodies with an epitopic specificity similar to that of murine 7B11 monoclonal antibody can be identified by their ability to compete with murine 7B11 for binding to human CCR3 (e.g., to cells bearing human CCR3, such as eosinophils, basophils, or cells transfected with a nucleic acid of the present invention), for example.

The antibodies of the present invention can be polyclonal or monoclonal (see e.g., Example 5), and the term antibody is intended to encompass both polyclonal and monoclonal antibodies. Antibodies of the present invention can be raised against an appropriate immunogen, including proteins or polypeptides of the present invention, such as isolated and/or recombinant mammalian CKR-3 receptor protein or portion thereof, or synthetic molecules, such as synthetic peptides. In addition, cells which express receptor, such as transfected cells, can be used as immunogens or in a screen for antibody which binds receptor. See for example, Chuntharapai et al., *J. Immunol.* 152: 1783–1789 (1994)).

Preparation of immunizing antigen, and polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

In addition, functional fragments of antibodies, including fragments of chimeric, humanized, primatized or single chain antibodies, can also be produced. Functional fragments of foregoing antibodies retain at least one binding function and/or modulation function of the full-length antibody from which they are derived. Preferred functional fragments retain an antigen binding function of a corresponding full-length antibody (e.g., specificity for a mammalian CKR-3 (CCR3)). Particularly preferred functional fragments retain the ability to inhibit one or more functions characteristic of a mammalian CKR-3 (CCR3), such as a binding activity, a signalling activity, and/or stimulation of a cellular response. For example, in one embodiment, a functional fragment can inhibit the interaction of CKR-3 (CCR3) with one or more of its ligands (e.g., eotaxin, RANTES, MCP-2, MCP-3, MCP-4) and/or can inhibit one or more receptor-mediated functions, such as eosinophil or basophil chemotaxis and/or degranulation induced by chemokine binding to CKR-3 (CCR3). For example, antibody fragments capable of binding to a mammalian CKR-3 receptor or portion thereof, including, but not limited to, Fv, Fab, Fab' and $F(ab')_2$ fragments are encompassed by the invention. Such fragments can be produced by enzymatic cleavage or by recombinant techniques. For instance, papain or pepsin cleavage can generate Fab or $F(ab')_2$ fragments, respectively. Antibodies can also be produced in a variety of truncated forms using antibody genes in which one or more stop codons has been introduced upstream of the natural stop site. For example, a chimeric gene encoding a $F(ab')_2$ heavy chain portion can be designed to include DNA sequences encoding the $CH_1$ domain and hinge region of the heavy chain.

The term "humanized immunoglobulin" as used herein refers to an immunoglobulin comprising portions of immunoglobulins of different origin, wherein at least one portion is of human origin. Accordingly, the present invention relates to a humanized immunoglobulin having binding specificity for a mammalian CCR3 (e.g., human CCR3), said immunoglobulin comprising an antigen binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with murine 7B11 monoclonal antibody for binding to human CCR3 (e.g., to cells bearing human CCR3, such as eosinophils, basophils, or cells transfected with a nucleic acid of the present invention). In a preferred embodiment, the antigen binding region of the humanized immunoglobulin is derived from 7B11 monoclonal antibody. Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., *Science*, 242: 423–426 (1988)), regarding single chain antibodies.

The antibodies of the present invention are useful in a variety of applications, including research, diagnostic and therapeutic applications. In one embodiment, the antibodies are labeled with a suitable label (e.g., fluorescent label, chemiluminescent label, isotope label, epitope or enzyme label). For instance, they can be used to isolate and/or purify receptor or portions thereof, and to study receptor structure (e.g., conformation) and function.

The antibodies of the present invention can also be used to modulate receptor function in research and therapeutic applications. For instance, antibodies can act as inhibitors to inhibit (reduce or prevent) (a) binding (e.g., of a ligand, a second inhibitor or a promoter) to the receptor, (b) a receptor signalling, (c) and/or a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand).

Antibodies which bind receptor can also act as agonists of receptor function, triggering or stimulating a receptor function, such as a signalling and/or a stimulatory function of a receptor (e.g., chemotaxis, exocytosis or pro-inflammatory mediator release) upon binding to receptor.

In addition, the various antibodies of the present invention can be used to detect or measure the expression of receptor, for example, on leukocytes such as eosinophils, basophils, and lymphocytes, or on cells transfected with a receptor gene. Thus, they also have utility in applications such as cell sorting (e.g., flow cytometry, fluorescence activated cell sorting), for diagnostic or research purposes.

Anti-idiotypic antibodies are also provided. Anti-idiotypic antibodies recognize antigenic determinants associated with the antigen-binding site of another antibody. Anti-idiotypic antibodies can be prepared a against second antibody by immunizing an animal of the same species, and preferably of the same strain, as the animal used to produce the second antibody. See e.g., U.S. Pat. No. 4,699,880.

In one embodiment, antibodies are raised against receptor or a portion thereof, and these antibodies are used in turn to produce an anti-idiotypic antibody. The anti-Id produced thereby can bind compounds which bind receptor, such as ligands, inhibitors or promoters of receptor function, and can be used in an immunoassay to detect or identify or quantitate such compounds. Such an anti-idiotypic antibody can also be an inhibitor of receptor function, although it does not bind receptor itself.

Anti-idiotypic (i.e., Anti-Id) antibody can itself be used to raise an anti-idiotypic antibody (i.e., Anti-anti-Id). Such an antibody can be similar or identical in specificity to the original immunizing antibody. In one embodiment, antibody antagonists which block binding to receptor can be used to raise Anti-Id, and the Anti-Id can be used to raise Anti-anti-Id, which can have a specificity which is similar or identical to that of the antibody antagonist. These anti-anti-Id antibodies can be assessed for inhibitory effect on receptor function to determine if they are antagonists.

Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared.

Identification of Ligands, Inhibitors or Promoters of Receptor Function

As used herein, a ligand is a substance which binds to a receptor protein. A ligand of a selected mammalian CKR-3 receptor is a substance which binds to the selected mammalian receptor. In one embodiment, a ligand can bind selectively to two or more mammalian chemokine receptors, including CKR-3. In a preferred embodiment, ligand binding of a mammalian CKR-3 receptor occurs with high affinity. The term ligand refers to substances including, but not limited to, a natural ligand, whether isolated and/or purified, synthetic, and/or recombinant, a homolog of a natural ligand (e.g., from another mammal), antibodies, portions of such molecules, and other substances which bind receptor. A natural ligand of a selected mammalian receptor can bind to the receptor under physiological conditions, and is of a mammalian origin which is the same as that of the mammalian CKR-3 receptor. The term ligand encompasses substances which are inhibitors or promoters of receptor activity, as well as substances which bind but lack inhibitor or promoter activity.

As used herein, an inhibitor is a substance which inhibits at least one function characteristic of a mammalian C—C chemokine receptor (e.g., a mammalian CKR-3 receptor), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response. The term inhibitor refers to substances including antagonists which bind receptor (e.g., an antibody, a mutant of a natural ligand, other competitive inhibitors of ligand binding), and substances which inhibit receptor function without binding thereto (e.g., an anti-idiotypic antibody).

As used herein, a promoter is a substance which promotes (induces or enhances) at least one function characteristic of a mammalian C—C chemokine receptor (e.g., a mammalian CKR-3 receptor), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response. The term promoter refers to substances including agonists which bind receptor (e.g., an antibody, a homolog of a natural ligand from another species), and substances which promote receptor function without binding thereto (e.g., by activating an associated protein).

The assays described below, which rely upon the nucleic acids and proteins of the present invention, can be used, alone or in combination with each other or other suitable methods, to identify ligands, inhibitors or promoters of a mammalian CKR-3 receptor protein or polypeptide. Human CKR-3 does not usually exist in cells at levels suitable for high-throughput screening; thus, cells which contain and express a nucleic acid of the present invention are particularly valuable in identifying ligands, inhibitors and promoters of CKR-3 receptor proteins.

Upon isolation of a CKR-3 receptor gene from a mammal, the gene can be incorporated into an expression system to produce a receptor protein or polypeptide as described above. An isolated and/or recombinant receptor protein or polypeptide, such as a receptor expressed in cells stably or transiently transfected with a construct comprising a nucleic acid of the present invention, or in a cell fraction (e.g., membrane fraction from transfected cells) containing receptor, can be used in tests for receptor function. The receptor can be further purified if desired. Testing of receptor function can be carried out in vitro or in vivo.

An isolated, recombinant mammalian CKR-3 receptor protein, such as a human CKR-3 receptor as that shown in FIGS. 1A–1D (see also, SEQ ID NO:2), FIGS. 2A–2C (see also, SEQ ID NO:4) or SEQ ID NO:6, can be used in the present method, in which the effect of a compound is assessed by monitoring receptor function as described herein or using other suitable techniques. For example, stable or transient transfectants, such as A31/293/#20 stable transfectants (see e.g., Example 9), stable tranfectants of mouse L1-2 pre-B cells (see e.g., Example 3), baculovirus infected Sf9 cells (see e.g., Example 4), can be used in binding assays. Stable transfectants of mouse L1-2 pre-B cells or of other suitable cells capable of chemotaxis can be used (see e.g., Example 3) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

In one embodiment, phage display methodology is used. For example, receptor is contacted with a phage (e.g., a phage or collection of phage such as a library) displaying a polypeptide under conditions appropriate for receptor binding (e.g., in a suitable binding buffer). Phage bound to receptor is selected using standard techniques or other suitable methods. Phage can be separated from receptor using a suitable elution buffer. For example, a change in the ionic strength or pH can lead to a release of phage. Alternatively, the elution buffer can comprise a release component or components designed to disrupt binding of compounds (e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide is characterized (e.g., by sequencing phage DNA). The polypeptides identified can be produced and further tested for ligand binding, inhibitor and/or promoter function. Analogs of such peptides can be produced which will have increased stability or other desirable properties.

In one embodiment, phage expressing and displaying a fusion proteins comprising a coat protein with an N-terminal peptide encoded by random sequence nucleic acids can be produced. Suitable host cells expressing a receptor protein or polypeptide of the present invention are contacted with the phage, bound phage are selected, recovered and characterized. (See e.g., Doorbar, J. and G. Winter, *J. Mol. Biol.*, 244: 361 (1994) discussing a phage display procedure used with a G protein-coupled receptor).

Other sources of potential ligands, inhibitors and/or promoters of a mammalian CKR-3 receptor include, but are not limited to, substances such as other chemoattractants; other chemokines (e.g., eotaxin), such as a mammalian chemokine from the same mammal as the receptor, from another mammal (e.g., for a human receptor, a homolog of a human chemokine obtained from a non-human source); variants of other chemoattractants or chemokines, such as naturally occurring, synthetic or recombinant variants; other mammalian CKR-3 receptor ligands, inhibitors and/or promoters (e.g., antibodies, antagonists, agonists), and variants thereof; other G-protein coupled receptor ligands, inhibitors and/or promoters (e.g., antagonists or agonists); and soluble portions of a mammalian CKR-3 receptor, such as a suitable receptor peptide or analog which can inhibit receptor function (see e.g., Murphy, R. B., WO 94/05695).

The in vitro method of the present invention can be used in high-throughput screening. These assays can be adapted for processing large numbers of samples (e.g., a 96 well format). For such screening, use of a host cell expressing receptor, instead of isolated eosinophils, is preferred because of the difficulty in isolating eosinophils.

For binding assays, high level expression of receptor in a suitable host cell is preferred. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors; see Example 3).

Binding Assays

The isolated and/or recombinant receptor proteins, portions thereof, or suitable fusion proteins of the present invention, can be used in a method to select and identify compounds which bind to a (one or more) mammalian CKR-3 receptor protein, such as human CKR-3 receptor, and which are ligands, or potential inhibitors or promoters of receptor activity. Compounds selected by the method, including ligands, inhibitors or promoters, can be further assessed for an inhibitory or stimulatory effect on receptor function and/or for therapeutic utility.

In one embodiment, compounds which bind to an active, isolated and/or recombinant mammalian CKR-3 receptor protein or polypeptide are identified by the method. In this embodiment, the receptor protein or polypeptide used has at least one function characteristic of a CKR-3 receptor, such as a signalling activity (e.g., activation of a mammalian G protein), stimulatory function (e.g., stimulation of chemotaxis or inflammatory mediator release), and/or binding function (e.g., ligand, inhibitor and/or promoter binding). In a particularly preferred embodiment, the isolated and/or recombinant mammalian CKR-3 receptor protein or polypeptide has ligand binding function, such that it binds a natural ligand of the receptor.

For example, an isolated and/or recombinant mammalian CKR-3 receptor protein or polypeptide can be maintained under conditions suitable for binding, the receptor is contacted with a compound to be tested, and binding is detected or measured. In one embodiment, a receptor protein can be expressed in cells stably or transiently transfected with a construct comprising a nucleic acid sequence which encodes a receptor of the present invention. The cells are maintained under conditions appropriate for expression of receptor. The cells are contacted with a compound under conditions suitable for binding (e.g., in a suitable binding buffer), and binding is detected by standard techniques. To measure binding, the extent of binding can be determined relative to a suitable control (e.g., compared with background determined in the absence of compound, compared with binding of a second compound (i.e., a standard), compared with binding of compound to untransfected cells). Optionally, a cellular fraction, such as a membrane fraction, containing receptor can be used in lieu of whole cells (see e.g., Example 9).

In one embodiment, the compound is labeled with a suitable label (e.g., fluorescent label, isotope label), and binding is determined by detection of the label. Specificity of binding can be assessed by competition or displacement, for example, using unlabeled compound or a second ligand as competitor.

Ligands of the mammalian receptor, including natural ligands from the same mammalian species or from another species, can be identified in this manners The binding activity of a promoter or inhibitor which binds receptor can also be assessed using such a ligand binding assay.

Binding inhibition assays can also be used to identify ligands, and inhibitors and promoters which bind receptor and inhibit binding of another compound such as a ligand. For example, a binding assay can be conducted in which a reduction in the binding of a first compound (in the absence of a second compound), as compared binding of the first compound in the presence of the second compound, is detected or measured. The receptor can be contacted with the first and second compounds simultaneously, or one after the other, in either order. A reduction in the extent of binding of the first compound in the presence of the second compound, is indicative of inhibition of binding by the second compound. For example, binding of the first compound could be decreased or abolished.

In one embodiment, direct inhibition of the binding of a first compound (e.g., a chemokine such as RANTES) to a human CKR-3 receptor by a second test compound is monitored. For example, the ability of a compound to inhibit the binding of $^{125}$I-labeled RANTES or $^{125}$I-labeled MCP-3 to human CKR-3 can be monitored. Such an assay can be conducted using either whole cells (e.g., eosinophils, or a suitable cell line containing nucleic acid encoding a human CKR-3 receptor) or a membrane fraction from said cells, for instance.

Other methods of identifying the presence of a compound (s) which bind a receptor are available, such as methods which monitor events which are triggered by receptor binding, including signalling function and/or stimulation of a cellular response (See below).

It will be understood that the inhibitory effect of antibodies of the present invention can be assessed in a binding inhibition assay. Competition between antibodies for receptor binding can also be assessed in the method in which the first compound in the assay is another antibody, under conditions suitable for antibody binding.

Ligands, as well as receptor-binding inhibitors (e.g., antagonists) and promoters (e.g., agonists), which are identified in this manner, can be further assessed to determine whether, subsequent to binding, they act to inhibit or activate other functions of CKR-3 receptors and/or to assess their therapeutic utility.

Signalling Assays

The binding of a ligand or promoter, such as an agonist, can result in signalling by a G protein-coupled receptor, and the activity of G proteins is stimulated. The induction of induce signalling function by a compound can be monitored using any suitable method. For example, G protein activity, such as hydrolysis of GTP to GDP, or later signalling events triggered by receptor binding, such as induction of rapid and transient increase in the concentration of intracellular (cytosolic) free calcium $[Ca^{2+}]_i$, can be assayed by methods known in the art or other suitable methods (see e.g., Neote, K. et al., *Cell*, 72: 415–425 1993); Van Riper et al., *J. Exp. Med.*, 177: 851–856 (1993); Dahinden, C. A. et al., *J. Exp. Med.*, 179: 751–756 (1994).

The functional assay of Sledziewski et al. using hybrid G protein coupled receptors can also be used to monitor the ability a ligand or promoter to bind receptor and activate a G protein (Sledziewski et al., U.S. Pat. No. 5,284,746, the teachings of which are incorporated herein by reference).

A biological response of the host cell (triggered by binding to hybrid receptor) is monitored, detection of the response being indicative of the presence of ligand in the test sample. Sledziewski et al. describes a method of detecting the presence of a ligand in a test sample, wherein the ligand is a compound which is capable of being bound by the ligand-binding domain of a receptor. In one embodiment of the method, yeast host cells are transformed with a DNA construct capable of directing the expression of a biologically active hybrid G protein-coupled receptor (i.e., a fusion protein). The hybrid receptor comprises a mammalian G protein-coupled receptor having at least one domain other than the ligand-binding domain replaced with a corresponding domain of a yeast G protein-coupled receptor, such as a STE2 gene product. The yeast host cells containing the construct are maintained under conditions in which the hybrid receptor is expressed, and the cells are contacted with a test sample under conditions suitable to permit binding of ligand to the hybrid receptor. The assay is conducted as described and the biological response of the host cell (triggered by binding to hybrid receptor) is monitored, detection of the response being indicative of a signalling function.

For instance, an assay is provided in which binding to a hybrid receptor derived from STE2 gene product leads to induction of the BAR1 promoter. Induction of the promoter is measured by means of a reporter gene (β-gal), which is linked to the BAR1 promoter and introduced into host cells on a second construct. Expression of the reporter gene can be detected by an in vitro enzyme assay on cell lysates or by the presence of blue colonies on plates containing an indicator (X-gal) in the medium, for example.

In another embodiment, the assay is used to identify potential inhibitors of receptor function. The inhibitory activity of a compound can be determined using a ligand or promoter in the assay, and assessing the ability of the compound to inhibit the activity induced by ligand or promoter.

Variants of known ligands can also be screened for reduced ability (decreased ability or no ability) to stimulate activity of a coupled G protein. In this embodiment, although the compound has ligand binding activity (as determined by another method in advance or later), engagement of the receptor does not trigger or only weakly triggers activity of a coupled G protein. Such compounds are potential antagonists, and can be further assessed using a suitable assay. For instance, the same assay can be conducted in the presence of a ligand or promoter, and the ability of the compound to inhibit the activity of a ligand or promoter is assessed.

Chemotaxis and Assays of Cellular Stimulation

Chemotaxis assays can also be used to assess receptor function. These assays are based on the functional migration of cells in vitro or in vivo induced by a compound, and can be used to assess the binding and/or chemoattractant effect of ligands, inhibitors, or promoters. The use of an in vitro transendothelial chemotaxis assay is described in Example 1. Springer et al. describe a transendothelial lymphocyte chemotaxis assay (Springer et al., WO 94/20142, published Sep. 15, 1994, the teachings of which are incorporated herein by reference; see also Berman et al., *Immunol Invest.* 17: 625–677 (1988)). Migration across endothelium into collagen gels has also been described (Kavanaugh et al., *J. Immunol*, 146: 4149–4156 (1991)). Stable transfectants of mouse L1-2 pre-B cells or of other suitable host cells capable of chemotaxis can be used (see e.g., Example 3) in chemotaxis assays, for example.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen.

For example, one can detect or measure the migration of cells in a suitable container (a containing means), from a first chamber into or through a microporous membrane into a second chamber which contains a compound to be tested, and which is divided from the first chamber by the membrane. A suitable membrane, having a suitable pore size for monitoring specific migration in response to compound, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed by determining the presence of the label adherent to the membrane and/or present in the second chamber using an appropriate method (e.g., by detecting radioactivity, fluorescence, immunoassay). The extent of migration induced by a compound can be determined relative to a suitable control (e.g., compared to background migration determined in the absence of the compound, to the extent of migration induced by a second compound (i.e., a standard), compared with migration of untransfected cells induced by the compound).

Chambers can be formed from various solids, such as plastic, glass, polypropylene, polystyrene, etc. Membranes which are detachable from the chambers, such as a BIOCOAT (Collaborative Biomedical Products) or TRANSWELL (Costar, Cambridge, Mass.) culture insert, facilitate counting adherent cells.

In the container, the filter is situated so as to be in contact with fluid containing cells in the first chamber, and the fluid in the second chamber. Other than the test compound or additional ligand, inhibitor, or promoter present for the purpose of the assay, the fluid on either side of the membrane is preferably the same or substantially similar. The fluid in the chambers can comprise protein solutions (e.g., bovine serum albumin, fetal calf serum, human serum albumin) which may act to increase stability and inhibit nonspecific binding of cells, and/or culture media.

In a preferred embodiment, particularly for eosinophils, eosinophil-like cells, lymphocytes, or cells expressing a CKR-3 receptor, transendothelial migration is monitored. A transendothelial migration assay is preferred. Such assays are better physiological models, because they more accurately recapitulate in vivo conditions in which leukocytes emigrate from blood vessels toward chemoattractants present in the tissues at sites of inflammation by crossing the endothelial cell layer lining the vessel wall. In addition, transendothelial assays have lower background (signal to noise ratio).

In this embodiment, transmigration through an endothelial cell layer assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.) or a suitable cell line, such as the ECV 304 cell line used in Example 1. To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment, a chemotaxis is used to test for ligand or promoter activity of a compound, a composition comprising cells capable of migration and expressing a mammalian CKR-3 receptor are placed in the first chamber, and a composition comprising the compound to be tested is placed in the second chamber, preferably in the absence of other ligands or promoters capable of inducing chemotaxis of the cells in the first chamber (having chemoattractant function). However, one or more ligands or promoters having chemoattractant function may be present. Compounds which can bind receptor and induce chemotaxis of the cells expressing a mammalian CKR-3 receptor in this assay are ligands or promoters of receptor function.

In one embodiment used to test for an inhibitor, a composition comprising cells capable of migration and expressing a mammalian CKR-3 receptor are placed in the first chamber. A composition comprising one or more ligands or promoters capable of inducing chemotaxis of the cells in the first chamber (having chemoattractant function) is placed in the second chamber. Either shortly before the cells are placed in the first chamber, or simultaneously with the cells, a composition comprising the compound to be tested is placed, preferably, in the first chamber. Compounds which can bind receptor and inhibit the induction of chemotaxis, by a ligand or promoter, of the cells expressing a mammalian CKR-3 receptor in this assay are inhibitors of receptor function (i.e., inhibitors of stimulatory function). A reduction in the extent of migration induced by the ligand or promoter in the presence of the test compound, is indicative of inhibitory activity. (see e.g., Example 5). Separate binding studies (see above) could be performed to determine whether inhibition is a result of binding of the test compound to receptor or occurs via a different mechanism.

In vivo assays which monitor leukocyte infiltration of a tissue, in response to injection of a compound in the tissue, are described below (see Models of Inflammation). These models measure the ability of cells to respond to a ligand or promoter by emigration and chemotaxis to a site of inflammation.

In addition to the methods described, the effects of a ligand, inhibitor or promoter on the stimulatory function of the receptor can be assessed by monitoring cellular responses induced by active receptor, using suitable host cells containing receptor. Similarly, these assays can be used to determine the function of a receptor. For instance, exocytosis (e.g., degranulation of eosinophils leading to release of eosinophil cationic protein and/or one or more enzymes, or other granule components; release of histamine from basophils), inflammatory mediator release (such as release of bioactive lipids such as leukotrienes (e.g., leukotriene $C_4$)), and respiratory burst (Rot, A. et al., *J. Exp. Med.*, 176: 1489–1495 (1992)), can be monitored by methods known in the art or other suitable methods. See e.g., Bischoff. S. C. et al., *Eur. J. Immunol.*, 23: 761–767 (1993) and Baggliolini, M. and C. A. Dahinden, *Immunology Today*, 15: 127–133 (1994) and references cited therein).

In one embodiment, a ligand, inhibitor and/or promoter is identified by monitoring the release of an enzyme upon degranulation or exocytosis by a cell capable of this function. Cells containing a nucleic acid of the present invention, which encodes an active receptor protein capable of stimulating exocytosis or degranulation are maintained in a suitable medium under suitable conditions, whereby receptor is expressed and degranulation can be induced. The receptor is contacted with a compound to be tested, and enzyme release is assessed. The release of an enzyme into the medium can be detected or measured using a suitable assay, such as in an immunological assay, or biochemical assay for enzyme activity.

The medium can be assayed directly, by introducing components of the assay (e.g., substrate, co-factors, antibody) into the medium (e.g., before, simultaneous with or after the cells and compound are combined). Alternatively, the assay can be performed on medium which has been separated from the cells or further fractionated prior to assay.

For example, convenient assays for are available for enzymes such as β-glucuronidase and eosinophil peroxidase (White, S. R. et al., A kinetic assay for eosinophil peroxidase activity in eosinophils and eosinophil conditioned media, *J. Immunol. Methods*, 144(2): 257–63 (1991)).

Stimulation of degranulation by a compound can be indicative that the compound is a ligand or promoter of a mammalian CKR-3 receptor. In another embodiment, inhibition of degranulation is indicative of an inhibitor. In this embodiment, the cells expressing receptor are combined with a ligand or promoter, and a compound to be tested is added before, after or simultaneous therewith.

Models of Inflammation

A variety of in vivo models of inflammation are available, which can be used to assess the effects of ligands, inhibitors, or promoters in vivo as therapeutic agents.

For example, primate models with eosinophilic infiltration to the lung, are available for in vivo testing (see e.g., Wegner, C. D. et al., *Science*, 247: 456 (1990)). In one embodiment, an antibody (e.g., a monoclonal antibody) which reacts with human CKR-3, and which cross-reacts with primate CKR-3, is administered to the animal. A number of parameters can be measured to assess in vivo efficacy including, but not limited to, the number of eosinophils in broncoalveolar lavage fluid, respiratory compliance, and respiratory rate. A decrease in symptoms of airway hypersensitivity is indicative of therapeutic benefit.

In addition, a sheep model for asthma, a guinea pig model for passive cutaneous anaphylaxis, or other suitable model can be used to assess compounds in vivo (see e.g., Weg, V. B. et al., *J. Exp. Med.*, 177: 561 (1993); Abraham, W. M. et al., *J. Clin. Invest.*, 93: 776 (1994)).

In addition, leukocyte infiltration upon intradermal injection of a compound into a suitable animal, such as rabbit, rat, or guinea pig, can be monitored (see e.g., Van Damme J. et al., *J. Exp. Med.*, 176: 59–65 (1992); Zachariae, C. O. C. et al., *J. Exp. Med.* 171: 2177–2182 (1990); Jose, P. J. et al., *J. Exp. Med.* 179: 881–887 (1994)). In one embodiment, skin biopsies are assessed histologically for infiltration of leukocytes (e.g., eosinophils, granulocytes). In another embodiment, labeled cells (e.g., stably transfected cells expressing a CKR-3 receptor, labeled with $^{111}$In for example) capable of chemotaxis and extravasation are administered to the animal. Infiltration of cells in response to injection of a test sample (e.g., a compound to be tested in a suitable buffer or physiological carrier) is indicative of the presence of a ligand or promoter, such as an agonist, in the sample. These assays can also be modified to identify inhibitors of chemotaxis and leukocyte extravasation. For example, an inhibitor can be administered, either before, simultaneously with or after ligand or agonist is administered to the test animal. A decrease of the extent of infiltration in the presence of inhibitor as compared with the extent of infiltration in the absence of inhibitor is indicative of inhibition.

Diagnostic Applications

The present invention has a variety of diagnostic applications. These applications include, but are not necessarily limited to the applications discussed herein.

Mutation(s) in genes encoding a mammalian CKR-3 receptor protein can cause defects in at least one function of the encoded receptor, thereby reducing or enhancing receptor function. For instance, mutations which produce a variant of receptor or alter the level of expression, can reduce or enhance receptor function, reducing or enhancing, the inflammatory processes mediated by receptor.

For example, the methods of detecting or measuring receptor function can be used to characterize the activity of receptors in cells (e.g., leukocytes) of an individual or of receptors isolated from such cells. In these assays, reduced or enhanced receptor function can be assessed.

The nucleic acids of the present invention provide reagents (e.g., probes, PCR primers) which can be used to screen for, characterize and/or isolate a defective mammalian CKR-3 receptor gene, which encodes a receptor having reduced or enhanced activity. Standard methods of screening for a defective gene can be employed, for instance. A defective gene and the activity of the encoded receptor can be isolated and expressed in a suitable host cell for further assessment as described herein for mammalian CKR-3 receptors. A number of human diseases are associated with defects in the function of a G-protein coupled receptor (Clapham, D. E., *Cell*, 75: 1237–1239 (1993); Lefkowitz, R. J., *Nature*, 365: 603–04 (1993)).

The antibodies of the present invention have application in procedures in which receptor can be detected on the surface of cells. The receptor provides a marker of the leukocyte cell types in which it is expressed, particularly in eosinophils. For example, antibodies raised against a receptor protein or peptide can be used to count cells expressing receptor. Cell counts can be used in the diagnosis of a variety of diseases or conditions in which increased or decreased leukocyte cell types (e.g., hypereosinophilia, for example in hypereosinophilic syndrome; hypoeosinophilia) are observed. The presence of an increased level of eosinophils in a sample obtained from an individual can be indicative of eosinophil infiltration due to an inflammatory disease or condition, such as asthma, or an infection such as a parasitic infections. Alternatively, or in addition, the antibodies can be used to sort cells which express receptor from among a mixture of cells. Suitable methods for counting and/or sorting cells can be used for this purpose (e.g., flow cytometry, fluorescence activated cell sorting).

Furthermore, the antibodies can be used to detect or measure decreased or increased expression of receptor in various diseases or conditions in which inflammatory processes of leukocytes are altered (e.g., increased or decreased relative to a suitable control, such as the level of expression in a normal individual). For example, leukocytes (e.g., eosinophils, lymphocytes such as T lymphocytes, monocytes, basophils) can be obtained from an individual and a suitable immunological assay (e.g., ELISA, FACS analysis) can be used to assess the level of expression. The level of expression of a mammalian CKR-3 receptor can be used in the diagnosis of a disease or condition in which increased or decreased expression of a mammalian CKR-3 receptor is present.

Transaenic Animals

Transgenic animals, in which the genome of the animal host is altered using recombinant DNA techniques, can be constructed. In one embodiment, the alteration is not heritable (e.g., somatic cells, such as progenitor cells in bone marrow, are altered). In another embodiment, the alteration is heritable (the germ line is altered). Transgenic animals can be constructed using standard techniques or other suitable methods (see e.g., Cooke. M. P. et al., *Cell*, 65: 281–291 (1991) regarding alteration of T lymphocytes; Hanahan, D., *Science*, 246: 1265–1275, (1989)).

In one aspect, an endogenous mammalian CKR-3 receptor gene can be inactivated or disabled, in whole or in part, in a suitable animal host (e.g., by gene disruption techniques) to produce a transgenic animal. Nucleic acids of the present invention can be used to assess successful construction of a host containing an inactivated or disabled CKR-3 gene (e.g., by Southern hybridization). In addition, successful construction of a host containing an inactivated or disabled CKR-3 gene can be assessed by suitable assays which monitor the function of the encoded receptor.

In another embodiment, a nucleic acid encoding a mammalian CKR-3 receptor protein or polypeptide is introduced into a suitable host to produce a transgenic animal. In a preferred embodiment, endogenous CKR-3 receptor genes present in the transgenic animals are inactivated (e.g., simultaneously with introduction of the nucleic acid by homologous recombination, which disrupts and replaces the endogenous gene). For example, a transgenic animal (e.g., a mouse, guinea pig, sheep) capable of expressing a nucleic acid encoding a mammalian CKR-3 receptor of a different mammalian species (e.g., a human) in leukocytes (such as eosinophils, lymphocytes (e.g., T lymphocytes) can be produced, and provides a convenient animal model for assessing the function of the introduced receptor. In addition, a compound can be administered to the transgenic animal, and the effect of the compound on an inflammatory process mediated by receptor can be monitored in a suitable assay ((see e.g., Weg, V. B. et al., *J. Exp. Med.*, 177: 561 (1993); Abraham, W. M. et al., *J. Clin. Invest.*, 93: 776 (1994)). In this manner, compounds which inhibit or promote receptor function can be identified or assessed for in vivo effect.

Methods of Therapy

Modulation of mammalian CKR-3 receptor function according to the present invention, through the inhibition or promotion of at least one function characteristic of a mammalian CKR-3 receptor, provides an effective and selective way of inhibiting or promoting leukocyte-mediated inflammatory action. One or more ligands, inhibitors and/or promoters of CKR-3 receptor function, such as those identified as described herein, can be used to modulate leukocyte function for therapeutic purposes.

As major eosinophil and lymphocyte chemokine receptors, mammalian CKR-3 receptors provide a target for interfering with or promoting eosinophil and/or lymphocyte function in a mammal, such as a human. Consistently, co-localization of T cells and eosinophils is observed in certain inflammatory infiltrates. Thus, compounds which inhibit or promote CKR-3 receptor function, such as ligands, inhibitors (e.g., 7B11) and promoters identified according to the present method, are particularly useful for modulating eosinophil, basophil, and/or lymphocyte function for therapeutic purposes.

Thus, the present invention provides a method of inhibiting or promoting an inflammatory response in an individual in need of such therapy, comprising administering a compound which inhibits or promotes mammalian CKR-3 receptor function to an individual in need of such therapy.

In one embodiment, a compound which inhibits one or more functions of a mammalian CKR-3 receptor (e.g., a human CKR-3 receptor) is administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

In another embodiment, a compound which promotes one or more functions of a mammalian CKR-3 receptor (e.g., a human CKR-3 receptor) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of CKR-3 receptor function, include, but are not limited to:

- inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis);
- eosinphilic myositis, eosinophilic fasciitis;
- autoimmune diseases, such as rheumatoid arthritis, psoriatic arthritis, multiple sclerosis, systemic lupus erythematosus, myasthenia gravis, juvenile onset diabetes, glomerulonephritis, autoimmune thyroiditis, Behcet's disease;
- graft rejection (e.g., in transplantation), including allograft rejection or graft-versus-host disease;
- cancers with leukocyte infiltration of the skin or organs;
- other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of CKR-3 receptor function, include, but are not limited to:

- immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes;
- infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (fluxes)(Schistosomiasis, Clonorchiasis), cestodes (tape worms)(Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostoma braziliense, Ancylostoma caninum*).

Eosinophils as the Target Cell in Certain Inflammatory Reactions, Particularly Asthma Eosinophils are produced in the bone marrow and circulate to the tissues, predominantly to mucosal tissues, such as the lungs, gastrointestinal tract, and genitourinary tract. Eosinophils typically constitute 1–3% of leukocytes in the blood. However, in people suffering from allergic diseases and helminthic parasitic infections, increased eosinophil accumulation occurs in the tissues or the blood. Eosinophils accumulation can be both beneficial and detrimental to the host.

For example, eosinophils possess numerous granules, containing cationic proteins. Degranulation of eosinophils, triggered, for example, by the engagement of IgG, IgA, or IgE receptors, or by stimulation by inflammatory mediators such as platelet-activating factor (PAF), leukotrienes, or chemokines, leads to release of the components in the granule. Products from eosinophils also cause damage to host cells. The most damaging are the cationic proteins, which are detectable in elevated concentrations in patients with asthma. Eosinophils also generate a number of inflammatory mediators, including Leukotriene C4, and platelet-activating factor (PAF). These mediators contract airway smooth muscle, promote the secretion of mucus, alter vascular permeability, and elicit further eosinophil and neutrophil infiltration.

Eosinophils are involved in the initiation and maintenance of allergic/asthma diathesis. Thus, in a preferred embodiment, the method can be used to treat asthma or hypersensitivity (allergic) states, particularly those involving mucosal tissues, as well as in other eosinophil-associated diseases. In a particularly preferred embodiment, a compound which inhibits one or more function of a mammalian CKR-3 receptor (e.g., a human CKR-3 receptor) is administered to an individual with asthma.

Eosinophils are clearly important in the host defense against and destruction of, large, nonphagocytable organisms, such as multicellular helminthic parasites. Eosinophils are also important effector cells in immune reactions against other pathogens that induce high levels of IgE antibodies. Accordingly, the method can be used to treat infectious diseases, such as parasitic diseases, to stimulate or promote inflammatory defenses, or to suppress inflammatory responses which are destructive to the host.

Eosinophils and Asthma Pathogenesis

Asthma is characterized by the obstruction of the airways or bronchi, and results from a bronchial hyperresponsiveness and rapid constriction in response to a wide range of pharmacological mediators. Chronic inflammation of the bronchial mucosal lining is widely believed to play a fundamental role in the development of asthma.

Intense infiltration of the bronchial mucosa with eosinophils, macrophages and lymphocytes is observed in asthma and other hypersensitivities. Often the selective migration of eosinophils to inflamed airways can be striking, and appears to result from the selective binding of eosinophils to endothelium and extraction from the blood. Eosinophils in particular are implicated as the causative agents of bronchial mucosal injury. Studies of asthmatic patients suggest that blood eosinophil counts correlate with the degree of bronchial hyperresponsiveness. In addition, bronchial biopsies and bronchoalveolar lavage fluid from asthmatics show a clear relationship between the degree of eosinophilia and clinical severity. Thus, there is a strong connection between the presence of eosinophils and adverse immune reactions, particularly in asthma.

A major chemokine receptor on eosinophils and lymphocytes, that functions in selective leukocyte chemotaxis, extravasation and activation in response to chemoattractant, provides an excellent target for interfering with eosinophil recruitment. For example, administration of an inhibitor of at least one function of a mammalian (e.g., human) CKR-3 receptor, such as by inhibiting chemokine binding thereto, can provide an effective and selective way of treating asthma. By reducing or preventing recruitment (extravasation, infiltration) of leukocytes, particularly eosinophils, to inflamed lung and airway tissues, and/or reducing leukocyte function in those tissues, the destructive inflammatory processes of asthma can be inhibited, and the symptoms alleviated.

There is evidence that the blockage of eosinophil recruitment to the lung can alleviate the symptoms of asthma. Administration of a monoclonal antibody reactive with α4 integrin was reported to inhibit the accumulation of eosinophils into the lung and airways, and blocked the airway hyperresponsiveness to antigen challenge in sheep. In a primate model of asthma, a monoclonal antibody to ICAM-1 is reported to attenuate airway eosinophilia and hyperresponsiveness. In addition, in a guinea pig model for passive cutaneous anaphylaxis, in vitro pretreatment of eosinophils with the anti-α4 monoclonal was reported to suppress eosinophil accumulation. (see Wegner, C. D. et al., *Science*, 247: 456 (1990); Weg, V. B. et al., *J. Exp. Med.*, 177: 561 (1993); and Abraham, W. M. et al., *J. Clin. Invest.*, 93: 776 (1994) regarding these models).

Modes of Administration

According to the method, one or more compounds can be administered to the host by an appropriate route, either alone or in combination with another drug. An effective amount of a compound (e.g., a receptor peptide which inhibits ligand binding, an antibody or antibody fragment) is administered. An effective amount is an amount sufficient to achieve the desired therapeutic effect, under the conditions of administration, such as an amount sufficient for inhibition or promotion of a CKR-3 receptor function, and thereby, inhibition or promotion, respectively, of an inflammatory response.

A variety of routes of administration are possible including, but not necessarily limited to oral, dietary, topical, parenteral (e.g., intravenous, intraarterial, intramuscular, subcutaneous injection), inhalation (e.g., intrabronchial, intranasal or oral inhalation, intranasal drops), routes of administration, depending on the disease or condition to be treated. For respiratory allergic diseases such as asthma, inhalation is a preferred mode of administration.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. 1980). For inhalation, the compound can be solubilized and loaded into a suitable dispenser for administration (e.g., an atomizer, nebulizer or pressurized aerosol dispenser).

EXEMPLIFICATION

The present invention will now be illustrated by the following Examples, which are not intended to be limiting in any way.

EXAMPLE 1

Chemotactic Properties of Human Eosinophils

Chemotaxis of Human Eosinophils

To identify antagonists of eosinophilic chemokine receptor(s), it is necessary to identify the important chemokines for eosinophil chemotaxis, and determine the receptor (s) that these chemokines are binding to. Chemotaxis experiments were performed in a sensitive and improved chemotaxis assay, which employs an endothelial cell line grown on the polycarbonate membrane of the chemotaxis well.

Isolation of Eosinophils 100 ml of heparinized blood was diluted 1:1 with PBS. 20 ml aliquots were layered over 65%, 75% Percoll step gradients. The gradients were centrifuged at 1500 rpm, 25 min at room temp. The eosinophil/neutrophil layers were transferred to a new tube and erythrocytes lysed by addition of 20 mls 0.2% NaCl for 1 min followed by the addition of 30 mls 1.8% NaCl. Cells were washed twice with a buffer consisting of PBS, 0.5% BSA, 0.5 mM EDTA. Cells were resuspended at $5\times10^7$ cells/50 μl in cold buffer (PBS, 0.5% BSA, 0.5 mM EDTA) and 50 μl CD16 microbeads were added to the cells. The mixture was incubated at 4° C. for 25 min followed by the addition of 900 μl cold buffer. The miniMACS™ separation unit (Miltenyi Biotec, Inc., Auburn Calif. 95603) was used to deplete CD16 positive cells (neutrophils). Cells were loaded onto the column in 200 μl aliquots. Flow-through cells were collected and assessed histologically. The eosinophil prep was >99% pure.

Chemotaxis Assay

Chemokines were obtained from Peprotech, Inc. (Rocky Hill, N.J.). Chemotaxis experiments were performed using 3.0 micron BIOCOAT cell culture inserts (Collaborative Biomedical Products), in 24 well plates. Endothelial cells were grown to confluency on the inserts for two days prior to chemotaxis experiments. The endothelial cells used were a cell line termed ECV 304 (European Collection of Animal Cell Cultures, Porton Down, Salisbury, U.K.), which expresses endothelial cell markers such as von Willebrand factor, as well as ICAM-1 and VCAM-1. This endothelial cell line greatly facilitates these assays, since human umbilical vein endothelial cells can be variable in nature, can be used for only several passages, and grow much more slowly than ECV 304. The assay was conducted at 37° C. for 1.5 hours, and migrated cells were counted using an inverted microscope.

Results

Figure 4:
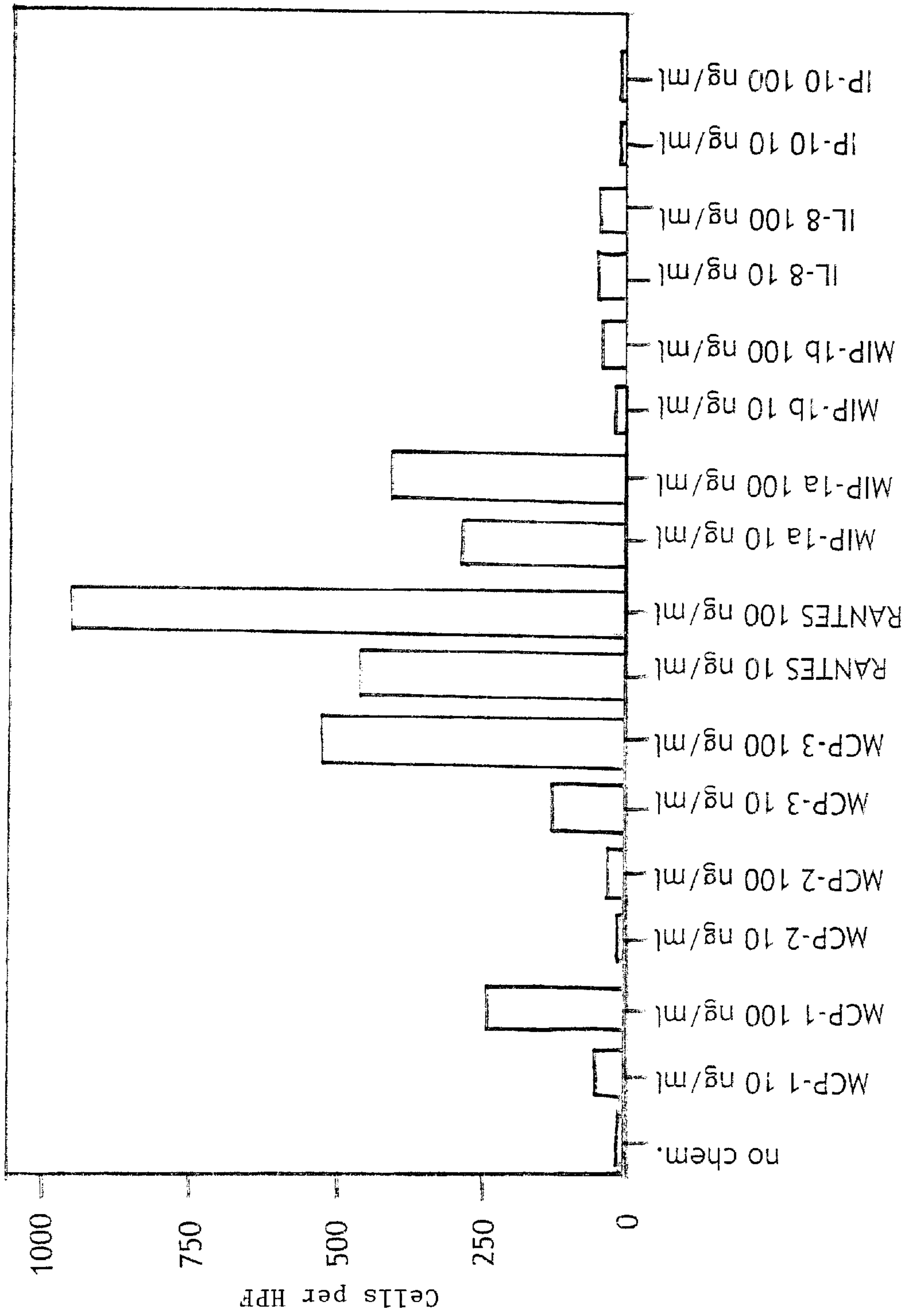
FIG. 4 is a histogram illustrating the chemotaxis of human eosinophils in response to various chemokines. Human eosinophils were purified using a standard protocol, and assessed by microscopy for their response to various chemokines in a 24 well transendothelial chemotaxis assay (cells per high power field (HPF).
Figure 5A:
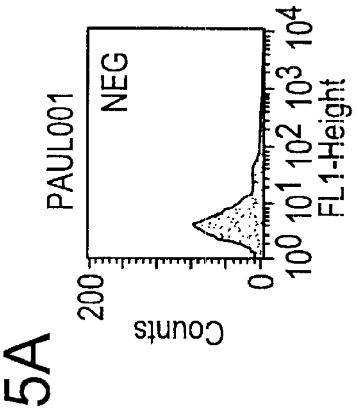
FIGS. 5A–5I are an illustration of a FACS analysis of various clones of L1–2 pre-B cells transfected with Eos L2. Cells from over 200 clones were stained with M2 anti-FLAG Mab followed by anti-mouse Ig-FITC. (Y-axis, number of cells; X-axis, fluorescence). In the negative control (PAUL 001), transfected cells were stained with an irrelevant antibody.
Figure 5B:
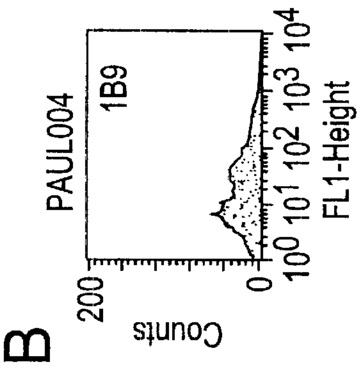
Figure 5C:
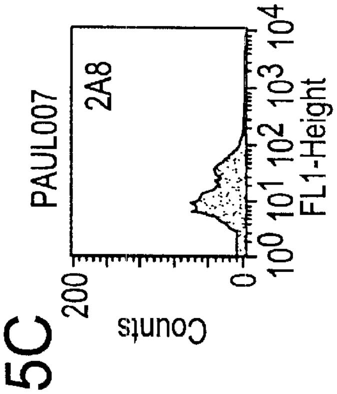
Figure 5D:
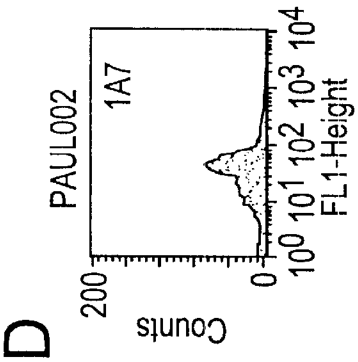
Figure 5E:
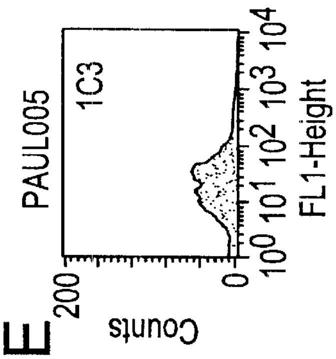
Figure 5F:
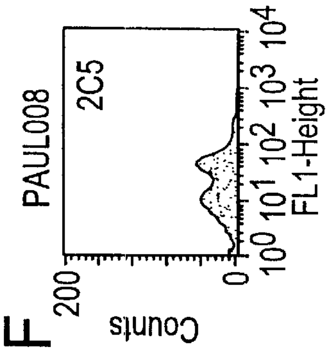
Figure 5G:
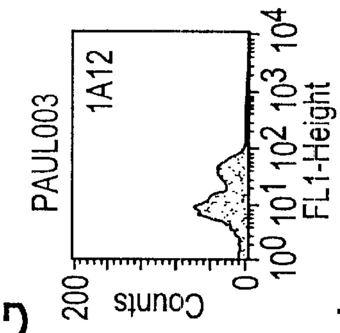
Figure 5H:
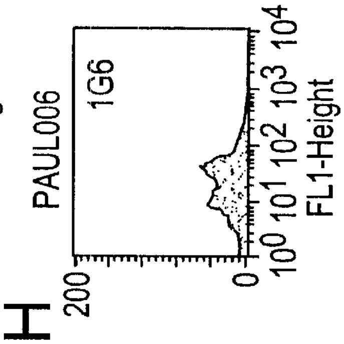
Figure 5I:
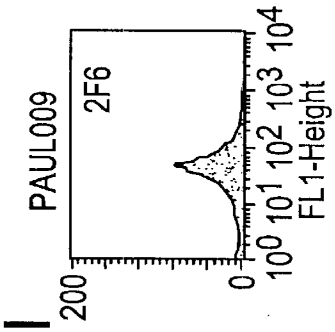

The results, presented in FIG. 4, are representative of at least five experiments. Growth of ECV 304 endothelial cells on the polycarbonate membrane reduced the background migration almost completely. Eosinophils applied to transendothelial chemotaxis assays showed migration to a number of chemokines, particularly RANTES, MCP-3, and to a lesser degree MCP-1. MIP-1β, IL-8, MCP-2, and IP-10 had little effect on eosinophil chemotaxis. MIP-1α was chemotactic for eosinophils in some experiments, although generally was inactive. In these experiments, a range of chemokine concentrations was used, because of the variability in responsiveness of leukocytes to different chemokines, and uncertainties about the quality of chemokine preparations. A consistent finding was the high level of eosinophil chemotaxis to RANTES and MCP-3.

EXAMPLE 2

Identification of a Major Eosinophilic Chemokine Receptor

Primer Selection and Design

Five chemokine receptor genes were aligned and compared to generate a set of degenerate oligonucleotides for use in PCR (Polymerase Chain Reaction) cloning of novel chemokine receptors from eosinophils. The selection of these five receptor genes was based on either the type of chemokine ligand with which they bind (I1-8 receptor A (IL8RA), I1-8 receptor B (IL8RB), MIP-1α receptor (MIP1αR)) or orphan receptors with significant sequence similarity to these receptors whose expression is reported to be restricted to lymphoid cells or tissue (Epstein Barr Inducible receptor-1 (EBI1R) and Burkitt's Lymphoma Receptor-1 (BLR1)). Receptor sequences were aligned by hand based on a number of published alignments (IL-8RA, Holmes et al., *Science*, 253: 1278–1280 (1991); IL-8RB, Murphy, P. A. et al., *Science*, 253: 1280–1283 (1991); MIP1α/RANTES, Neote, K. et al., *Cell*, 72: 415–425 (1991); EBI1R, Birkenbach, M. et al., *J. Virol*., 67: 2209–2220 (1993); and BLR1 (Dobner, T. et al., *Eur. J. Immunol*., 22: 2795–2799 (1992)).

Sequences within transmembrane (TM) regions 2, 6 and 7 as well as a region just C-terminal to TM3 were selected as targets for degenerate oligonucleotide design based on the high degree of sequence similarity. The nucleotide sequences of the degenerate oligonucleotide primers are illustrated in the Table below.

Eosinophil Isolation and Purification 100 ml of heparinated blood was diluted 1:1 with PBS. 20 ml aliquots were layered over 65%, 75% Percoll step gradients. The gradients were centrifuged at 1500 rpm, 25 min at room temperature. The eosinophil/neutrophil layers were transferred to a new tube and erythrocytes lysed by addition of 20 mls 0.2% Nacl for 1 minute followed by the addition of 30 mls 1.8% Nacl. Cells were washed twice with a solution of phosphate buffered saline (PBS), 0.5% Bovine Serum Albumin (BSA), 0.5 mM ethylenediaminetetraacetic acid (EDTA). Cells were resuspended at $5\times10^7$ cells/50 μl in cold buffer (PBS, BSA, EDTA solution), and 50 μl CD16 microbeads were added to the cells. The mixture was incubated at 4° C. for 25 min followed by the addition of 900 μl cold buffer. The MINIMACS separation unit (Miltenyi Biotec, Inc., Auburn, Calif. 95603) was used to deplete CD16 positive cells (neutrophils). Cells were loaded onto the column in 200 μl aliquots. Flow-through cells were collected and assessed histologically. By this criteria, the eosinophil prep was >99% pure.

mRNA isolation and PCR mRNA for RT-PCR (Reverse transcription-polymerase chain reaction) was extracted directly from purified cells using the Micro-FASTTRACK mRNA isolation kit purchased from Invitrogen. Quality of the mRNA was evaluated by PCR amplification of β-actin and/or GAPDH (glyceraldehyde-3-phosphate dehydrogenase) mRNA prior to use with 7TMS degenerate primers.

20–50 ng of mRNA was reverse transcribed using a GENEAMP RNA PCR kit (Perkin-Elmer) with oligo dT and/or random hexamers as primers in a 20 μl final volume as specified by the manufacturer. 2–5 μl of this cDNA (reverse transcribed eosinophil message) was mixed with 200 μM dNTPs and 50–100 pmol of degenerate primers in a 50 μl volume. Magnesium concentration and pH were optimized for each primer pair. The magnesium concentration ranged from 1.0 to 3.0 mM and pH ranged from 8.5 to 10.0. Although various cycle parameters were also evaluated, the conditions generally used were similar to the following: 3 cycles: 94° C., 30 sec; 37° C., 30 sec; 2 min

TABLE

| SEQ ID NO: | Primer Set 2 | |
|---|---|---|
| | TM2a | |
| 7 | Primer 2a-1 (forward) | 5' - TAC CTG CTS AAC CTG GCC ITG GCI G |
| 8 | Nested primer 2a-2 (forward) | 5' - AC CTG GCC ITG GCI GAC CTM CTC TT |
| | TM3 | |
| 9 | Primer 3F (forward) | 5' - GAC CGY TAC CTG GCC ATI GTC CAY GCC |
| 10 | Primer 3R (reverse) | CTG GCR ATG GAC CGG TAI CAG GTR CGG - 5' |
| | TM6b | |
| 11 | Primer 6b-1 (reverse) | GAR AMR ACC IRI GGG ATG TTR IAC CAI - 5' |
| 12 | Nested primer 6b-2 (reverse) | AAG RAI GAR GAR AMR ACC IRI GGG ATG T - 5' |
| | TM7 | |
| 13 | Primer 7-1 (reverse) | ACG SAG TTG GGI IAS IAG ATG CGG AAG - 5' |
| 14 | Nested primer 7-2 (reverse) | GTG WCG ACG SAG TTG GGI IAS IAG A - 5' |

Nucleotide Abbreviations:
K = G/T
M = A/C
R = A/G
S = C/G
W = A/T
Y = C/T ramp to 72° C., 1 min, followed by 30 cycles: 94° C., 45 sec; 48° C., 1 min; 72° C., 1 min. (ramp=gradual increase).

With regard to the 201 bp fragment isolated (see below), primer pairs 2a-1 and 7-1, or primer pairs 2a-1 and 3R, were used in a PCR reaction (as described above) in 60 mM Tris-HCl, pH 9.5 and 1.5 MM $MgCl_2$. One μl of product from each reaction was used in a separate (second) round of PCR with "nested" primers 2a-2 and 3R. ("Nested" primers are primers which hybridize to sequences within the outside primers.) Reaction conditions for the nested PCR were exactly as described for the first PCR.

PCR products were assessed and separated by agarose gel electrophoresis, and appropriately sized fragments were purified and subcloned using the PCR-SCRIPT SK+cloning kit (Stratagene). (Appropriate fragment sizes are as follows: for PCR with primer pairs from regions 2a and 7 (see Table above), ~700 bp; for PCR with primers from region 2a and primer 3R, ~200 bp; for PCR with primer 3F and primers from region 6b, ~400 bp, and for PCR with primer 3F and region 7 primers, ~550 bp.) Expected fragment sizes were predicted based upon the hypothesis that a related receptor protein would share some structural similarity.

Rapid Screening Assay

In order to screen a large number of clones quickly for novel members of the 7TMS family, the inserts of bacterial colonies obtained as described above (i.e., transformants of plasmids comprising appropriately sized fragments subcloned into PCR-SCRIPT SK+plasmid), were screened by PCR using T3 and KS primers complementary to the sequence flanking the polylinker of PCR-SCRIPT plasmid. In particular, a portion of a bacterial colony from an overnight transformation was mixed directly with 40 μl of a PCR mixture containing 200 μM dNTPs, 20 mM Tris, pH 8.5, 50 mM KCl, 2.5 mM $MgCl_2$, 50 pmol each primers and 0.25 units Taq polymerase. Cycle conditions were 25 cycles: 94° C., 20 sec; 55° C., 20 sec; 72° C., 30 sec. Inserts of the correct size were identified by evaluating 20 μl of PCR product on 1.5% agarose gels. The remaining 20 μl of the reaction was digested with Alu I, Hha I, and Rsa I (triple digestion) and resolved on a 12% polyacrylamide gel to screen for different digestion patterns. Clones of different patterns were then selected for sequence analysis.

Results

Sequence analysis of PCR fragment, generated from degenerate oligos, identified a 201 bp partial cDNA clone in PCR-SCRIPT plasmid. (The degenerate oligos were 2a-1, 2a-2, 3F, 3R and 7-1). This partial clone, designated Eos L2 (also referred to as L2 and EL2), was found to have 78.3% amino acid similarity (81.1% nucleic acid similarity) to the MIP1α/RANTES receptor and 60.8% amino acid similarity (61.6% nucleic acid similarity) to the MCP-1 receptor. A search of the most current sequence data bases revealed this partial clone to be unique.

Southern and Northern Analysis

The PCR fragment was labeled and used to probe both Southern and Northern blots. To prepare the PCR probe, the 201 bp fragment was released from the PCR-SCRIPT vector with restriction enzymes EcoRI and Not I. This digested resulted in a fragment of 240 bp comprised of the 201 bp fragment plus 39 base pairs of polylinker from the vector. The fragment was separated from vector by electrophoresis through agarose gel, and purified by Magic Mini Prep (Promega Corp. Madison, Wis.) exactly as recommended by the manufacturer. Approximately 200 ng of material was labeled with the Random Primed DNA Labeling Kit purchased from Boehringer Mannheim following the manufacturer's recommended labeling protocol.

For Southern blots, genomic DNA (purchased from clontech Laboratories, Inc., Palo Alto, Calif.) was digested with restriction enzyme overnight and separated by electrophoresis on a 0.7% agarose gel followed by capillary transfer to HYBOND-N nylon membrane (Amersham). Hybridization was in 6×SSC (1×SSC is 0.15 M sodium chloride, 0.015 M sodium citrate) containing 5×Denhardt's solution (1×Denhardt's solution is 0.02% bovine serum albumin, 0.02% ficoll, 0.02% polyvinylpyrolidone), 10% w/v dextran sulfate, 2% SDS, and sheared salmon sperm DNA (100 μg/ml) overnight at 65° C. The membrane was rinsed twice in 2×SSC, 0.5% SDS at 65° C. followed by two washes (15 min each) in 0.2×SSC, 0.5% SDS at 65° C.

The Southern hybridization revealed a single strongly hybridizing fragment and a single weakly hybridizing fragment with each enzyme used. The weakly hybridizing fragment is likely to be the MIP1α1/RANTES receptor.

Multiple Tissue Northern Blots were purchased from clontech Laboratories, Inc. (Palo Alto, Calif.). EXPRESSHYB Solution was also purchased from clontech Laboratories, Inc. The Multiple Tissue Northern Blots were carried out as recommended by the manufacturer. The probe was as described above for Southern blots. The results of the Northern hybridization showed high levels of a ~1.6 kb message in spleen, peripheral blood leukocytes and thymus. Additional Northern analyses are presented in Example 5.

Genomic Library Screening

A human genomic phage library constructed in the EMBL3 SP6/T7 vector, purchased from CLONTECH Laboratories, Inc. (Palo Alto, Calif.), was screened with the 201 bp PCR fragment to obtain a full-length clone. Approximately 25,000 plaque forming units were mixed with 600 μl of an overnight bacterial culture of *E. coli* strain K802 provided with the library in NZCYM top agarose and plated on 150 mm petri dishes containing NZCYM agar (NZYCM broth, Agar and Agarose were purchased from Gibco/BRL). After incubation at 37° C. for 7 hours, the plates were overlaid with BA-85 nitrocellulose membranes (Schleicher and Schuell, Keene, NH) for 5 minutes to allow transfer of phage to membrane. The membranes were then soaked for 5 minutes in Denturing Solution (1.5 M sodium chloride, 0.5 N sodium hydroxide) followed by neutralization in 1.5 M sodium chloride, 0.5 M Tris, pH 8.0. The filters were allowed to air dry for 15 minutes and then baked for two hours at 80° C. under vacuum. The filters were then hybridized as described above for the Southern Blot. The 201 bp PCR fragment contained the nucleotides between oligonucleotide primers 2a-2 (TM2) and 3R (TM3).

One genomic phage clone, designated Eos L2.8, contained an insert which comprises the 1.8 kb Hind III fragment seen on Southern blots (complete insert size was not determined, but is ~17 kb).

Phage clone Eos L2.8 was digested with Hind III restriction enzyme and electrophoresed on an agarose gel. A Hind III fragment of approximately 1.8 kb was cut out, electroeluted from agarose, phenol/chloroform extracted and precipitated with ethanol. The 1.8 kb fragment was resuspended in water and ligated into the Hind III site of the PBLUESCRIPT II KS+vector (Stratagene) followed by transformation into DH5α competent cells purchased from Gibco/BRL.

Both strands of this Hind III fragment were sequenced, and the fragment was found to contain the entire amino acid coding region for the Eos L2 receptor (a human CKR-3 receptor). Comparison of this sequence and the cDNA clone described below indicates that the clone is a full-length clone. The open reading frame of 1065 nucleotides encodes a protein of 355 amino acids (SEQ ID NO:2) with a predicted molecular mass of 41 Kd.

Comparison of the sequence of the full-length Eos L2 receptor with MIP1α/RANTES and MCP-1 receptors revealed a 73.4% and 60.5% amino acid similarity, respectively. For this comparison, sequences were aligned by hand and the number of similar amino acids, divided by the total number of amino acids was multiplied by 100.)

The sequences were also aligned by the Clustal method using MEGALIGN software (DNASTAR, Inc.). Comparison with other chemokine receptor sequences revealed a 62%, 47%, and 41% amino acid sequence similarity to CKR-1, CKR-2B, and CKR-4, respectively. In contrast, the amino acid sequence similarity to IL-8 receptors A and B was only 27% for both receptors. The sequence similarity of this receptor to MIP1 α/RANTES and MCP-1 receptors, both C—C chemokine receptors, is consistent with the results reported herein which indicate that Eos L2 is a C—C chemokine receptor.

EXAMPLE 3

Expression of Eos L2 in Transfected Cell Lines

FLAG-tagged Eos L2 (CKR-3) Receptor construct

An Eos L2 receptor fusion protein was constructed as follows:

1. A FLAG-PAF receptor construct in pCDM8 (constructed as reported in Kunz, D. et al., *J. Biol. Chem.*, 267: 9101–9106 (1992)) was double digested with Hind III and EcoRI to release a 48 bp fragment containing nucleotides which encode the FLAG peptide. The nucleotide sequence is AAGCTTCCA GCA GCC ATG GAC TAC AAG GAC GAC GAT GAC AAA GAATTC (SEQ ID NO:15). The amino acid sequence is MDYKDDDDKEF (SEQ ID NO:16). The 48 bp Hind III/EcoRI fragment containing the FLAG nucleotides subcloned into the HindIII/EcoRI sites of the pcDNA3 vector (Invitrogen, San Diego, Calif.) giving rise to pcDNA3/FLAG.

2. The PBLUESCRIPT II KS+vector containing the 1.8 kb Eos L2 Hind III fragment was digested with BamHI and Xho I to release a 1.261 kb fragment. This BamHI-XhoI fragment contains nucleotides encoding Eos L2 amino acids 91 through the stop codon plus the same 3' untranslated region and 21 bp of PBLUESCRIPT II KS+vector.

3. Two PCR primers were generated to amplify the 5' end of the Eos L2 gene, but removing the first Met and engineering in an EcoRI site which will be compatible with the EcoRI site described above in step 1. The 5' primer (SEQ ID NO:17) was:

EcoRI

5'-TTAA GAATTC ACA ACC TCA CTA GAT AC

This primer contains an EcoRI site and the first 17 nucleotides of the EosL2 gene except for the Met codon.

The 3' primer (SEQ ID NO:18) was:

```
BamHI
5'-CATAGT GGATCC AGAATG
```

This primer primes in the Eos L2 gene just 3' to the BamHI site. Amplification with these two primers using the PBLUESCRIPT II KS+vector containing the 1.8 kb Eos L2 fragment as template will amplify a 280 bp fragment containing the 5' end of the Eos L2 which can be digested with EcoRI and BamHI to give a fragment for ligation as described below.

Conditions for amplification were: 100 ng of PBLUESCRIPT II KS+vector containing the 1.8kb EosL2 fragment was combined with 200 μM dNTPs and 50 pmol of primers in a 50 μl reaction volume. The final magnesium concentration was 2.5 μM and the pH was 8.0. The fragment was amplified with 25 cycles of 94° C., 30 sec; 55° C., 30 sec; 72° C., 30 sec. The amplified product was separated on agarose gel and purified by electroelution as described above. The fragment was digested with EcoRI and BamHI purified again on agarose gel.

4. For construction of the Flag-tagged EosL2 gene, the pcDNA3 vector containing the FLAG fragment (described in step 1) was digested with EcoRI and Xho I. The vector fragment (an EcoRI-XhoI fragment comprising the FLAG coding sequence) was separated from the polylinker fragment by electrophoresis, and the vector fragment was purified as described for other electroeluted fragments. The vector fragment was combined with the EcoRI-BamHI fragment generated by PCR in step three. These two fragments were combined with the 1.261 kb BamHI-XhoI fragment from step two. All three fragments were triple ligated together to yield the FLAG-tagged Eos L2 receptor in pcDNA3. Ligated DNA was transformed into DH5α.

Transient Transfectants 293 cells (ATCC Accession No. CRL 1573) were grown in Minimal Essential Medium (MEM) Alpha Medium obtained from Gibco/BRL and supplemented with 10% fetal Calf Serum, Glutamine, and Penicillin/Streptomycin (all from Gibco/BRL). For each transient transfection, $2\times10^6$ 293 cells were plated 1 day before transfection in a 35-mm tissue culture dish. On the day of transfection, the cells (which grow attached to the dish) were washed 1× with Phosphate Buffered Saline (PBS, Gibco/BRL) and a mixture of DNA and LIPOFECTAMINE Reagent liposomes (Gibco/BRL) were applied to the cells.

The DNA/LIPOFECTAMINE reagent liposome mixture was made by incubating 2 μg of Flag-tagged Eos L2 receptor expression vector in a final volume of 100 μl OPTIMEM cell culture media (Gibco/BRL) with 12 μl of LIPOFECTAMINE reagent liposomes in a 100 μl volume for 45 minutes at room temp. The final mixture volume is 200 μl. After the 45 minute incubation, 800 μl of OPTIMEM cell culture media is added to the 200 μl of DNA/LIPOFECTAMINE reagent liposomes and the 1 ml of solution is layered over the cells as described above. The cells were then incubated at 37° C. for 5 hours at which time 1 ml of MEM Alpha Medium supplemented as described above is added. The cells are incubated for an additional 12 hours at which time all medium is removed and the cells washed 2× with PBS and 2 mls of MEM Alpha medium supplemented as described above is added. The transfected cells are then incubated for an additional 72 hours. The cells are harvested by gently pipetting them after incubation in PBS 10 mM EDTA.

Cell surface expression of a FLAG-tagged Eos L2 receptor was demonstrated in the transiently transfected 293 cells. Approximately 2.6% of the cells express the receptor on the surface as determined by immunofluorescent staining and FACS analysis. Levels of expression in some cells were found to be as much as 2 logs greater than background indicating that high levels of expression can be achieved in this cell line. As the Eos L2 gene is carried by the pcDNA3 expression vector (Invitrogen Corp., San Diego, Calif.), which contains the neomycin resistance gene, stable 293 transfectants can be selected using geneticin (G418) selection.

Stable Cell Lines

Over 500 stable lines of mouse L1-2 pre-B cells have been generated with the FLAG-tagged receptor. L1-2 pre-B cells were obtained from (Dr. Eugene Butcher, Stanford University, Stanford, Calif.), and were maintained in RPMI-1640 (Gibco/BRL), supplemented with 10% bovine serum albumin, and Pen/Strep, sodium pyrvate and β-mercaptoethanol. Cells from over 200 clones were screened for surface expression by staining with M2 anti-FLAG monoclonal antibody (International Biotechnologies, Inc., New Haven, Conn.), followed by anti-mouse Ig-FITC (Jackson ImmunoResearch Laboratories, Inc.), and analyzed by fluorescence activated cell sorting (FACS). Immunofluorescent staining and FACS analysis was performed as described in Current Protocols in Immunology, Vol. 1, Coligan, J. et al., Eds., (John Wiley & Sons, Inc.; New York, N.Y.). Results of the FACS analysis for several cell lines revealed a number of clones which express high levels of the Eos L2 flagged receptor (FIG. 5). Untransfected cells (not shown) were negative for staining. Stable cell lines with high level expression can be used as immunogens for the production of antibodies reactive with the Eos L2 receptor. In addition, these cell lines are useful for studying chemotaxis and ligand binding.

Baculovirus Expression

For construction of a baculovirus expression vector, the Flag-tagged Eos L2 receptor in pcDNA 3 was digested with Hind III to remove the Flag-tagged gene. The HindIII fragment containing the gene was blunt ended by filling in the overhangs with Klenow fragment and dNTP's. The blunt ended fragment was subcloned into the Sma I site of pVL1393 (Invitrogen). 2.0 μg of the pVL1393 vector containing the Eos L2 gene was mixed with 0.5 μg of AcMNPV viral DNA (Invitrogen) and co-transfected into Sf9 insect cells (Invitrogen) with INSECTIN liposomes (Invitrogen) according to the manufacturer's instructions. The SF-900 media (serum free) was replaced with 5 ml of SF-9 culture medium (Grace's Supplemented Insect Media (Gibco/BRL) containing 10% fetal calf serum) on the following day, and the cells were allowed to grow for five days. Recombinant virus was plaque purified as described in D. R. O'Reilly, L. K. Miller, and V. A. Luckow (1994) Baculovirus expression vectors: A Laboratory Manual, Oxford University Press, pp. 149–158.

Expression of the Eos L2 receptor was obtained on Sf9 cells by infecting Sf9 cells with the plaque purified recombinant virus described above. The Sf9 cells ($2\times10^6$ cells/ml) were infected at a multiplicity of infection of 10:1. The infection proceeded for 72 hours at which time the cells were stained with the M2 anti-FLAG antibody.

Successful expression of this receptor was also achieved with a baculovirus expression system in Sf9 cells. Good levels of expression have been achieved based on staining with anti-FLAG antibody (see Example 5). Ligand binding was also achieved with the same cells Sf9 transfectants shown by FACS to be expressing receptor. While definitive cell surface expression was shown by propidium iodide exclusion, expression on these cells appeared to be low, as compared with a negative control (i.e., Sf9 cells transfected with expression vector lacking the Eos L2 gene insert). Length of infection can be decreased, and MOI can be further optimized, for higher cell surface expression.

EXAMPLE 4

Ligand Binding Studies

Ligand Binding Procedure

Cells transfected with Eos L2 receptors or normal human eosinophils purified (see above) were washed in Hanks Balanced Saline Solution (HBSS), then resuspended in binding buffer: 50 mM HEPES, 1 mM $CaCl_2$, 5 mM $MgCl_2$, 0.5% Bovine Serum Albumin (BSA), pH 7.3. In microfuge tubes, $5\times10^5$ cells were incubated with 0.1 nM radiolabeled chemokine (purchased from New England Nuclear, Massachusetts) in 200 μl aliquots at room temperature for 60 minutes. The cells were either incubated with radiolabeled chemokine alone, or together with unlabeled chemokines (from PeproTech) as competitors, which were used at the indicated concentrations. At the end of incubation, cells were washed 3 times in the binding buffer, each wash consisting of centrifugation in a microfuge at 7,000×g for 2 minutes. After the wash, the pellets were transferred into LP3 tubes and the radioactivity of the cells, which represented the amount of binding was measured in a gamma counter. All samples were in duplicates and all the experiments were repeated at least 3 times. Scatchard Plot was calculated from the binding data by MICROSOFT Excel and CricketGraph software on a MACINTOSH computer.

Binding to Human Eosinophils

Based on the findings from chemotaxis assays (see Example 1), the ligand binding studies focused on RANTES, MIP-1α and MCP-3. The ligand binding studies were carried out using radiolabeled chemokines and various 'cold' chemokines as competitors. Purified normal human eosinophils were incubated with either 0.1 nM $^{125}$I-labeled MIP-1α or RANTES in the presence or absence of various cold chemokines (250 nM MIP1α, RANTES, IL-8, MCP-1 or MCP-3). After extensively washing the cells, the binding was measured by a gamma counter.

Figure 6:
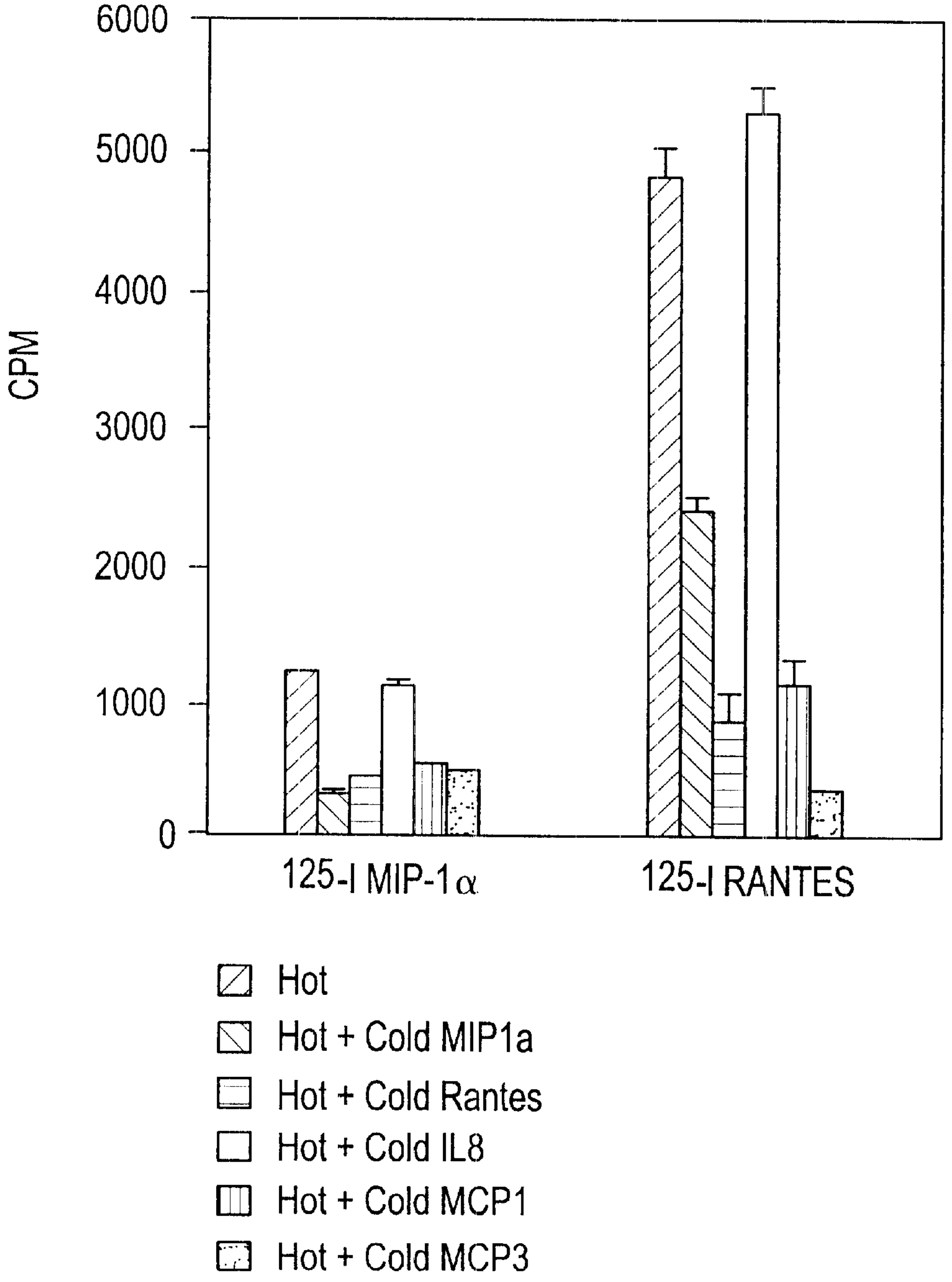
FIG. 6 is a histogram illustrating the binding of RANTES and MIP-1$\alpha$ to human eosinophils. Purified normal human eosinophils were incubated with 0.1 nM $^{125}$I-labeled MIP-1$\alpha$ or RANTES ("Hot") in the presence or absence of various cold chemokines (MIP-1$\alpha$, RANTES, IL-8, MCP-1, MCP-3) at 250 nM.
Figure 7:
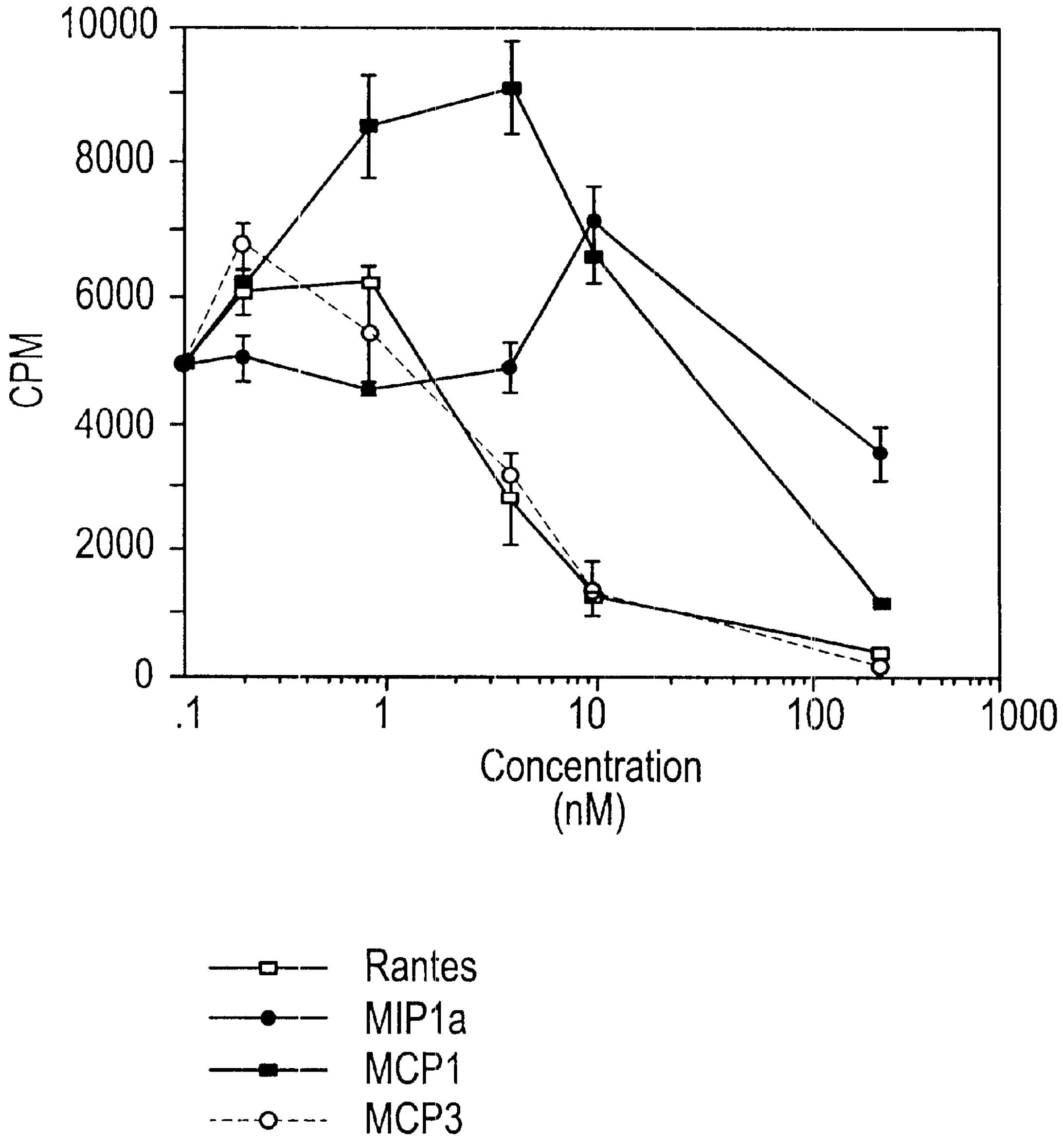
FIG. 7 is a graph illustrating inhibition of the binding of $^{125}$I-labeled RANTES to human eosinophils by various cold chemokines (RANTES, MIP-1$\alpha$, MCP-1 and MCP-3). Human eosinophils were incubated with 0.1 nM radiolabeled RANTES and the indicated concentrations of cold chemokines. The data plotted are the means and standard deviations of duplicates for each sample.

FIG. 6 is a histogram illustrating the binding of human eosinophils to RANTES and MIP-1α. These results suggest that eosinophils bind only weakly to MIP-1α, and that this binding can be inhibited by MIP-1α itself and by other δ-family chemokines, e.g., MCP-1, MCP-3 and RANTES (FIG. 6). In contrast, eosinophils bound RANTES more abundantly (FIG. 6). Binding by RANTES could not be inhibited efficiently by excess amount of 'cold' MIP-1α (FIG. 7), suggesting that on eosinophils, there could be distinguished receptors for MIP-1α and RANTES.

Scatchard plot analysis revealed that there are $1.8\times10^3$ MIP-1α binding sites with an affinity of 91 pM. The analysis also revealed a lower affinity (883 pM) receptor for RANTES, having more binding sites ($3.6\times10^4$/cell). Under the conditions used, there was no significant MCP-1 binding to eosinophils (not shown), and MCP-1 did not inhibit RANTES binding except at very high concentrations (2500-fold excess, FIG. 7).

Eos L2 Receptor Transfectants

Figure 8:
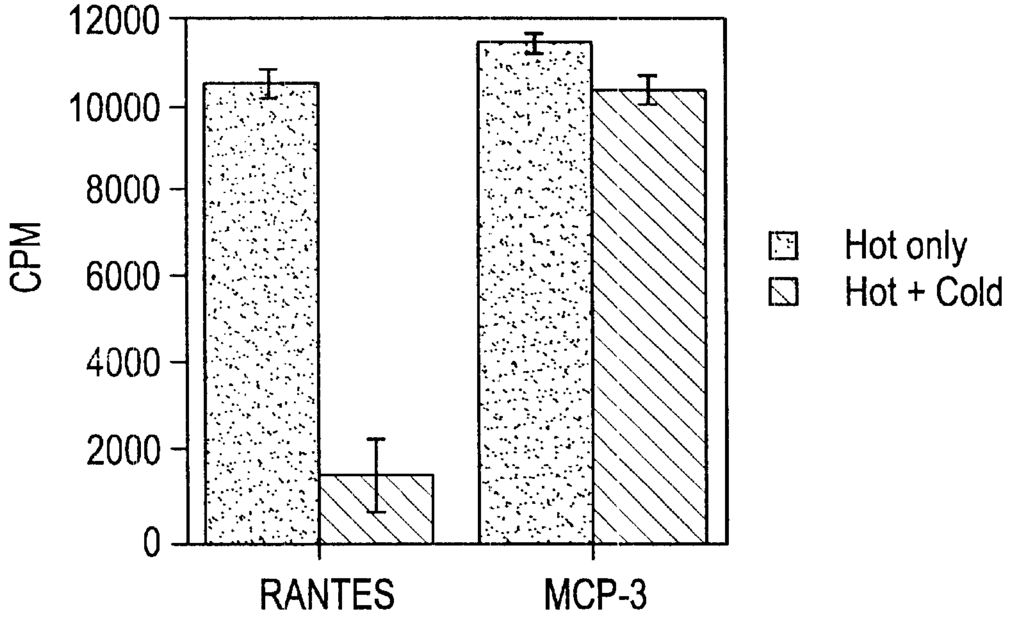
FIG. 8 is a histogram illustrating the binding of 0.1 nM $^{125}$I-labeled ("hot") RANTES or 0.1 nM $^{125}$I-labeled ("hot") MCP-3 to Eos L2 infected SF9 cells (cpm, counts per minute). (From left to right: Hot Rantes only; Hot Rantes+Cold Rantes; Hot MCP-3 only; Hot MCP-3+cold MCP-3).

Following the cloning and expression of the Eos L2 receptor, transfected cells were used to test binding to a number of chemokines. The first attempts using 293 transfectants were unsuccessful, as the addition of cold chemokines interfered with binding, a phenomenon observed by other investigators. In contrast, using baculovirus infected SF9 cells, good RANTES binding could be detected (FIG. 8). The assay conditions for SF9 cells were different from that of mammalian cells. Binding of 0.1 nM $^{125}$I-labeled RANTES took place in 50 mM HEPES, pH 7.3, 5 mM $MgCl_2$ and 1 mM $CaCl_2$, supplemented with 0.5% BSA. After 60 minutes at room temperature, the cells were washed three times in the binding buffer containing 0.5 M NaCl, and the radioactivity in the cell pellets was counted using a gamma counter.

In these ligand binding assays, the most effective heterologous competitor of MIP-1α or RANTES binding was MCP-3. In fact, MCP-3 also effectively inhibited MCP-1 binding to activated T cells. Thus, MCP-3 appears to bind to CKR-1, CKR-2 and CKR-3 (CKR-1, Gao, J. L., et al., *J. Exp. Med.*, 177: 1421–1427 (1993) and Neote, K., et al.,

*Cell*, 72: 415–425 (1993); CKR-2, Charo, I. F., et al., *Proc. Natl. Acad. Sci. USA*, 91: 2752–2756 (1994) and Myers, S. J., et al., *J. Biol. Chem.*, 270: 5786–5792 (1995)).

Radiolabeled MCP-3 (Peprotech, Inc. Rocky Hill, N.J.) was also used for binding studies. MCP-3 binding was carried out as described above with the following modifications. Cells were incubated with 0.1 nM $^{125}$I-labeled MCP-3. The binding buffer used was HBSS plus 0.5% BSA and 0.1% sodium azide. Binding took place at 37° C. for 30 min. The unbound isotope was separated by spinning cells through 800 μl of 20% sucrose, at 12,000×g for 2 min. The tubes were then snap-frozen in dry ice, the tips cut off with a pair of pliers and counted.

EXAMPLE 5

Expression of the Eosinophilic Chemokine Receptor

To confirm that the Eos L2 receptor is the functional receptor on eosinophils, the expression of the receptor was assessed by (a) Northern blot analyses, and (b) flow cytometry using monoclonal antibodies anti-peptide antibodies reactive with the receptor.

Purification of Human Eosinophils, Neutrophils, and PBMC

Eosinophils were isolated from heparinized blood of individuals with high levels of circulating blood eosinophils (5–17%) by combined density gradient centrifugation and negative selection with anti-CD16 magnetic beads (Hansel, T. T. et al., *J. Immunol. Meth.*, 122: 97 (1989)). Briefly, the granulocyte fraction from the Percoll centrifugation was incubeated with CD16 microbeads (Miltenyi Biotec, Inc., Sunnyvale, Calif.) for 30 minutes. Cells were then passed through a MACS column (Miltenyi Biotec, Inc.), and eosinophils were collected in the flow-through. Eosinophils were shown histologically to be >99% pure as determined by analysis of Diff-Quick-stained cytocentrifugation preparations by light microscopy.

Human neutrophils were isolated from heparinized venous blood by Percoll density gradient centrifugation (δ=1.088) at room temperature (Coligan et al., Eds., 1992, *Current Protocols in Immunology*, (John Wiley & Sons: New York, N.Y.)). RBCs were removed by hypotonic lysis.

PBMCs were also isolated as described (Coligan et al., Eds., 1992, *Current Protocols in Immunology*, (John Wiley & Sons: New York, N.Y.)). Monocytes were purified by CD14 positive selection with magnetic beads and T cells were purified by passage of lymphocytes over nylon wool. To generate CD3 blasts, 2×10$^6$ PBMCs/ml in RPMI-1640 plus 10% FCS were added to tissue culture plates first coated with the anti-CD3 antibody TR77. After 4–6 days blasts were removed to fresh media and supplemented with IL-2 (Genzyme) at 50 units/ml.

Northern Analyses: CKR-3 is Expressed Selectively in Eosinophils

Although eotaxin is a selective chemoattractant for eosinophils, the CKR-3 receptor also binds RANTES and MCP-3, which are known to attract monocytes and T cells. Message expression of the receptor was examined in various leukocyte populations.

The results of initial Northern hybridization (see Example 2) showed expression of a ~1.6 kb message in spleen, peripheral blood leukocytes, and thymus, and a number of leukocyte subpopulations, such as eosinophils and T cells, as well as in the HL-60 cell line. Message levels increased dramatically in the HL-60 cell line upon butyric acid induction down the eosinophilic pathway.

This message is likely to be that of Eos L2, since the message for the MIP1α/RANTES receptor which cross-hybridizes on Southern blots is weak and is reported to be approximately 3.0 kb. When the original 201 bp PCR fragment is used as a probe in Southern blots, a strongly hybridizing 1.8 kb HindIII fragment is seen. This is the fragment that was cloned and discussed here. In addition to this fragment, a very weakly hybridizing fragment at about 10 kb is observed. This 10 kb fragment corresponds to the reported HindIII fragment size of the MIP1α/RANTES receptor. This MIP1α/RANTES receptor produces a message of approximately 3 kb which is not observed on Northerns. Therefore, the ~1.6 kb message seen on Northerns probably derives from Eos L2 gene. By far the most abundant expression of Eos L2 was observed in a preparation of purified eosinophils from a patient with hypereosinophilic syndrome (see Example 8).

Because of the high sequence similarity of CKR-3 to other CC chemokine receptors and the fact that the full-length clone hybridizes to multiple sequences in Southern blots, additional Northern analyses used a 250 bp fragment from the 3'-untranslated region of the genomic clone which does not cross-hybridize with other sequences in Southern blots. For hybridization, a 3'-untranslated region probe specific for CKR-3 was used encompassing nucleotides 1203–1453 (FIG. 1*c*).

A Northern blot panel was prepared using RNA from different leukocyte populations, including monocytes, neutrophils, lymphocytes, T cells, T cell blasts produced by activation with CD3 MAb, and eosinophils. RNA was isolated using TRIZOL reagent (Gibco/BRL) following the manufacturer's recommended protocol. 15 μg of total RNA isolated from each highly purified leukocyte population was separated on 1.2% formaldehyde agarose gels and transferred to NYTRAN-PLUS nylon membrane (Schleicher and Schuell) and cross-linked using a STRATALINKER uv crosslinker. Hybridization with radiolabeled 3'-untranslated region probe was with EXPRESSHYB Solution (clontech) using the manufacterer's suggested protocol. Northern blots were exposed to X-OMAT AR film for 3–5 days with intensifying screen. CKR-3 specific probe was removed by boiling in 0.5% SDS and the blot re-probed with β-actin to control for variation in loading.

The only cell population which gave a detectable signal was eosinophils, where a message 1.8 kb in size was found. These results are consistent with the pattern of surface expression detected immunologically in FIGS. 13A–13D. Although message was not detected in resting or activated T cells in this experiment, it is possible that a subset of T cells may express the receptor.

Monoclonal Antibodies (MAbs) Reactive with the Eosinophilic Chemokine Receptor

MAbs reactive with the Eos L2 receptor were generated by immunizing mice with a synthetic peptide corresponding to the N-terminal 35 amino acids. The N-terminal 35 amino acids of Eos L2, deduced from the nucleotide sequence (see FIGS. 1A–1D; see also, SEQ ID NO:2), were synthesized and coupled to the carrier protein PPD (Purified Protein Derivative of *Mycobacterium tuberculosis*; Severn Biotech Ltd., Cambridge, U.K.).

Female Balb/C mice were immunized with 50 μg of this peptide peptide-carrier conjugate in PBS 4 times at 2 week intervals. Mice were injected intra-peritoneally with the peptide conjugate, using Freund's complete (first injection) and incomplete adjuvant (subsequent injections). The final immunization was injected intravenously without adjuvant. Polyclonal antiserum was also collected from mice immunized with synthetic peptide.

Two successful fusions were performed which generated over 15,000 hybridomas. Four days after the final injection, the spleen was removed and a single cell suspension prepared in serum free DMEM media. These cells were fused with the hybridoma fusion partner SP2/0, according to Galfre, G. et al. (Galfre, G. et al., *Nature*, 266: 550–552 (1977)). 20 ml of spleen cells and 20 ml of SP2/0 were combined, spun at 800 g for 5 min and the media removed. A solution of 50% Polyethylene glycol 1500 (Boehringer Mannheim, Indianapolis, Ind.) prewarmed to 37° C. was added to the cell pellet over 2 min, followed by 10 ml of DMEM media over 3 min. The cell suspension was spun at 400 g for 3 min and the supernatant removed. The pellet was resuspended gently in DMEM media containing 20% fetal calf serum, 2 mM L-glutamine, 100 units/ml penicillin, 100 $\mu$g/ml streptomycin sulfate, and HAT selection media (Boehringer Mannheim, Indianapolis, Ind.). Cells were plated into 96 well flat bottom microtiter plates at 200 $\mu$l/well.

10–14 days later, supernatants from the wells were screened for reactivity against the peptide using an enzyme-labeled anti-mouse antibody (Horseradish peroxidase-labeled anti-mouse IgG (Jackson) in an ELISA assay. Approximately 200 mAbs were selected that showed strong reactivity against the synthetic peptide. Hybridomas of interest were subcloned using limiting dilution.

To determine which antibodies could recognize the native, surface expressed molecule, the MAbs were screened against Sf9 insect cells infected with AcMNPV virus carrying human Eos L2 genomic DNA. These insect cells expressed Eos L2 (CKR-3) receptor on the cell surface, as judged by strong anti-FLAG staining of approximately 10% of cells. Staining was performed using M2 anti-FLAG antibody, followed by anti-mouse Ig-FITC (Jackson ImmunoResearch Laboratories, Inc.), and analyzed by flourescence activated cell sorting, using FACSCAN flow cytometer analysis to quantitate expression. (Current Protocols in Immunology, Vol. 1, Coligan, J. et al., Eds., (John Wiley & Sons, Inc.; New York, N.Y.).

Approximately 33% of the anti-peptide hybridomas reacted with the Eos L2 transfected insect cells, with a staining pattern identical to that of the FLAG antibody, as determined by FACS analysis using anti-mouse Ig-FITC (Jackson ImmunoResearch Laboratories, Inc.) as second antibody. Untransfected insect cells stained with anti-FLAG were completely negative. Anti-peptide antibody also tested against untransfected cells, which were negative for staining.

MAbs that were found to stain the transfected insect cells were examined using FACS analysis for their reactivity with human eosinophils, peripheral blood lymphocytes, monocytes, neutrophils, and activated T cells (activated T cells; lymphocytes were treated with an anti-CD3 antibody to activate T cells). Cells were stained with mAb LS26-5H12 and then FITC-anti-mouse Ig (Jackson ImmunoResearch Laboratories, Inc.). Fc receptor binding was controlled for by using an excess of normal human serum.

All eosinophils were stained with a selected anti-Eos L2 mAb, LS26-5H12. Neutrophils were not significantly stained by LS26-5H12 antibody under the conditions of the assay. Based on the expected distribution of the Eos L2 receptor, and that it functions in RANTES binding, MAb LS26-5H12 appears to recognize the naturally expressed form of this receptor. In addition to the LS26-5H12 MAb, ~five additional Mabs behaved similarly.

The LS26-5H12 hybridoma was further purified by limiting dilution. In another experiment, highly purified leukocyte subsets (purified as described in Example 5) were stained with MAb LS26-5H12 and analyzed by flow cytometry (FIGS. 9A–9D). Staining profiles were representative of at least 4 experiments. T Cells were identified based on CD3 staining. Monocytes and neutrophils were identified by forward and side scatter.

Figure 9A:
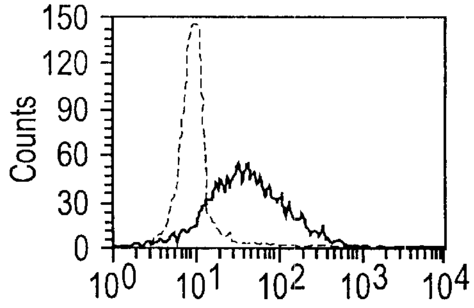
FIGS. 9A–9D are graphs illustrating CKR-3 expression on leukocytes as determined using MAb LS26-5H12 and flow cytometry. Leukocyte subsets were stained with anti-CKR-3 MAb LS26-5H12 (solid lines) or an $IgG_1$ isotype-matched control antibody (MOPC-21) (dotted lines).
Figure 9B:
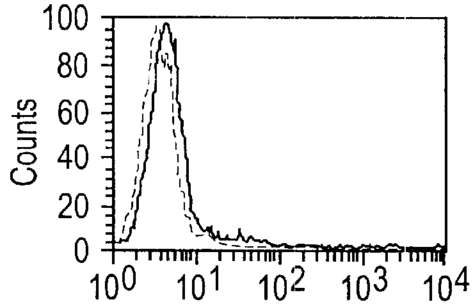
Figure 9C:
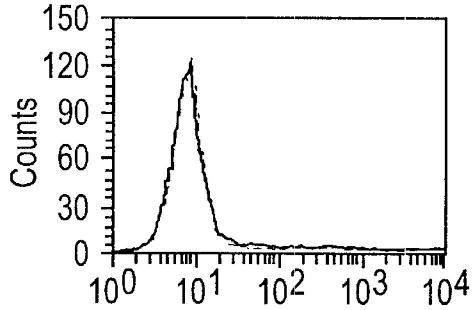
Figure 9D:
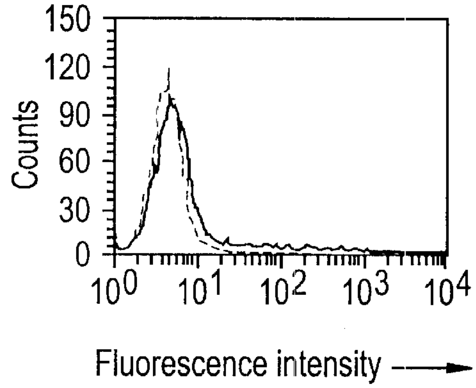

Highly purified eosinophils stained strongly with LS26-5H12 (FIG. 9A), suggesting abundant expression of the receptor on the surface of eosinophils, and consistent with a high receptor number determined by ligand binding and Scatchard analysis. Neutrophils, blood T cells, and monocytes showed little or no staining with this MAb (FIGS. 9B–9D). These latter results, using antibody from the recloned hybridoma, suggest CKR-3 is selectively expressed on eosinophils, and is not appreciably expressed on other leukocyte types tested. However, it is possible that a subset of T cells expresses the receptor.

EXAMPLE 6

Selection of Stable L1.2 Cell Transfectants

2%–5% of transiently transfected COS, HEK-293 and CHO cells were surface positive as assessed using antibodies to FLAG-tagged receptor (see above), while substantial intracellular protein could be detected, suggesting inefficient protein trafficking. The L1.2 mouse pre-B cell line was used to select lines with higher levels of surface expression (see FIGS. 5A–5I) for further assessment of ligand binding specificity and signal transduction by CKR-3. This cell line has been used successfully for the study of other chemoattractant receptors (Honda, S., et al., *J. Immunol*., 152: 4026–4035 (1994)), and the expression of transfected human chemokine receptors confers specific chemotactic ability to various ligands (see below).

To monitor surface expression of CKR-3, a monoclonal antibody (MAb) was produced to the N-terminal region of the receptor, by immunizing mice with a synthetic peptide having a sequence corresponding to the N-terminal 35 amino acids of CKR-3. Anti-peptide MAbs were detected by ELISA, and MAbs that recognize the native receptor were identified by their reactivity with human eosinophils, as well as their staining of transient transfectants.

Construction of CKR-3/pcDNA3

PCR was used to modify the CKR-3 gene contained in the 1.8 kb genomic fragment by inserting a HindIII restriction site and optimal Kozak sequence immediately 5' to the initiation codon. The coding region and 448 bp of 3'-untranslated region were inserted into the HindIII site of pcDNA3 (Invitrogen), placing the gene under the control of the human CMV immediate early gene promoter of the vector. The details of the construction of this FLAG-tagged Eos L2 (CKR-3) receptor construct (also referred to herein as CKR-3/pcDNA3) are provided in Example 3.

Transfection and Stable Cell Line Selection

The murine pre-B lymphoma cell line L1.2 was obtained from Dr. Eugene Butcher (Stanford University) and maintained in RPMI-1640 supplemented with 10% bovine serum. 20 μg of linearized, CKR-3/pcDNA3 was used to transfect the cell line as follows. L1.2 cells were washed twice in HBSS and resuspended in 0.8 ml of the same. The plasmid DNA was mixed with the cells and incubated for 10 minutes at room temperature then transferred to a 0.4 cm electroporation cuvette and a single pulse applied at 250 V, 960 μF. The electroporation was followed by a 10 minute incubation at room temperature. G418 was added to a final concentration of 0.8 mg/ml 48 hr post-transfection and the cells plated in 96 well plates at 25,000 cells/well. After 2–3 weeks under drug selection, G418 resistant cells were stained with 5H12 anti-receptor mAb (see below) and analyzed by FACSCAN flow cytometer analysis.

Lines with detectable surface staining were expanded and cloned several times by limiting dilution. Clones with the brightest surface staining were further analyzed by Northern hybridization to confirm the presence of transfected receptor as well as by RT-PCR using a T7 primer complementary to the pcDNA3 vector as the 5' primer and a CKR-3 specific primer as the 3' primer (not shown). No amplification was seen without addition of reverse transcriptase.

For transient transfection, 20 μg of supercoiled DNA was used in the electroporation exactly as described for stable cell line production. Cell surface staining was assessed after 48–72 hrs.

L1.2 cells transfected with CKR-3/pcDNA3 were diluted to $1\times10^6$ cells/ml in tissue culture media. n-butyric acid (sodium salt, Sigma Chemical Corp., Cat. No. B5887) was added to a final concentration of 5 mM (diluted from a 1M stock solution made in tissue culture media). Cells were grown overnight (18–24 hours) at 37° C., 5% $CO_2$ prior to use. Lower concentrations have been used successfully (e.g., 2.5 mM and 1 mM n-butyric acid). n-butyrate treatment has been reported to induce protein levels up to about 10-fold relative to uninduced controls (see, e.g., Palermo, D. P., et al., *J. Biotech.*, 19: 35–48 (1991) and references cited therein). CKR-3 mRNA levels driven by the human CMV immediate early gene promoter were elevated dramatically by n-butyrate treatment.

Monoclonal Antibody Production and Flow Cytometry

MAbs reactive with synthetic peptide were produced as described above in Example 5. MAbs were screened by ELISA as follows. 50 μl of peptide, at a concentration of 2 μg/ml in carbonate buffer, was used to coat NUNC 96-well Maxisorp plates for at least 4 hours at 4° C. 300 μl/well of blocking buffer (PBS+1% BSA) was added for at least 2 hours. Plates were washed four times with PBS/Tween 20, and 50 μl of MAb supernatant was added to each well and incubated at 37° C. for one hour. Plates were washed four times with PBS/Tween 20 and alkaline phospatase-conjugated second antibody (Jackson ImmunoResearch Laboratories, West Grove Pa.) diluted 1:500 in PBS was added to each well. After an incubation at 37° C. for 30 minutes, plates were washed four times with PBS/Tween 20. The substrate used for the color reaction was p-nitrophenylphosphate dissolved in diethanolamine buffer (Bio-Rad). Plates were read at 410 nm on an ELISA reader.

To determine which anti-peptide MAbs could recognize native, surface expressed CKR-3, the anti-peptide MAbs were screened against transiently transfected cells and eosinophils. For MAb staining, cells were washed once with PBS, and resuspended in 100 μl PBS containing 2% FCS, 0.1% sodium azide (FACS buffer), 5 μg/ml purified antibody, 5 μg/ml MOPC-21 $IgG_1$ isotype matched control MAb (Sigma) or 100 l hybridoma culture supernatant. After 30 min at 4° C., cells were washed twice in FACS buffer, and resuspended in 100 μl of FITC-conjugated affinity purified $F(ab')_2$ goat anti-mouse IgG (Jackson). After incubating for 30 minutes at 4° C., cells were washed twice in FACS buffer and analyzed by FACSCAN flow cytometer analysis to determine the level of surface expression. Propidium iodide was used to exclude dead cells.

Figure 10A:
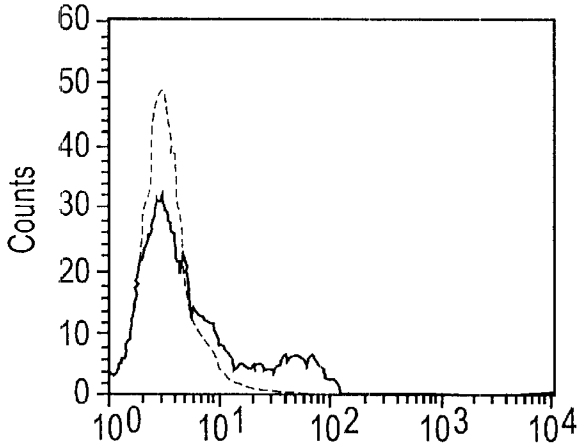
FIGS. 10A–10C are graphs illustrating cell surface staining of L1.2 cells transiently transfected with a CKR-3 receptor (FIG. 10A), mock-transfected L1.2 control cells (FIG. 10B), or cell line E5 (a stable L1.2 CKR-3 transfectant) (FIG. 10C) with an anti-CKR-3 monoclonal antibody (LS26-5H12, solid line). Background staining with control monoclonal antibody MOPC-21 is also shown (dotted lines).
Figure 10B:
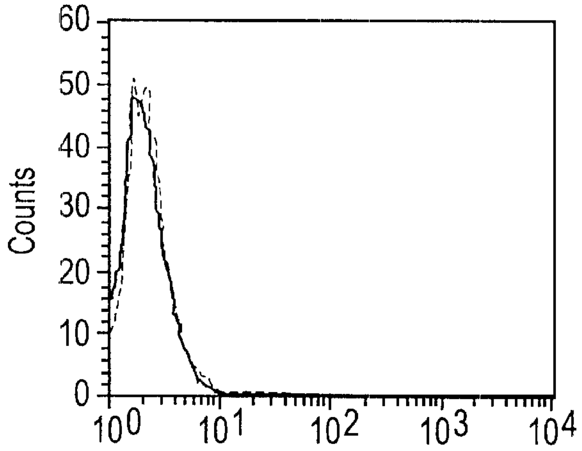
Figure 10C:
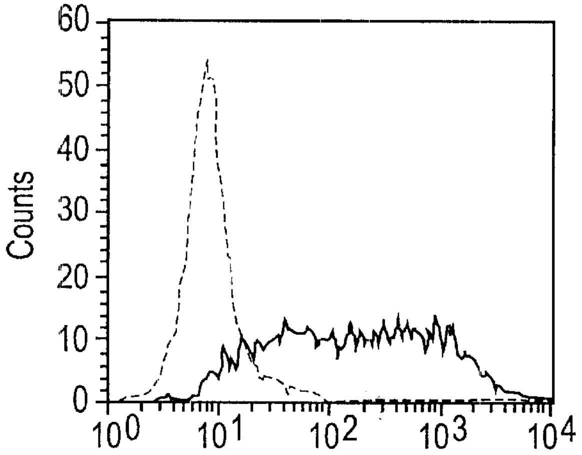

Surface Expression of Receptor on Stable Transfectants of the L1.2 Cell Line FIG. 10A shows detectable surface staining of the transiently transfected receptor on a subpopulation of L1.2 cells, using an anti-receptor MAb, LS26-5H12. Untransfected L1.2 cells were negative (FIG. 10B). A stable cell line was constructed by limiting dilution cloning of the transfectants and selection for higher surface staining as described above. This process yielded lines that had much higher levels of receptor expression (FIG. 10C). Northern blot analysis confirmed the presence of transfected CKR-3 mRNA in one of the subclones, designated E5, and its absence in untransfected L1.2 cells (not shown).

EXAMPLE 7

Ligand Binding Specificity of Stable L1.2 Transfectants

Chemokines

Recombinant human chemokines were obtained from Peprotech, Inc. (Rocky Hill, N.J.), except for human eotaxin which was synthesized using solid-phase methods that were optimized and adapted to a fully automated peptide synthesizer (model 430A; Applied Biosystems, Inc., Foster City, Calif.) as described (Clark-Lewis, I., et al., *Biochemistry*, 30: 3128–3135 (1991)). Human eotaxin is also commercially available from Peprotech.

$^{125}$I-Labeling $^{125}$I-labeled eotaxin was produced using the Bolton Hunter reagent (NEN), as described (Coligan, J. E., et al., Eds., 1992, *Current Protocols in Immunology* (New York: John Wiley and Sons)). The specific activity of radiolabeled eotaxin was calculated to be 180 Ci/mM.

Ligand Binding

Chemokine binding to target cells was carried out using a modification of a previously reported method (Van Riper, G., et al., *J. Exp. Med.* 177: 851–856 (1993)). Cells were washed once in PBS and resuspended in binding buffer (50 mM HEPES, pH 7.5, 1 mM $CaCl_2$, 5 mM $MgCl_2$, 0.5% BSA and 0.05% azide) at a concentration of $1\times10^7$/ml. Aliquots of 50 μl ($5\times10^5$ cells) were dispensed into microfuge tubes, followed by the addition of cold competitor and radiolabeled chemokines. The final reaction volume was 200 μl. Non-specific binding was determined by incubating cells with radiolabeled chemokines in the presence of 250–500 nM of unlabeled chemokines. After 60 minutes incubation at room temperature, the cells were washed 3 times with 1 ml of binding buffer containing 0.5 M NaCl. Cell pellets were then counted.

Competition is presented as the percentage of specific binding as calculated by 100(S-B)/(T-B), where S is the radioactivity of the sample, B as background binding and T as total binding without competitors. Background binding was obtained by incubating cells with radiolabeled chemokine and at least 400-fold excess of unlabeled chemokines. The total binding of eotaxin to E5 cells was 11611±119 cpm and background binding 2248±745 cpm. The total binding of eotaxin to eosinophils was 7866±353 cpm and background binding 1148±518 cpm. Duplicates were used throughout the experiments and the standard deviations were always less than 10% of the mean. All experiments were repeated at least three times. Curve fit was calculated by KALEIDAGRAPH software.

Figure 11A:
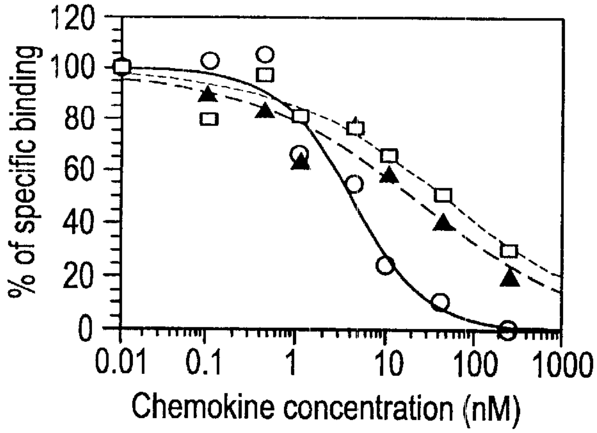
FIGS. 11A–11D are graphs illustrating the results of competitive ligand binding of radiolabeled human eotaxin to the E5 cell line (a stable L1–2 cell line transfected with a CKR-3 receptor.
Figure 11B:
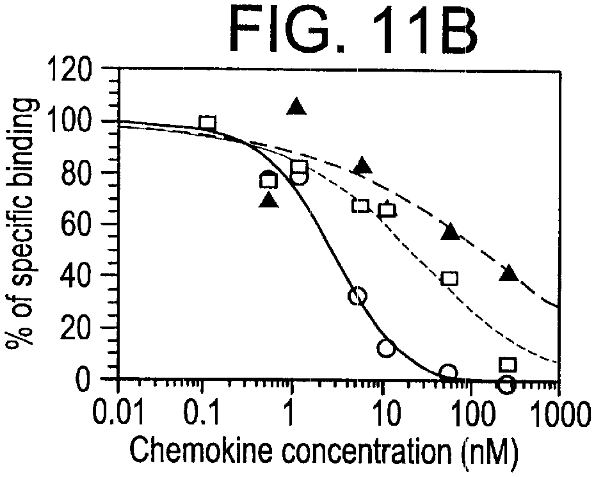
Figure 11C:
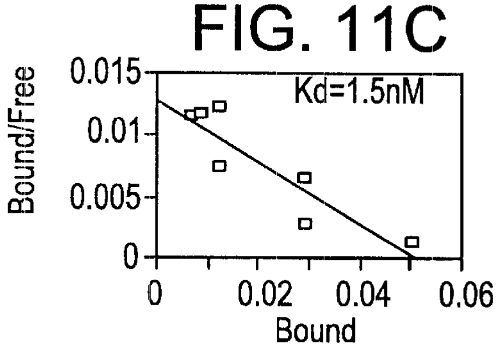
Figure 11D:
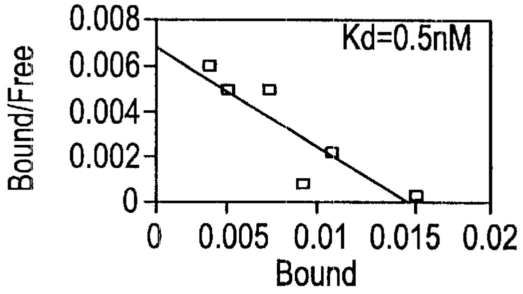
Figure 12:
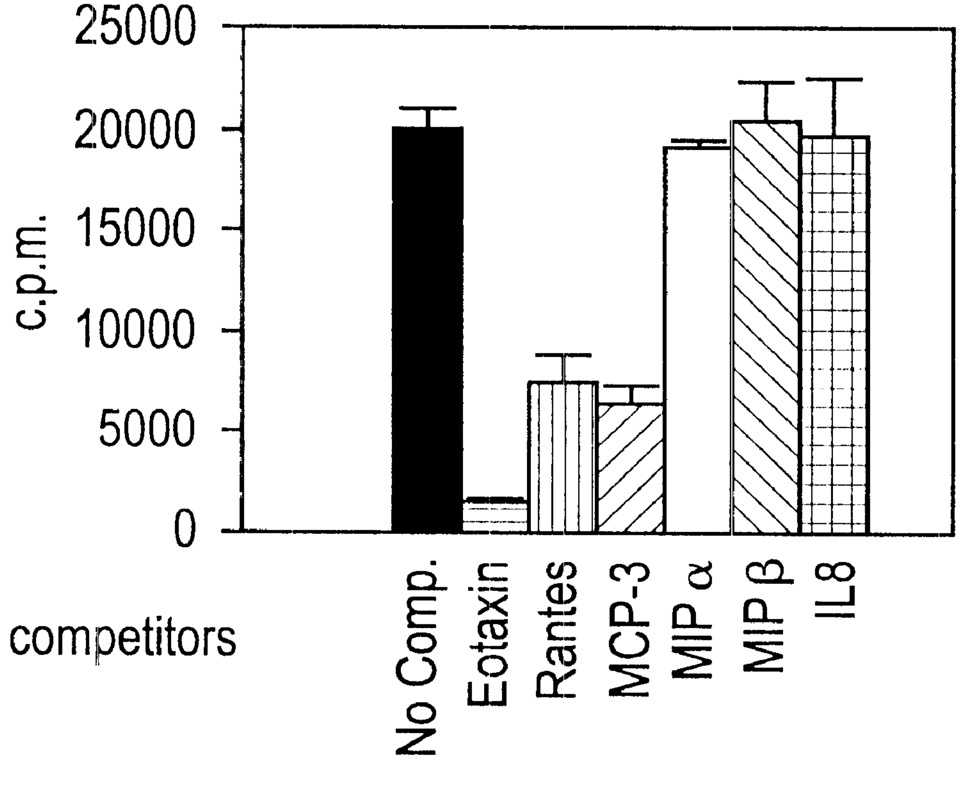
FIG. 12 is a histogram illustrating the inhibition by various chemokines of human eotaxin binding to the E5 cell line. E5 cells (stable L1–2/CKR-3 transfectants) were incubated with 0.6 nM radiolabeled eotaxin and 250 nM unlabeled chemokines or no competitor as indicated.

The E5 cell line described in Example 6 was tested for its ability to bind radiolabeled eotaxin. Cells were incubated with 0.6 nM $^{125}$I-labeled eotaxin and various concentrations of cold competitor. FIG. 11A shows that the transfected cells bound $^{125}$I-labeled eotaxin specifically and with high affinity. Scatchard analysis of the binding data indicated a dissociation constant (Kd) of 1.5 nM (FIG. 11C), similar to the value of 0.5 nM obtained using purified human eosinophils (FIG. 11D). In addition, both RANTES and MCP-3 were able to specifically compete for binding. None of the other chemokines tested, including MIP-1α, MIP-1β, or IL-8 were able to specifically compete for radiolabeled ligand (FIG. 12).

Chemotaxis Assays

Chemotaxis with human eosinophils was assessed using a modification of a transendothelial assay (Carr, M. W. et al., *Proc. Natl. Acad. Sci. USA*, 91: 3652–3656 (1994)). The endothelial cells used for this assay were the endothelial cell line ECV 304, obtained from the European Collection of Animal Cell Cultures (Porton Down, U.K.). Endothelial cells were cultured on 6.5-mm diameter BIOCOAT TRANSWELL tissue culture inserts (Costar Corp., Cambridge Mass.) with a 3.0 μM pore size. Culture media for ECV 304 cells consisted of M199+10% Fetal Calf Serum, L-glutamine, and antibiotics.

Assay media consisted of equal parts RPMI 1640 and M199, with 0.5% BSA. 24 hours before the assay, $2\times10^5$ ECV 304 cells were plated onto each insert of the 24-well chemotaxis plate, and incubated at 37° C. Chemotactic factors (diluted in assay medium) were added to the 24-well tissue culture plates in a final volume of 600 μl. Endothelial-coated tissue culture inserts were inserted into each well and $10^6$ cells were added to the top chamber in a final volume of 100 μl. The plate was incubated at 37° C. in 5% $CO_2$/95% air for 4 hours.

The cells that had migrated to the bottom chamber were counted using flow cytometry. 500 μl of the cell suspension from the lower chamber was placed in a tube, and relative cell counts were obtained by acquiring events for a set time period of 30 seconds. This counting method was found to be reproducible, and enables gating on the leukocytes and the exclusion of debris or other cells. Counts obtained in this way match closely those obtained by counting with a microsope.

The same assay was used to assess chemotaxis of L1.2 cells or L1.2 receptor transfectant cell lines, except that endothelial cells were not used to coat the BIOCOAT TRANSWELL tissue culture inserts.

CKR-3 Expression in L1.2 Cells Confers Chemotactic Responsiveness for Eotaxin, RANTES and MCP-3

Figure 13A:
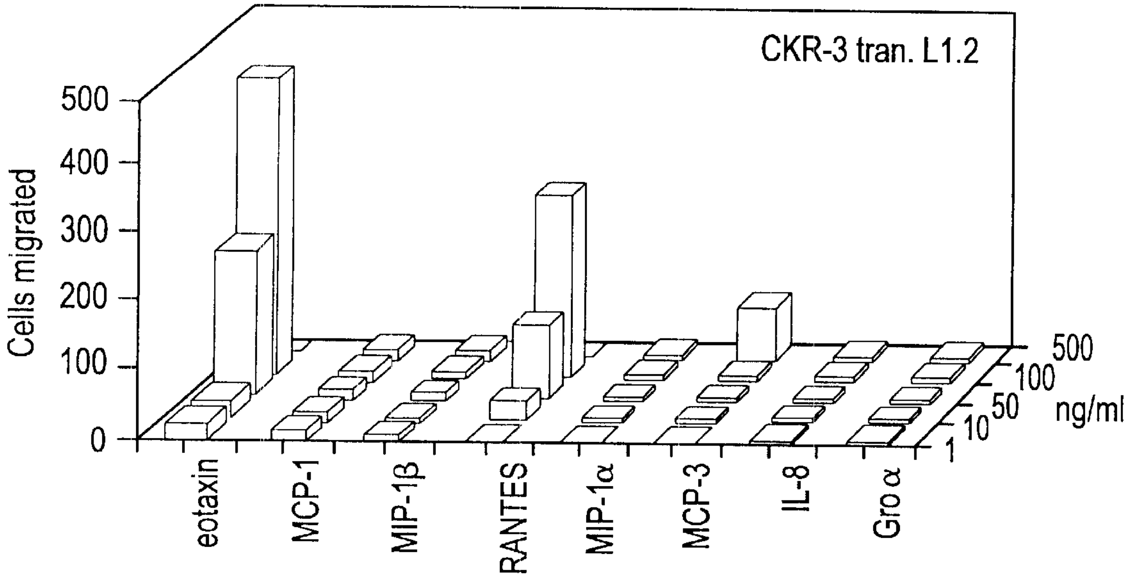
FIGS. 13A–13C are histograms illustrating chemotaxis of L1.2 cells and L1.2 receptor transfectants. $1\times10^6$ cells of the E5 cell line (stable L1–2/CKR-3 transfectants) (FIG. 13A), the parental L1.2 cell line (FIG. 13B), or an IL-8 RB L1.2 receptor transfectant line LSLW-2 (FIG. 13C) were placed in the top chamber and chemokines placed in the bottom chamber at the concentrations specified. Migration was allowed for 4 hours and cells migrating to the bottom chamber were counted. All assays were performed in duplicate and the results representative of at least three separate experiments. Chemokines are listed along the x-axis, number of cells migrated along the y-axis, and concentration of chemokine along the z-axis.

L1.2 receptor transfectants were tested for their ability to migrate in response to a panel of chemokines over a range of concentrations. The CKR-3 expressing cell line E5 showed a chemotactic response to eotaxin, RANTES, and MCP-3 with a peak response to eotaxin at 100 ng/ml, although specific migration could be detected as low as 10 ng/ml (FIG. 13A). While a response to RANTES was evident at both 10 ng/ml and 100 ng/ml, the magnitude of the response was not as great as with eotaxin. MCP-3 appeared to be a less potent chemoattractant on the E5 cell line than on eosinophils, with no detectable migration below 100 ng/ml. No significant response to other chemokines tested was seen with this cell line. In other control experiments, cells did not migrate to the bottom chamber when chemokine was added to the top well alone, confirming that cell migration was chemotactic rather than chemokinetic (not shown).

Figure 13B:
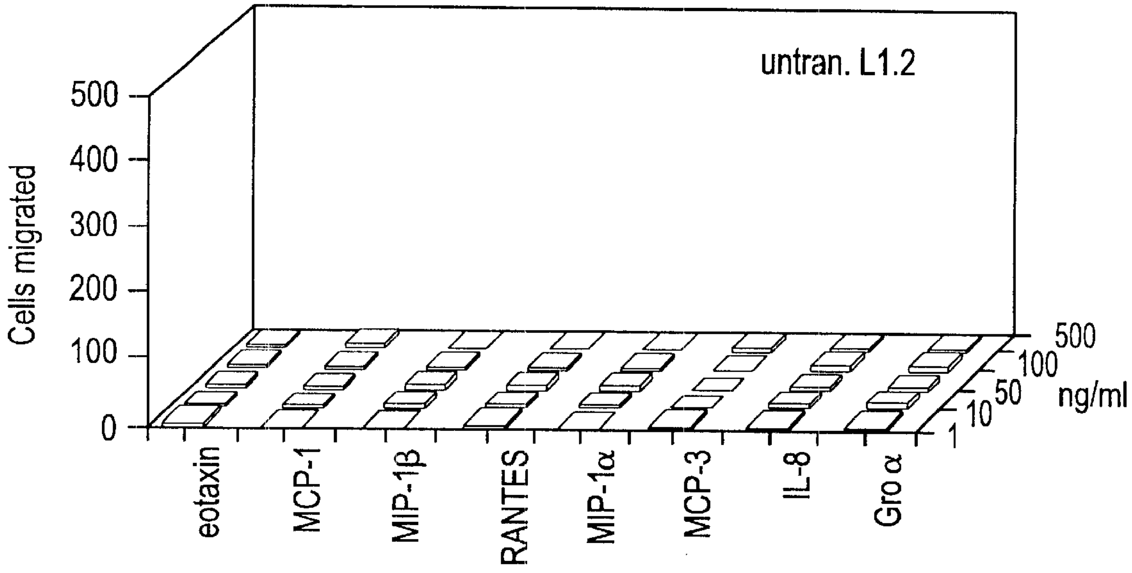
Figure 13C:
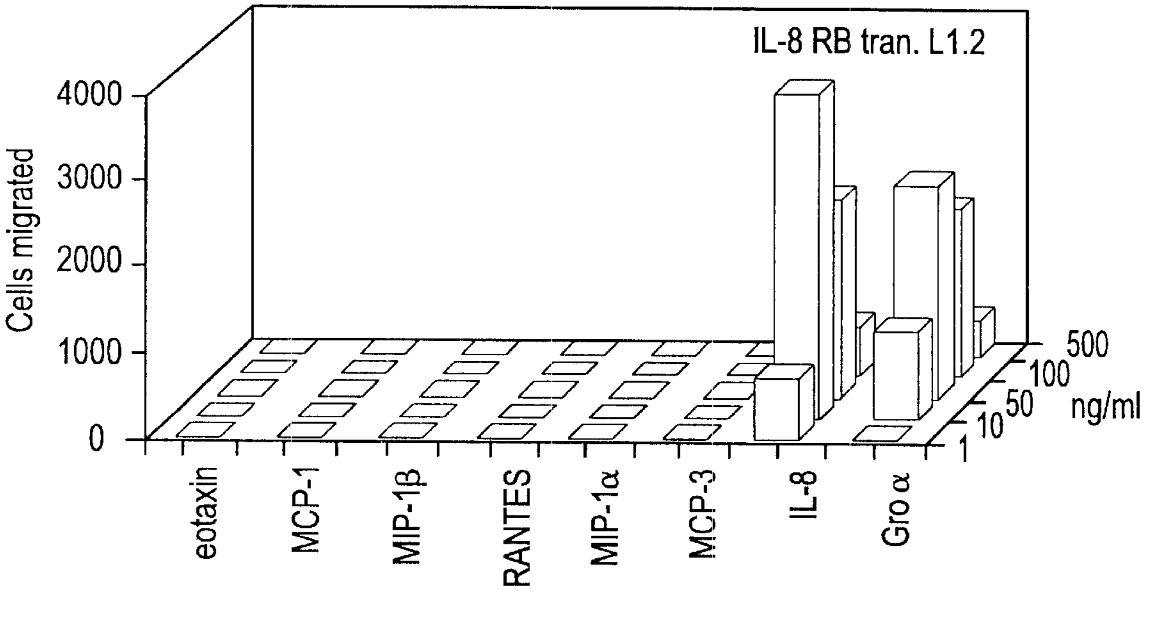

The untransfected L1.2 cell line did not migrate in response to any chemokines tested (FIG. 13B). Indeed, a striking feature of the L1.2 cell line was the very low background chemotaxis to non-specific ligands. As a specificity control, L1.2 cells transfected with IL-8 RB migrated specifically in response to IL-8 and GROα (FIG. 17C), as well as NAP-2 and ENA-78 (not shown), but not to other CXC or CC chemokines. Other chemokine receptors which were introduced into L1.2 cells by transfection also confer chemotactic ability to their specific ligands, including CKR-2 transfectants (which respond to MCP-1 and MCP-3), CKR-1 transfectants (which respond to MIP-1α), and IL-8 RA transfectants (which respond to IL-8) (not shown). Pertussis toxin completely abrogated the chemotactic response of both eosinophils and the CKR-3 transfectants to eotaxin indicated that the receptor was signaling through the Gα subclass (Simon, M. I., et al., *Science*, 252: 802–808 (1991)) in both normal and transfected cells (not shown).

The Chemotactic Profile of Eosinophils Resembles that of CKR-3 Transfectants

Figure 14A:
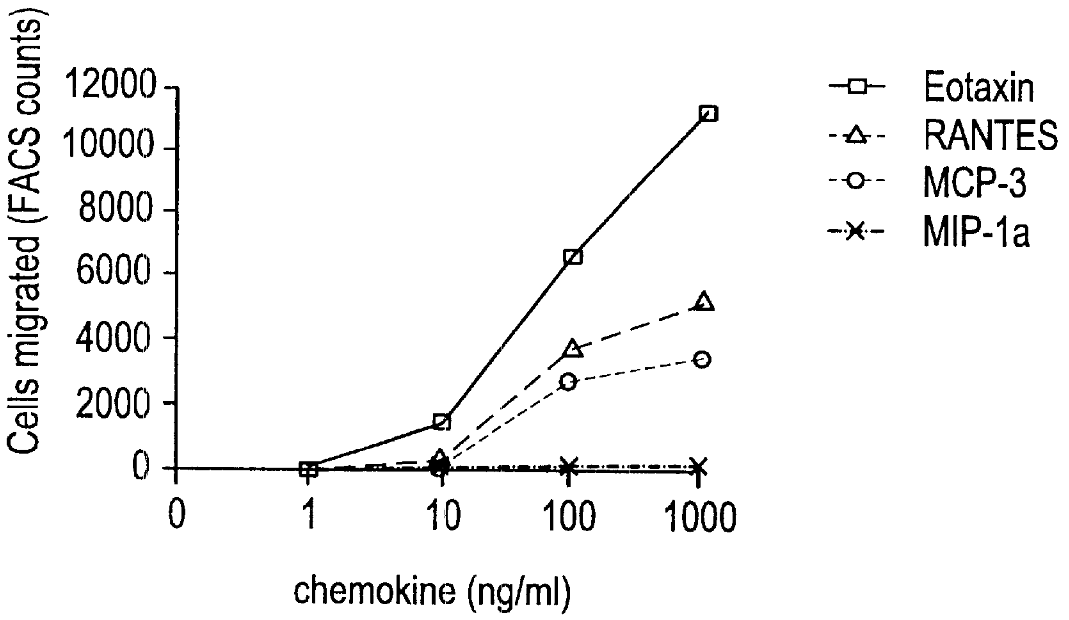
FIGS. 14A–14B are graphs illustrating the chemotactic response of eosinophils from two different individuals. The response resembles that of CKR-3 L1.2 transfectants. Donor to donor variation of chemotactic responses of eosinophils to eodaxin, RANTES, MCP-3, and MIP-1α was observed. Eosinophils were purified from blood, and assessed for their chemotactic response to various concentrations of chemokines. Values are from a representative experiment of at least 4 performed, using the same two blood donors.
Figure 14B:
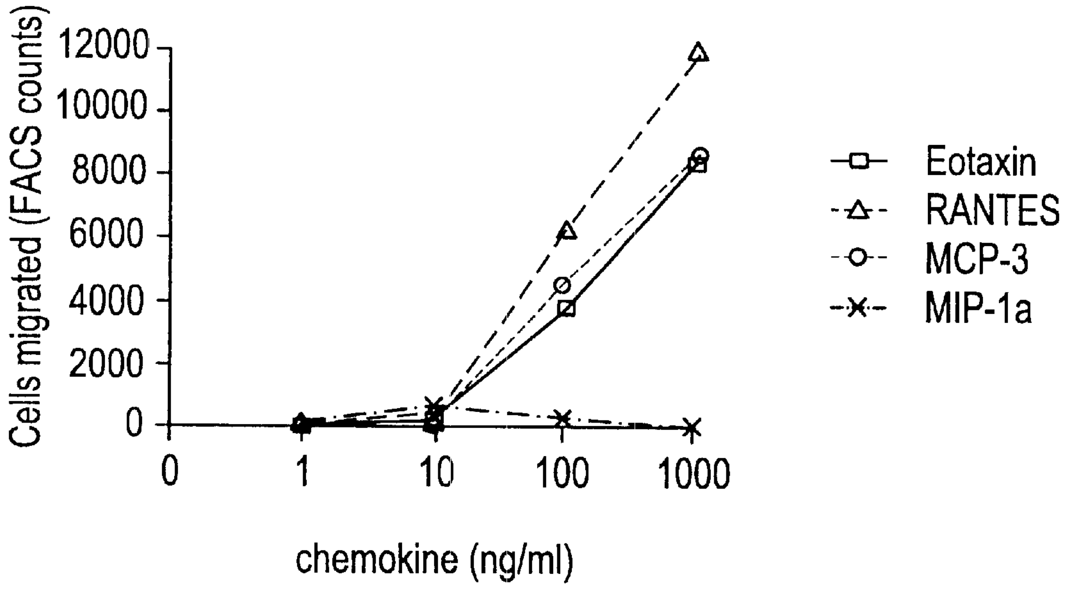

In order to assess whether the function of normal eosinophils resembled that of CKR-3 L1.2 transfectants, chemotaxis experiments were performed using eosinophils from a number of normal individuals (humans), having high levels of eosinophils (~6 to 8% of WBC) (purified as described in Example 5). FIGS. 14A–14B show two characteristic patterns of eosinophil chemotaxis observed in two different individuals. One pattern was characterized by a robust migration to eotaxin, and a lesser response to RANTES and MCP-3 (FIG. 14A). The other pattern showed essentially equivalent chemotaxis in response to eotaxin, RANTES and MCP-3 (FIG. 14B). These patterns were not due to variations in the assay, since within each individual, they were highly reproducible over a long period of time. MIP-1α showed only weak chemotactic activity for eosinophils in the second class of individuals.

EXAMPLE 8

Cloning of a CDNA Encoding Eos L2

Construction of an Eosinophil cDNA Library

Eosinophils were obtained from a patient (M.V.) diagnosed with idiopathic hyper-eosinophilic syndrome (Costa, J. J. et al., *J. Clin. Invest.*, 91: 2673 (1993). RNA was isolated using a standard guanidinium isothiocyanate/cesium chloride method (In: *Current Protocols In Molecular Biology*, Vol. 1, Ausubel, F. M. et al., Eds., (John Wiley & Sons: New York, N.Y.) page 4.2.2–4.2.3 (1991)). mRNA was obtained using DYNABEADS paramagnetic beads (Dynal, Inc.), and the bacteriophage library was constructed using the SUPERSCRIPT Lambda System for cDNA Synthesis and λ cloning (Gibco BRL, Life Technologies) which comes with λgt22A, NotI-SalI arms.

Library Screening

We screened approximately 750,000 bacteriophage plaques of the resulting human eosinophil cDNA library in duplicate. The probe used was a full-length radiolabeled cDNA probe (p4 cDNA) which encodes the MIP-1α/

RANTES receptor (CKR-1)(Gao et al., *J. Exp. Med.*, 177: 1421 (1993)). The p4 cDNA was cloned into the BamHI (5') and XhoI (3') sites of pcDNAI (Invitrogen). A BamHI-XhoI fragment of this clone (i.e., p4 cDNA in pcDNAI) was obtained by restriction digestion, and isolated using GENECLEAN DNA purification system (Bio101). The fragment was labeled with $^{32}$p using a random primer labeling kit (Boehringer Mannheim Biochemicals).

Filters were prehybridized by incubation for two hours at 42° C., in a solution of 50% formamide, 5×SSC, 1×Denhardt's, 10% Dextran Sulfate, 20 mM TRIS, pH 7.5, 0.1% SDS (sodium dodecyl sulfate). Hybridization was performed overnight at 42° C. in the same solution. Eosinophil CDNA library filters were then washed two times with 2×SSC/0.1% SDS at room temperature, and two times with 2×SSC/0.1% SDS at 42° C. Each wash was for 30 minutes. Filters were exposed overnight and positive plaques were picked in duplicate. Clones were further evaluated when positive in duplicate after the low stringency washes.

Characterization of cDNA Clones

Plaques were plaque purified, and DNA was isolated by a small scale phage lysis protocol (In: *Current Protocols In Molecular Biology*, Vol. 1, Suppl. 10, Ausubel, F. M. et al., Eds., (John Wiley & Sons: New York, N.Y.), page 1.13.7 (1991). The bacteriophage DNA was digested with EcoRI (site in arm of vector) and NotI. The inserts released by digestion were visualized on a gel, and were found to be approximately 1.6 kb in length. The ~1.6 kb insert present in a plaque designated Mip-16 or M-16, was isolated using GENECLEAN DNA purification system (Bio101), and was cloned into the EcoRI and NotI sites of PBLUESCRIPT vector KS (Stratagene), which had been digested with both EcoRI and NotI to produce asymmetric ends. The ligated plasmid was introducted into XL1-Blue *E. coli* cells (Stratagene) made competent as described by Hanahan (Hanahan, D., (1985), In: DNA cloning, Volume 1, D. M. Glover, Ed. (IRL Press: Washington, D.C.), pp. 109–135).

Dideoxy sequencing of the M-16/Bluescript construct was performed using a dideoxynucleotide sequencing kit obtained from USB (United States Biochemical, Cleveland, Ohio). The nucleotide sequence of this clone was determined to encode a novel protein with a high degree of homology to the MIP-1α/RANTES receptor; however, from the sequence data, the clone did not appear to be full-length.

In order to identify a full-length clone, 15–20 additional plaques were isolated and purified, and the inserts present in the phage were characterized by restrict ion enzyme analysis and/or sequencing. Another λ clone, designated M31, which was isolated was found to contain a ~1.8 kb insert. The insert was cloned into the EcoRI and NotI sites of PBLUESCRIPT vector KS (Stratagene), and introduced into XL1-Blue *E. coli* cells (Stratagene) as described above. DNA sequencing of this clone (M31 insert in PBLUESCRIPT vector, referred to as M31/Bluescript construct) was performed as described above, and revealed that it encoded a full-length receptor.

The M31 insert was released from the M31 /Bluescript construct by digestion with EcoRI and NotI. The resulting fragment was isolated using GENECLEAN DNA purification system (Bio101), and was inserted into the EcoRi and NotI sites of vector Ap$^r$, which had been digested with both EcoRI and NotI to produce asymmetric ends. Vector Ap$^r$M9 (de Fougerolles, A. R. et al., *J. Exp. Med.*, 177: 1187–1192 (1993)) is a derivative of CDM8 (Invitrogen) containing the β-lactamase from PBLUESCRIPT vector and a polylinker from pSP64. The resulting construct, designated A31, was introduced into competent XL1-Blue cells.

The nucleotide sequence of the full-length cDNA and the predicted amino acid sequence of the encoded protein are shown in FIGS. 2A–2C (see also SEQ ID NO:3 and SEQ ID NO:4). The cDNA sequence shown in FIGS. 2A–2C was determined from clones A31 (bases 15–365 (numbering as in FIGS. 2A–2C)), and the M-16/Bluescript construct (bases 366 to 1152 (numbering as in FIGS. 2A–2C)). A comparison of the amino acid sequence of the novel receptor with other proteins revealed that the novel receptor and the MIP-1α/RANTES receptor share 62% sequence identity, and the novel receptor and the MCP-1 receptor share 50.57% sequence identity. Sequence identity was determined using the Wisconsin UW GCG package (program gap), with the Needleman and Wunsch algorithm (Needleman and Wunsch, *J. MOl. Biol.* 48:443–453 (1970)).

Northern Analysis

RNA for Northern analysis was obtained from a patient having hyper-eosinophilia. The eosinophils were isolated as described (Costa, J. J., et al., *J. clin. Invest.*, 91: 2673 (1993)). Total eosinophil RNA was isolated using standard procedures (In: *Current Protocols In Molecular Biology*, Vol. 1, Ausubel, F. M. et al., Eds., (John Wiley & Sons: New York, N.Y.) page 4.2.2–4.2.3 (1991)). The total RNA was fractionated on a 1% agarose gel, and then blotted onto GENESCREEN filters (New England Nuclear). Filters were probed at high stringency according to the manufacturer's protocol for high stringency washing of GENESCREEN blots (New England Nuclear).

Several Northerns were prepared. One involved probing with the EcoRI-NotI fragment of the M16/Bluescript construct, and others were probed with the EcoRI-NotI fragment from clone A31. Both EcoRI-NotI fragments include the 3' untranslated regions. Probes were labeled with $^{32}$p using a random primer labeling kit (Boehringer Mannheim Biochemicals).

The Northern blots each revealed a very strong signal of approximately 1.8 kb in total human eosinophil RNA. This result indicates that the A31 RNA is expressed at very high levels in eosinophils from this patient.

EXAMPLE 9

Expression of CDNA Encoding Eos L2 Receptor and Ligand Binding Studies

Constructs

Vectors A31 (described above) and A31-pcDNA3 were used for expression and binding analyses. To construct A31-pcDNA3, vector A31 was digested with EcoRI and NotI, the ~1.8 kb insert was isolated using GENECLEAN DNA purification system (Bio101), and was inserted into the EcoRI and NotI sites of vector pcDNA-3 (Invitrogen), which had been digested with both EcoRI and NotI. The ligated construct, designated A31-pcDNA3, was introduced into competent XL1-Blue cells.

Transient Transfections

Transient transfections using A31 in the kidney cell line 293 initially suggested high affinity binding of A31 with radioactive RANTES. These initial binding studies have been difficult to reproduce. Accordingly, stable cell lines have subsequently been produced with A31/pcDNA3 stably integrated into both RBL (rat basophilic leukemia) and 293 cells. RBL cells (Accession No. ATCC CRL 1378) were obtained from the American Type Culture Collection (ATCC), 12301 Parklawn Drive, Rockville, Md. 20852, and 293 cells (Accession No. ATCC CRL 1573) were a gift from I. Charo, Gladstone Cardiovascular Institute.

Stable Cell Lines

Stable cell lines were constructed as follows. A31-pcDNA3 was linearized by digestion with NotI. The linearized plasmid was introduced into RBL and 293 cells by electroporation. Confluent 293 and RBL cells growing in 100×20 mm plates were trypsinized, resuspended in 1 cc of phosphate buffered saline (PBS) and electroporated in a 0.4 cm cuvette (BioRad) with settings of 960 microfarads and 250 volts. Stable transfectants were isolated by positive selection in medium containing geneticin. Specifically, the cells were first cultured in DMEM (BRL), 10% fetal calf serum for several days, and then were switched to DMEM, 10% fetal calf serum with 0.9 mg/cc of Geneticin (BRL). (DMEM, Dulbecco's Modified Eagle's Medium). After 3 weeks, surviving colonies were isolated sterilely with cloning cylinders, and individual clones were grown in individual wells in DMEM, 10% fetal calf serum with 0.9 mg/cc of Geneticin (BRL).

Surviving clones which expressed A31 RNA at high levels were detected by Northern analysis. 120 stable transfectants of the RBL line, and 38 stable transfectants of the 293 cell line, were screened. Specifically, RNA from individual clones was isolated using the acid phenol method (Chomczynski, P. and N. Sacchi, *Anal. Biochem*., 162: 156–159 (1987)). RNA was fractionated by electrophoresis, blotted onto GENESCREEN filters (New England Nuclear), and Northern blots were probed according to the manufacturer's suggestion for high stringency wash. The EcoRI-NotI insert from plasmid A31 was isolated, radiolabeled with $^{32}$p using the random primer labeling kit (Boehringer Mannheim Biochemicals), and used as a probe. RNA was quantified by ethidium bromide staining on gels. Untransfected 293 or RBL cells were used as negative controls for the corresponding transfectants.

Stable cell lines designated A31-293-#8, A31-293-#9, A31-293-#17, and A31-293-#20 were subsequently found to express A31 RNA at very high levels relative to other lines. Clone A31-293-#20 which highly expresses the A31 message by Northern analysis, was selected for further study.

One RBL line was found to express low-medium amounts of RNA, but did not appear to bind RANTES under the conditions used (not shown).

Ligand Binding

Stable clone A31-293-#20 was grown in quantities sufficient for binding assays. In particular, cells were grown in 100 mm plates in DMEM, 10% fetal calf serum, 0.9 mg/cc geneticin. Plates were grown to confluence, and membranes were prepared as follows. Culture medium was removed, and the cells were washed with phosphate buffered saline. Cells were harvested by washing with TEN (40 mM TRIS, pH 7.5, 1 mM EDTA, and 150 mM NaCl). The cells were frozen in liquid nitrogen, thawed at room temperature, and the membrane fraction was collected by centrifugation in a conical tube for 10 minutes at 18,000 rpm. Each binding point was determined using one-half of the membranes harvested from a single 100 mm plate grown to confluence.

$^{125}$I-labeled RANTES was purchased from New England Nuclear, and cold RANTES was purchased from Peprotech (Princeton, N.J.). $^{125}$I-labeled MCP-3 was a gift from New England Nuclear, and cold MCP-3 was a gift from J. Van Damme, Rega Institute for Medical Research, University of Leuven, B-3000 Leuven, Belgium (see also, Opdenakker, G. et al., Biochem. Biophys. Res. Commun., 191(2): 535–542 (1993)). Binding assays were performed as described by Van Riper, G. et al., *J. Exp. Med*., 177: 851 (1993), with the following modifications. In particular, the binding to membranes of 0.125 nanomolar of $^{125}$I-RANTES was performed in the presence of varying concentrations of unlabeled ligand. Binding buffer was 50 mM Hepes, 1 mM $CaCl_2$, 5 MM $MgCl_2$, 0.5% BSA, pH 7.2. Radiolabeled and cold ligand were added simultaneously to the membranes (see above), and incubated for 1.5 hours at room temperature. The binding reaction was added to 2 cc of wash buffer (0.5 M NaCl, 50 mM Hepes, 1 mM $CaCl_2$, 5 mM $MgCl_2$, 0.5% BSA, pH 7.2), mixed by vortexing, and then placed on polyethyleneimine-treated Whatman GFC filters. Filters were washed with an additional two ccs of wash buffer. Activity retained on filters after washing was determined by scintillation counting. Filters were placed in 5 cc of scintillation fluid and were then counted in a miniaxi-beta liquid scintillation counter (United Technologies, Packard, Downers Grove, Ill.). All points were determined in triplicate, except for the point at 2 nM, which was determined in duplicate.

Figure 15:
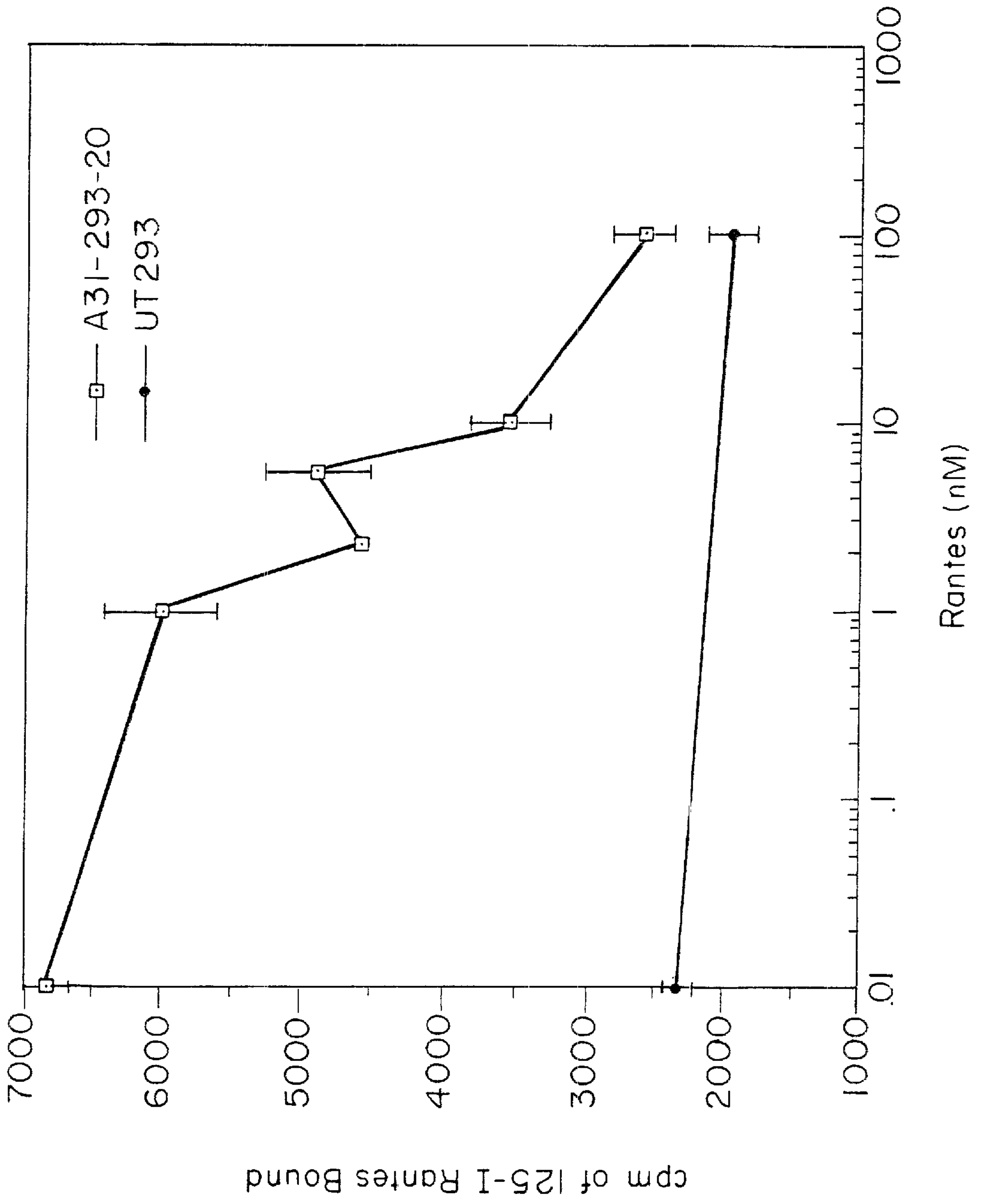
FIG. 15 is a graph illustrating the binding of $^{125}$I-labeled RANTES to membranes from a stable cell line (A31-293-20) obtained by transfecting 293 cells with the A31 cDNA clone (square with central dot) as compared with binding to membranes from untransfected 293 cells (filled circles).

The results of the assay indicated high affinity binding of RANTES to the receptor encoded by the A31 clone (FIG. 15). Scatchard analysis of the data indicated a $Kd_4$ of ~2.5 nM for RANTES, which is what is expected in normal cells.

Figure 16:
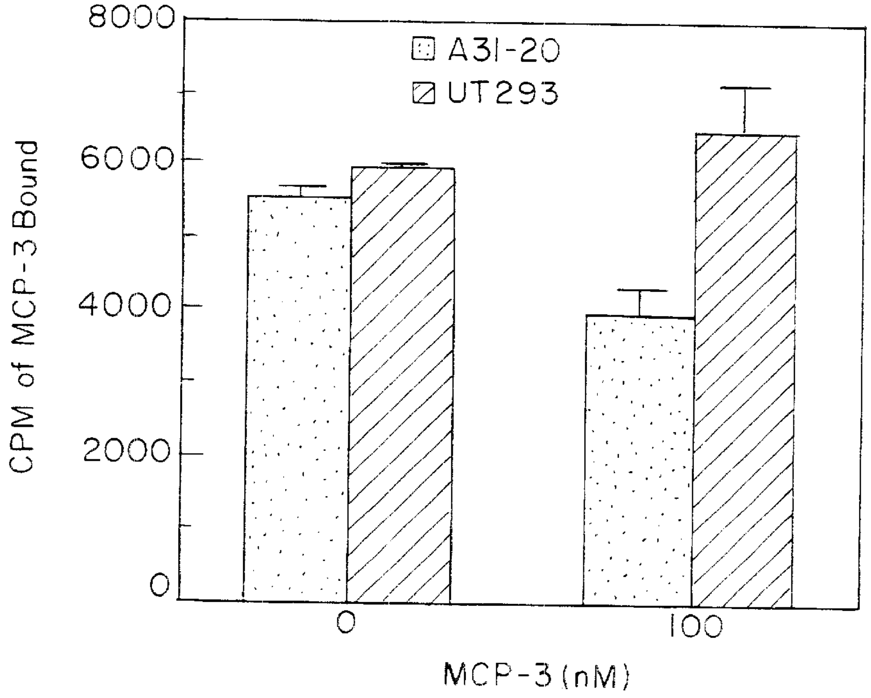
FIG. 16 is a histogram illustrating the binding of $^{125}$I-labeled MCP-3 to a membranes from a stable cell line (A31-293-20) obtained by transfecting 293 cells with the A31 cDNA clone as compared with binding to membranes from untransfected 293 cells. Binding of labeled MCP-3 to membranes from transfected (A31-20) or untransfected (UT293) cells was determined in the absence of cold MCP-3 (0 nM) or in the presence of cold MCP-3 (100 nM).

Binding of MCP-3 to membranes from clone A31-293-#20 was also assessed using the ligand binding assay described above for RANTES binding to A31-293-#20 membranes (FIG. 16). Binding reactions contained 0.125 nanomolab 125I-labeled MCP-3.

Figure 17:
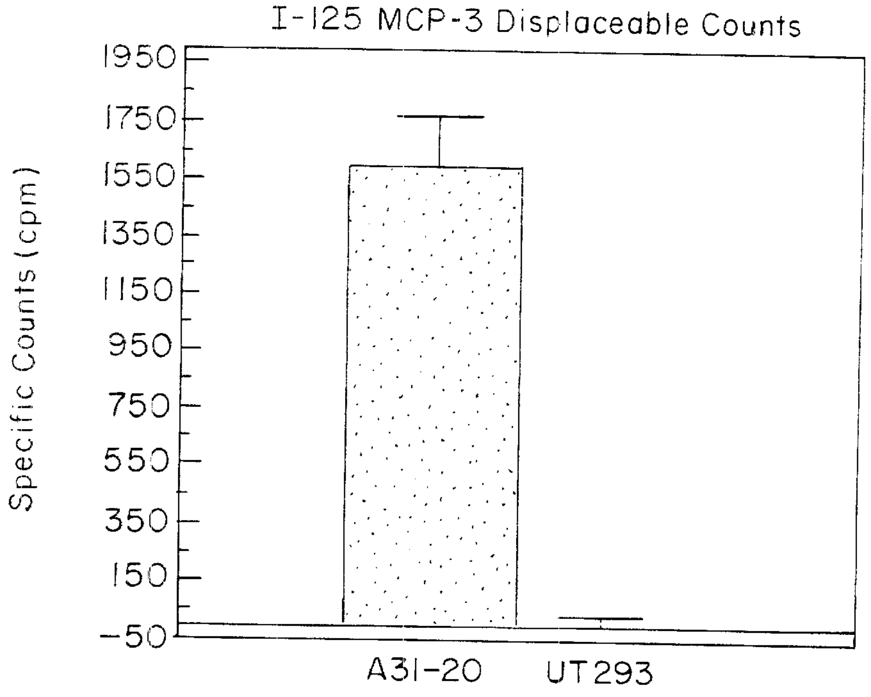
FIG. 17 is a histogram illustrating the specificity of binding, which was assessed by determining the amount of bound $^{125}$I-labeled MCP-3 which could be displaced by cold MCP-3 from membranes of transfected (A31-20) or untransfected (UT293) cells.

In addition, specificity of binding was assessed by determining the extent to which labeled MCP-3 (bound in the absence of cold MCP-3), could be displaced by cold MCP-3 (FIG. 17). All points were taken in duplicate.

The MCP-3 bound to membranes from untransfected cells could not be displaced by $^{125}$I-labeled MCP-3, indicating non-specific binding. In comparison, the MCP-3 bound to membranes from A31-293-#20 cells could be displaced by hot MCP-3, which is indicative of specific binding.

The results of these assays indicate that the receptor encoded by the A31 cDNA specifically binds human MCP-3.

EXAMPLE 10

Human Eosinophils Respond to Numerous CC Chemokines Through one Predominant Receptor Cells, Cell Lines, and Tissue Culture. Eosinophils were isolated from heparinized blood using CD 16 microbeads (Miltenyi Biotec, Auburn, Calif.), as described in Ponath, P. D., et al., *J. Clin. Invest*., 97:604–612 (1996) and were shown cytologically to be ≧99% pure. Neutrophils and PBMCs were isolated as described in Ponath, P. D., et al., *J. Clin. Invest*., 97:604–612 (1996). To generate CD3 blasts, $2\times10^6$ PBMC/ml in RPMI-1640 plus 10% FCS were added to tissue culture plates first coated with the anti-CD3 antibody TR66. After 4–6 days blasts were removed to fresh media and supplemented with IL-2 (provided by Antonio Lanzavecchia, Basel) at 50 units/ml. Other cell lines used included transfectants of the L1.2 murine pre B cell lymphoma, expressing high levels of either CCR3 (see below; Ponath, P. D., et al., *J. Exp. Med*., 183:2437–2448 (1996)), IL-8 RA (Ponath, P. D., et al., *J. Exp. Med*., 183:2437–2448 (1996)), IL-8 RB (Ponath, P. D., et al., *J. Exp. Med*., 183:2437–2448 (1996)), CCR2b, CCR4 and CCR5, and CCR1 (Campbell, J. J., et al., *J. Cell Biol*., 134:255–266 (1996)). Transfectants were maintained in RPMI-1640 supplemented with 10% bovine serum and 800 μg/ml G418. The different transfectants were monitored for expression of the relevant receptors, using mAbs specific for CCR3 (Ponath, P. D., et al., *J. Exp. Med*., 183:2437–2448 (1996)), IL-8 RA, IL-8 RB, or CCR2 (Qin, S., et al., *Eur. J. Immunol*. 26:640–647 (1996); (Ponath, P. D., et al., *J. Clin. Invest*., 97:604–612 (1996)). For CCR4 and CCR5, expression was monitored using the anti-flag mAb M2, since these receptors were constructed with this epitope at the N-terminus.

Human eosinophils were cultured in RPMI 1640 with 10% FCS and 5 ng/ml of recombinant human IL-5 (Genzyme Corp., Cambridge, MA), for 5–7 days, using tissue culture flasks containing subconfluent monolayers of ECV304 cells.

MAbs to IL-8 RA, IL-8 RB, and CCR2 (MCP-IR) have been described (Qin, S., et al., *Eur. J. Immunol.* 26:640–647 (1996)). mAb staining of cells was performed using standard procedures, as described previously (Ponath, P. D., et al., *J. Exp. Med.*, 183:2437–2448 (1996)). To enumerate antibody binding sites per cell, the F/P ratio of 7B11-FITC was determined with Simply Cellular beads (Flow Cytometry Standards Corp., San Juan, PR) and the FACSSCAN flow cytometer was calibrated with Quantum 26 beads (Flow Cytometry Standards Corp.), according to the manufacturer's instructions. 100 $\mu$l of whole blood from donors was reacted with a supersaturating amount (400 ng) of 7B11-FITC in PBS with 0.5% azide. Red cells were lysed with ammonium chloride lysing solution and the mean channel fluorescence of 7B11 stained cells was determined by flow cytometry.

Expression Vector Construction and Generation of CCR3 Stable Transfectants

The 1.8 kb CKR-3 (CCR3) genomic fragment, which was ligated into the HindIII site of the PBLUESCRIPT II KS+ vector (Stratagene) (Example 2), was modified for expression by insertion of a HindIII restriction site and optimal Kozak sequence immediately 5' to the initiation codon in a four-stage process as described in Example 3 (Construction of FLAG-tagged Eos L2 (CKR-3) Receptor Construct).

Figure 18A:
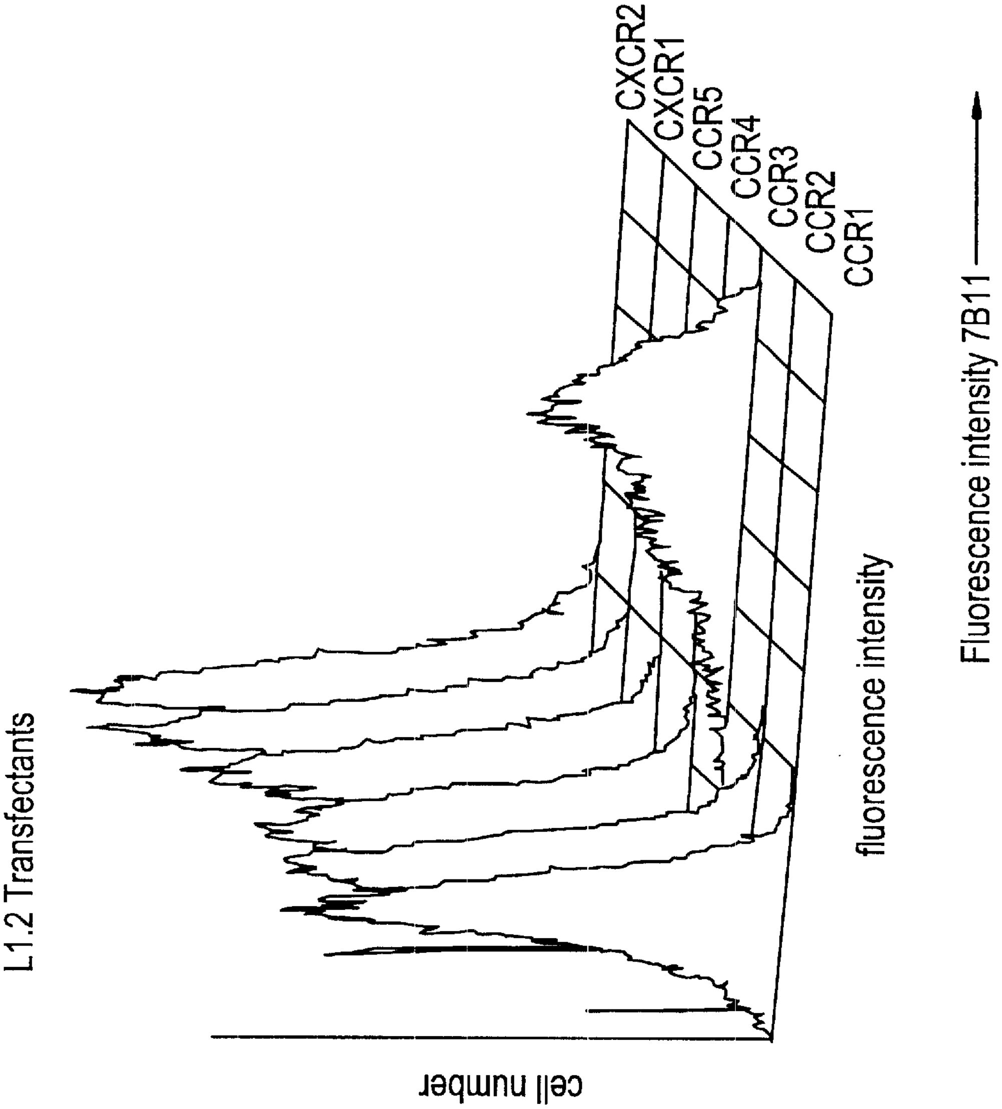
FIG. 18A is a FACs profile of the fluorescence intensity of stable L1.2 transfectants expressing either CCR1, CCR2, CCR3, CCR4, CCR5, CXCR1 (IL-8 RA), or CXCR2 (IL-8 RB) which were stained with anti-CCR3 mAb 7B11. Negative control staining for all the L1.2 transfectants (not shown) resembled the staining shown for 7B11 on CCR1 transfectants.

The murine pre-B lymphoma cell line L1.2 was maintained in RPMI-1640 supplemented with 10% bovine serum. 20 $\mu$g of the FLAG-tagged CKR-3/pcDNA3 construct (Example 3) were linearized by digestion with ScaI and used to transfect the L1.2 cell line as follows. L1.2 cells were washed twice in HBSS and resuspended in 0.8 ml of the same buffer. The plasmid DNA was mixed with the cells and incubated for 10 minutes at room temperature, transferred to a 0.4-cm electroporation cuvette, and a single pulse was applied at 250 V, 960 $\mu$F. The electroporation was followed by a 10 minute incubation at room temperature. G418 was added to a final concentration of 0.8 mg/ml 48 hours after transfection and the cells were plated in 96-well plates at 25,000 cells/well. After 2–3 weeks under drug selection, G418-resistant cells were stained with 5H12 anti-receptor monoclonal antibody, and analyzed by FACScan® (Becton Dickinson & Co., Mountain View, Calif.). For mAb staining, cells were washed once with PBS, and resuspended in 100 $\mu$l PBS containing 2% FCS, 0.1% sodium azide (FACS® buffer), 5 $\mu$g/ml affinity purified antibody or 5 $\mu$g/ml MOPC-21 $IgG_1$-isotype matched control mAb (Sigma Chemical Co., St. Louis, Mo.), or 100 $\mu$L hybridoma culture supernatant. 5H12 antibody was used as hybridoma culture supernatant. After 30 minutes at 4° C., cells were washed twice with FACS® buffer, and resuspended in 100 $\mu$l FITC-conjugated, affinity-purified $F(ab')_2$ goat anti-mouse IgG (Jackson ImmunoResearch Laboratories). After incubation for 30 minutes at 4° C., cells were washed twice in FACS® buffer and analyzed by FACScan®. Propidium iodide was used to exclude dead cells. Stable transfectants were treated with 5 nM n-butyric acid (Sigma Chemical Co., St. Louis, Mo., Catalog No. B 5887) 24 hours prior to analysis (FACS staining or binding) or immunization. All stable transfectants, including the L1.2 transfectants described in FIGS. 18A and 18C were treated with n-butyric acid. Lines with detectable surface staining were expanded and cloned several times by limiting dilution. As a negative control, CKR-3 transfected cells were stained with an irrelevant control IgG1 MAb (MOPC-21) and the same second antibody. In addition, control L1.2 cells transfected with IL-8RB, which were processed in parallel, were stained with 5H12 and second antibody. A CKR-3 transfected clone having the brightest surface staining as assessed by fluorescence intensity was used as immunogen as described below. Generally, the mean channel fluorescence intensity of the 5H12-stained cell preparation was 2–3 logs higher than staining of the controls. The transfectants used in the immunization which yielded the monoclonal antibody designated 7B11, displayed a fluorescence intensity two logs higher that the MOPC-21-stained and the IL-8RB controls.

Clones with the brightest surface staining were further analyzed by Northern hybridization to confirm the expression of transfected receptor as well as by RT-PCR using a T7 primer complementary to the pcDNA3 vector as the 5' primer and a CKR-3-specific primer as the 3' primer. No amplification was seen without addition of reverse transcriptase.

Monoclonal Antibody Production and Flow Cytometry

L1.2 CCR3 transfected cells prepared as described above were washed three times in PBS and resuspended in 200 $\mu$l PBS/$10^7$ cells. Monoclonal antibodies reactive with CCR3 were generated by immunizing C57BL6 mice with $10^7$ L1.2 CCR3 transfected cells, intraperitoneally, five to six times at 2 week intervals. The final immunization was injected intravenously. Four days later, the spleen was removed and cells were fused with the SP2/0 cell line as described (Coligan, J. E. et al., 1992, In: *Current Protocols In Immunology* (John Wiley and Sons, New York), Unit 2.5.4).

Monoclonal antibodies reactive with CCR3 were identified using untransfected and CCR3 transfected L1.2 cells, and immunofluorescent staining analysis using a FACSCAN flow cytometer (Becton Dickinison & Co., Mountain View, Calif.). Hybridoma culture supernatants were used in an indirect immunofluorescence assay in a 96-well format using anti-mouse Ig-FITC. Untransfected and CCR3 transfected L1.2 cells were washed once with PBS, and resuspended in 50 $\mu$l PBS containing 2% FCS, 0.1% sodium azide (FACS buffer). 50 $\mu$L hybridoma culture supernatant was added. After 30 minutes at 4° C., cells were washed twice with FACS buffer, and resuspended in 100 $\mu$l FITC-conjugated, affinity-purified $F(ab')_2$ goat anti-mouse IgG (Jackson immunoResearch Laboratories). After incubation for 30 minutes at 4° C., cells were washed twice in FACS buffer and analyzed by FACSCAN flow cytometer analysis. Antibodies which stained CCR-3 transfectants but not untransfected L1.2 cells were selected. Two monoclonal antibodies reactive with CCR3 were obtained from two different fusions. One of these antibodies, produced by the 7B11 hybridoma, was designated 7B11.

Chemokines, Chemotaxis Assays, and Ligand-binding Assay

Recombinant human chemokines were obtained from Peprotech (Rocky Hill, N.J.), except for eotaxin, described previously (Ponath, P. D., et al., *J. Clin. Invest.*, 97:604–612 (1996)), which was a gift of Dr. Ian Clark-Lewis. Chemotaxis of human eosinophils was assessed using a modification of a transendothelial assay (Carr, M. W., et al., *Proc. Nat'l. Acad. Sci. USA*, 91:3652–3656 (1994)), using the cell line ECV304 as described (Ponath, P. D., et al., *J. Clin. Invest.*, 97:604–612 (1996). Cells that had migrated to the bottom chamber were placed in a tube, and relative cell counts were obtained using the FACScan.

$^{125}$I-labeled eotaxin was obtained from Amersham (Arlington Heights, Ill.), and its specific activity was stated to be 2000 Ci/mM. Chemokine binding to target cells was carried out as described previously (Ponath, P. D., et al., *J. Clin. Invest.*, 97:604–612 (1996); Van Riper, G., et al., *J. Exp. Med.*, 177: 851–856 (1993)). Duplicates were used throughout the experiments and the standard deviations were always <10% of the mean. All experiments were repeated at least three times. Curve fit and concentrations that inhibit 50% specific binding (IC50) were calculated by KALEIDAGRAPH software (Synergy Software, Reading, Pa.).

Measurement of Intracellular Calcium Concentration ($[Ca^{2+}]i$).

50 $\mu$g Fura-2 AM (Molecular Probes, Eugene Oreg.) was dissolved in 44 $\mu$l of DMSO, and this was diluted to 4.4 ml with loading buffer (Hanks Balanced Salt Solution, Gibco/BRL, catalogue #14025-092 containing 2% BSA). Eosinophils were resuspended in loading buffer at $10^7$ cells/ml, and 1.5 ml of cells was mixed with 300 $\mu$l of the Fura-2 solution for 30 minutes at 37° C. Following labeling, excess dye was removed by centrifugation and cells were resuspended at a concentration of $10^6$/ml in 125 mM NaCl, 5 mM KCl, 1 mM $MgCl_2$, 1 mM $CaCl_2$, 0.5 mM glucose, 0.025% BSA and 20 mM HEPES, pH 7.4. $[Ca^{2+}]i$ was measured using excitation at 340 and 380 nm on a Hitachi F-2000 fluorescence spectrometer. Calibration was performed using 1% NP-40 for total release and 25 $\mu$M EGTA to chelate free $Ca^{2+}$.

Results

Figure 18B:
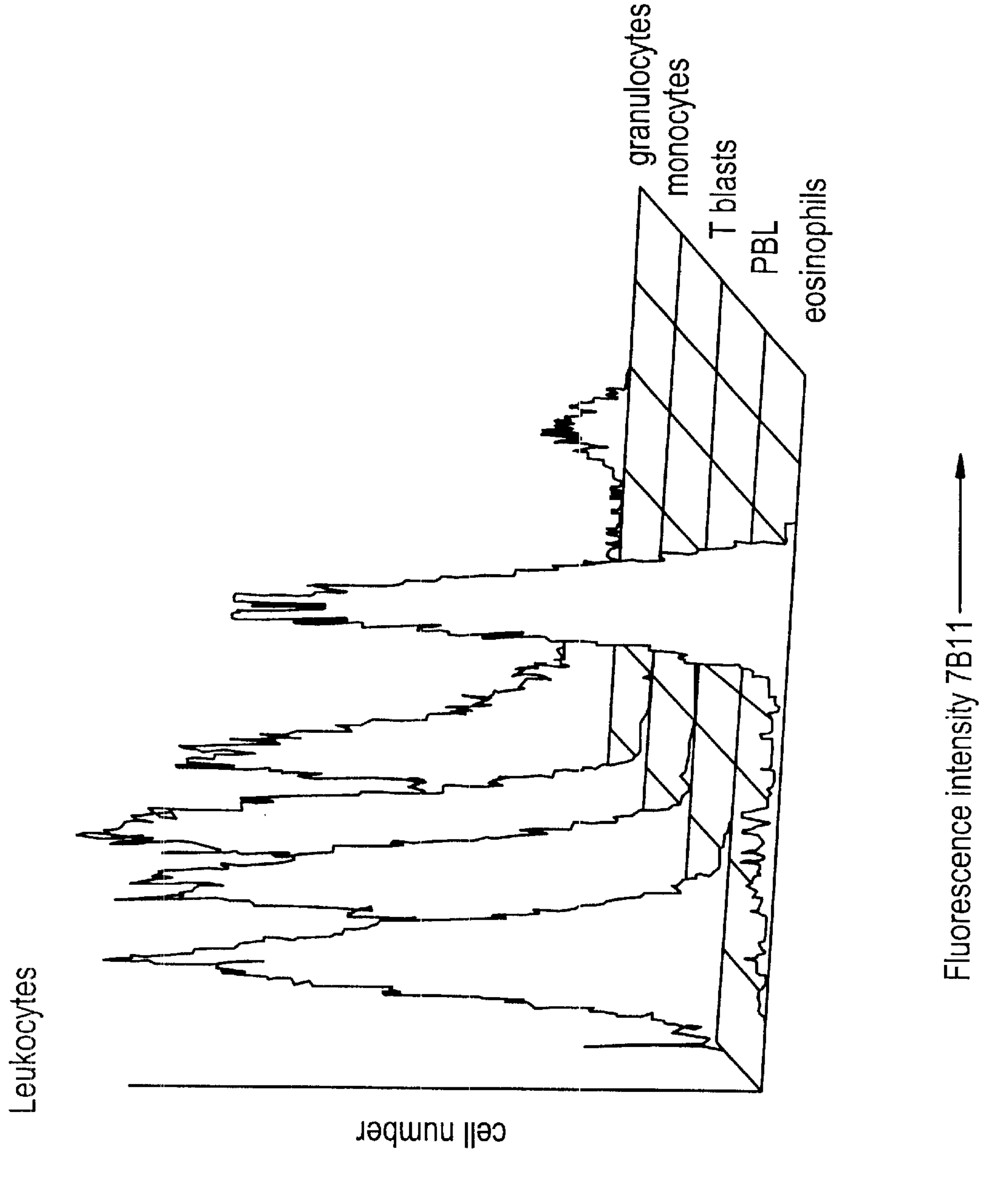
FIG. 18B is a FACs profile of human eosinophils, lymphocytes, T cell blasts, monocytes, and granulocytes stained with mAb 7B11. Staining profiles were representative of at least 4 experiments.
Figure 18C:
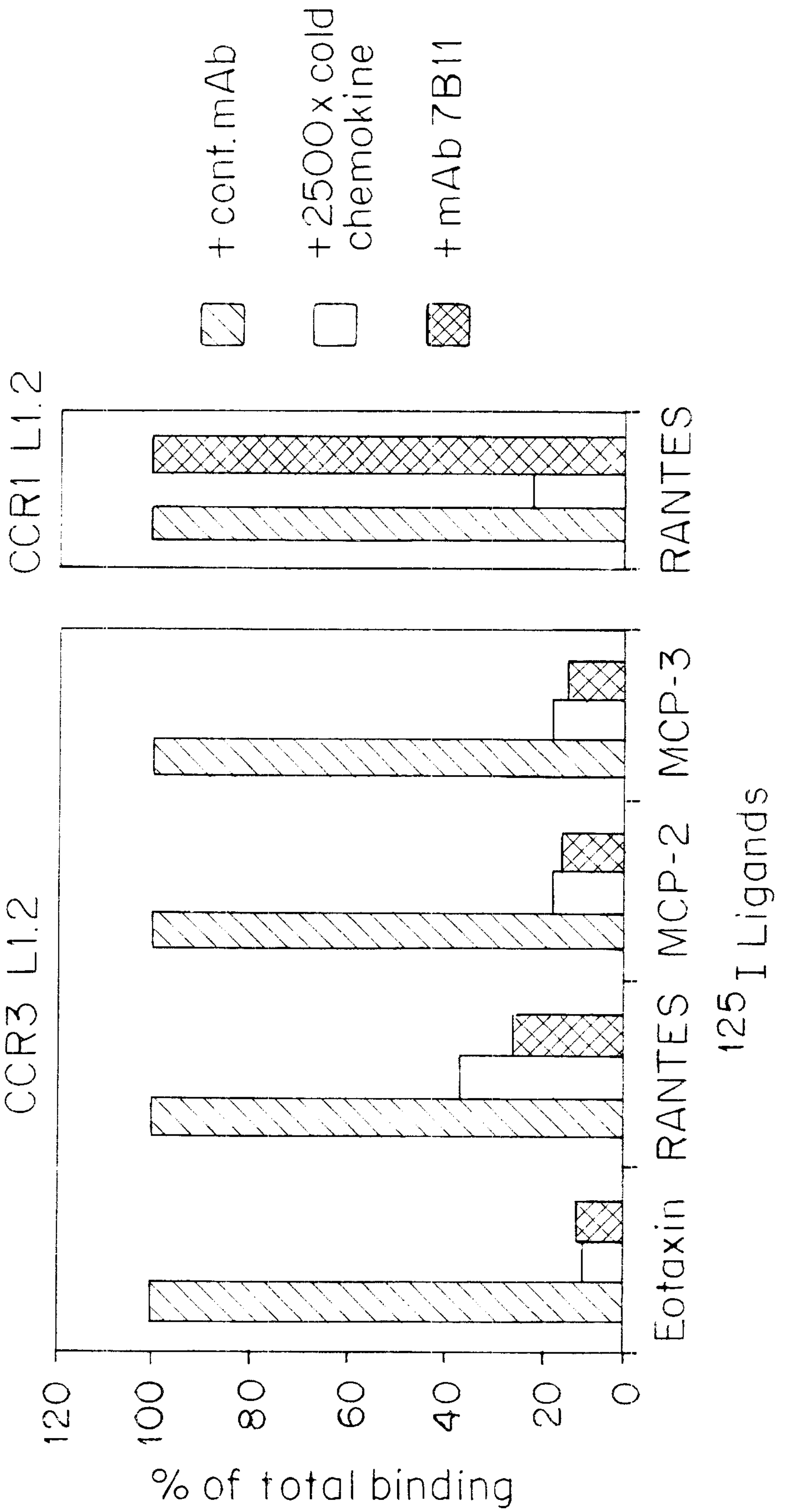
FIG. 18C is a histogram illustrating binding of radiolabeled human eotaxin, RANTES, MCP-2, or MCP-3 to L1.2 CCR3 or CCR1 transfectants, and inhibition by mAb 7B11 or cold chemokines. Cells were incubated with 0.1 nM $^{125}$I-labeled eotaxin, RANTES, or MCP-3, and either 50 μl of 100 μg/ml of irrelevant mAb (MOPC 21), mAb 7B11, or 250 nM cold chemokine. After 60 minutes at room temperature, cell pellets were washed and counted.
Figure 19:
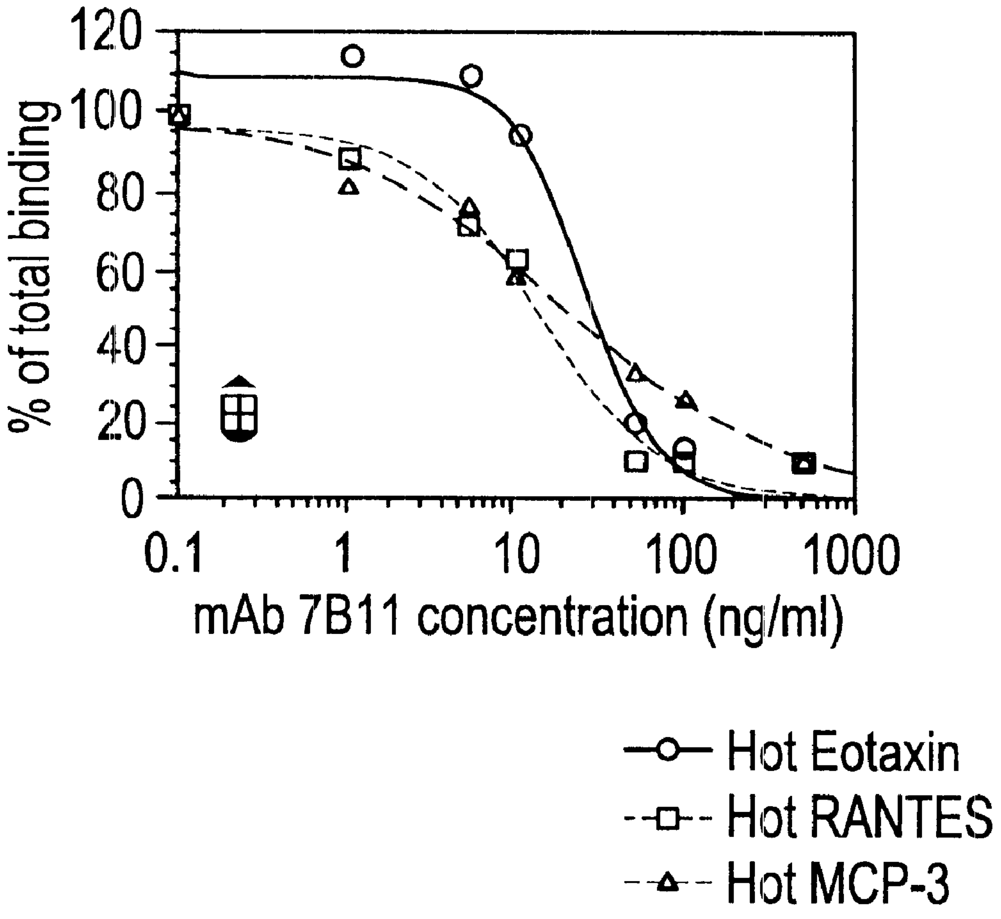
FIG. 19 is a graph illustrating inhibition of binding of radiolabeled eotaxin, RANTES, and MCP-3 to human eosinophils by mAb 7B11. Human eosinophils were incubated with 0.1 nM $^{125}$I-labeled-eotaxin, -RANTES, or -MCP-3, and various concentrations of mAb 7B11. After 60 minutes at room temperature, cell pellets were washed and counted. Data was analyzed by KALEIDAGRAPH software, which calculated an IC50 of eotaxin of 25.7 ng/ml, for RANTES of 13.7 ng/ml, and for MCP-3 of 18.8 ng/ml. The level of inhibition using 250 nM cold chemokine is shown at the bottom left of the plot: ○ eotaxin, □ RANTES, and Δ MCP-3.

Complete blocking of eotaxin, RANTES and MCP-3 binding to CCR3 transfectants using a mAb, 7B11. L1.2 transfectants expressing high levels of CCR3 were selected using the anti-CCR3 peptide mAb 5H12 (Example 5, also referred to herein as LS26-5H12; Ponath, P. D., et al., *J. Clin. Invest.*, 97:604–612 (1996)). mAbs were produced to surface expressed CCR3 and one mAb, 7B11, was identified that reacted with L1.2 cells transfected with CCR3, but not with L1.2 cells transfected with CCR1, CCR2b, CCR4, CCR5, CXCR1, or CXCR2 (FIG. 18A). mAb 7B11 stained human eosinophils intensely (FIG. 18B). This mAb was unreactive with lymphocytes, CD3 activated T cells, and monocytes. Staining on neutrophils was largely negative, although a small percentage of these cells may express very low levels of the receptor. The small subset of granulocytes stained intensely by 7B11 (FIG. 18A) were eosinophils which were contained in the granulocyte gate.

mAb 7B11 was assessed for its ability to inhibit $^{125}$I-labeled-eotaxin, $^{125}$I-RANTES, $^{125}$-MCP-2 and $^{125}$I-MCP-3 binding to CCR3 transfectants. mAb 7B11 inhibited binding completely of $^{125}$I-labeled eotaxin to the transfectants (FIG. 18C), and this inhibition was as efficient as that obtained with 100 nM cold eotaxin. This indicated that mAb 7B11 was able to completely block eotaxin binding to CCR3. This mAb also completely inhibited $^{125}$I-labeled RANTES, $^{125}$I-labeled MCP-3 and $^{125}$I-labeled MCP-2 binding to CCR3 transfectants (FIG. 18C), indicating that the epitope recognized by 7B11 was involved in the binding of numerous CC chemokines. In contrast, mAb 7B11 failed to inhibit RANTES binding to CCR1 transfectants (FIG. 18C).

mAb 7B11 blocks binding of radiolabeled eotaxin, RANTES and MCP-3 to eosinophils. To test if eotaxin, RANTES and MCP-3 binding to eosinophils was occurring through CCR3, binding of radiolabeled chemokines to eosinophils was performed in the presence of various concentrations of the blocking mAb 7B11, or a control mAb (FIG. 19). $^{125}$I-labeled eotaxin binding to eosinophils could be completely inhibited using an appropriate amount of 7B11 mAb, consistent with results indicating that eotaxin binds only to CCR3 on eosinophils (Ponath, P. D., et al., *J. Exp. Med.*, 183:2437–2448 (1996)). However RANTES and MCP-3 are known to bind chemokine receptors in addition to CCR3 (Neote, K., et al., *Cell* 72:415–425 (1993); Gao, J. L., et al., *J. Exp. Med.*, 177:1421–1427 (1993); Ponath, P. D., et al., *J. Exp. Med.*, 183:2437–2448 (1996)). FIG. 19 shows that mAb 7B11 also inhibited $^{125}$I-labeled RANTES and $^{125}$I-labeled MCP-3 binding to eosinophils. 50 ng/ml of mAb 7B11 was sufficient to achieve complete blockade of all chemokine binding to normal eosinophils, similar to the inhibition achieved with 2500-fold excess of cold chemokines. Slightly lower amounts of mAb 7B11 were required to block RANTES and MCP-3 binding, which is consistent with the lower affinity of RANTES and MCP-3 for CCR3 (Ponath, P. D., et al., *J. Exp. Med.*, 183:2437–2448 (1996)).

Figure 20B:
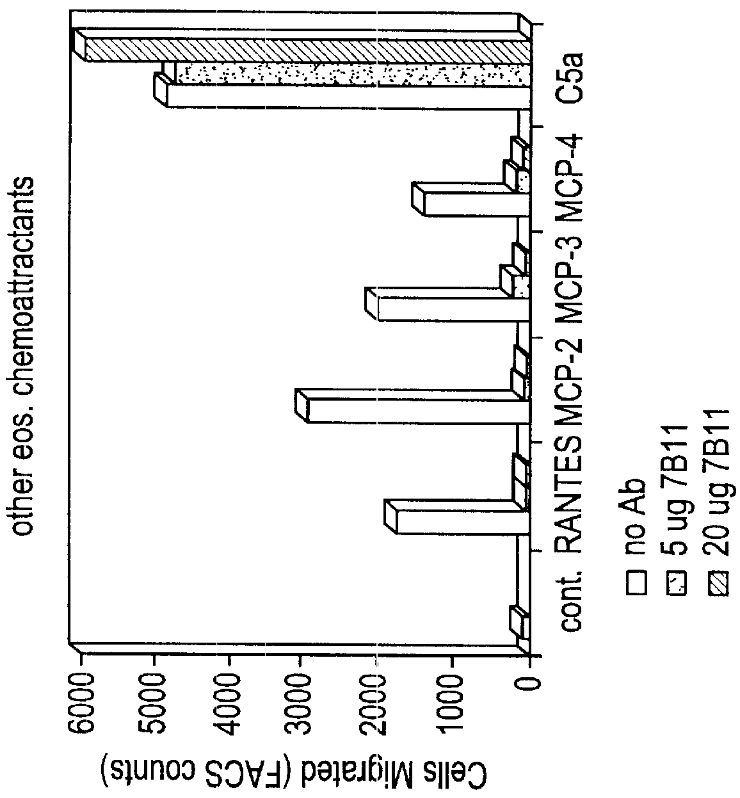
FIG. 20B is a histogram illustrating inhibition of eosinophil chemotaxis to various chemoattractants by 5 μg or 20 μg/ml of 7B11 mAb. For the experiments shown in both 20A and 20B, $1\times10^6$ human eosinophils were placed in the top chamber of the transwell and 10 nM of chemokine was placed in the bottom chamber. Various concentrations of 7B11 mAb were placed in the top well. After 1.5 hours the cells migrating to the bottom chamber were counted using flow cytometry. The results are representative of at least four separate experiments.
Figure 20A:
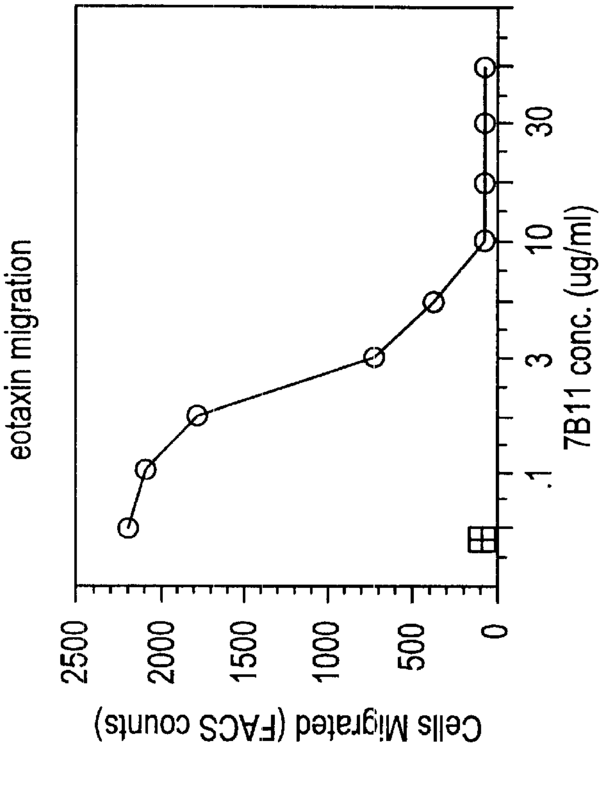
FIG. 20A is a graph illustrating the dose response of mAb 7B11 inhibition of eosinophil chemotaxis to eotaxin. The level of background migration of cells (no chemokine) is shown by the ⊞ symbol (bottom left of the plot).
Figures 21A, 21B, 21C, 21D, 21E, 21F, 21G, 21H, 21I, 21J:
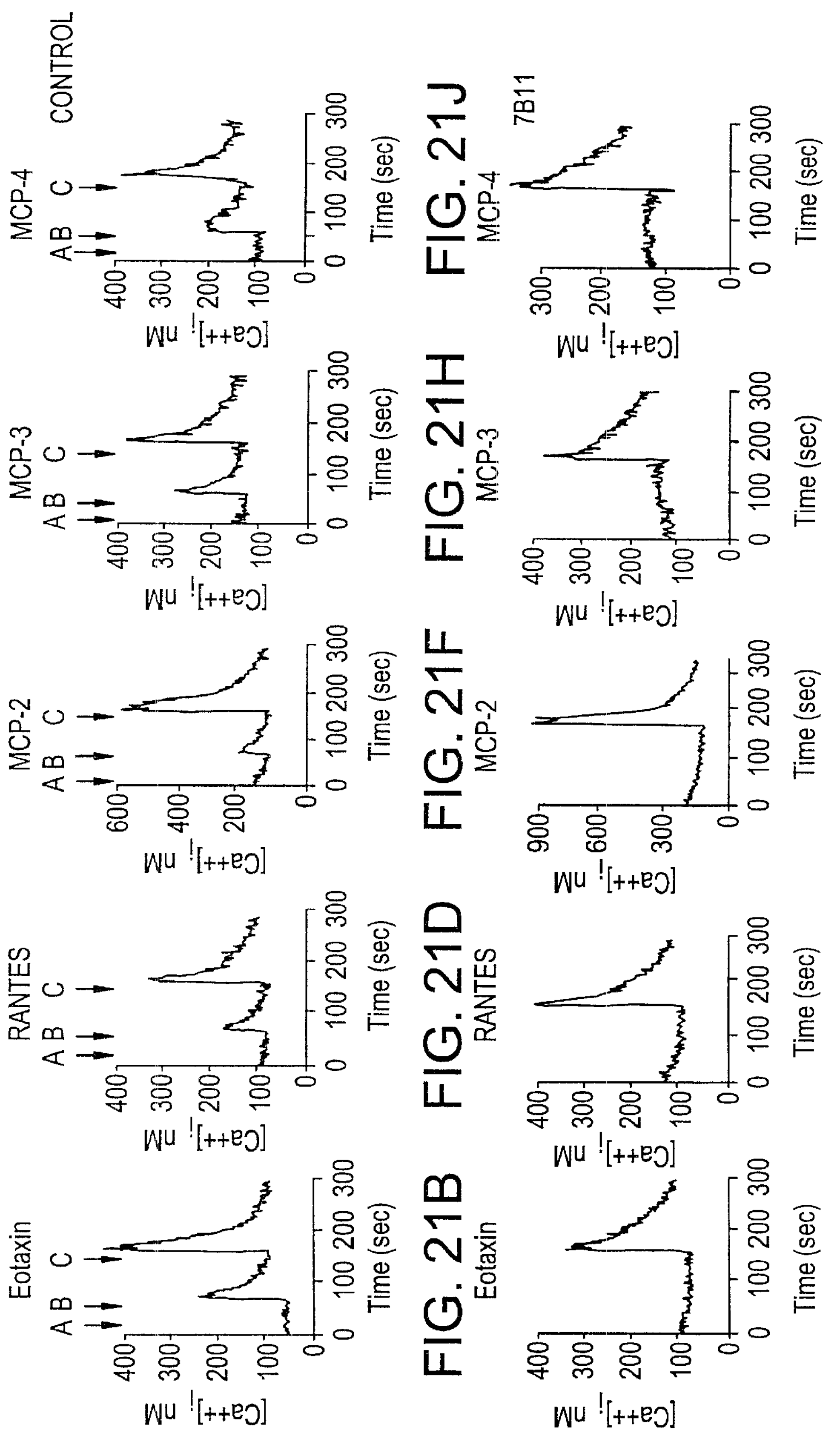
FIGS. 21A–21J are a series of tracings illustrating that mAb 7B11 inhibits $[Ca^{2+}]i$ by human eosinophils in response to eotaxin, RANTES, MCP-2, MCP-3 and MCP-4. Human eosinophils were labeled with Fura-2, and stimulated sequentially with mAb (A), followed 40 sec later with the indicated chemokine (B), and 100 sec following that with C5a (C). $[Ca^{2+}]i$ fluorescence changes were recorded using a spectrofluorimeter. The tracings are representative of five separate experiments, performed with eosinophils from different donors. In the top panels, an irrelevant control mAb (MOPC-21) was used, and in the bottom panels, mAb 7B11. Antibodies were used at a final concentration of 6.4 μg/ml Chemokines were used at: eotaxin, 10 nM, RANTES, 20 nM, MCP-2, 200 nM, MCP-3, 200 nM, MCP-4, 10 nM. C5a was used at 400 pM.

Inhibition of eosinophil chemotaxis to CC chemokines using anti-CCR3 mAb. Chemotaxis experiments were performed using eosinophils from normal individuals with moderately high levels of eosinophils (~3 to 6% of WBC). FIG. 20A shows that mAb 7B11 was able to inhibit completely the chemotaxis of eosinophils to eotaxin in a dose dependent manner. 5–10 ug/ml was required to achieve 100% inhibition, using 100 ng/ml (12.5 nM) of chemokine in the bottom well. FIG. 20B shows that the eosinophil chemotactic responses to RANTES, MCP-2, MCP-3, and MCP-4 could be inhibited totally using 5–10 ug/ml of mAb 7B11. 7B11 was unable to inhibit eosinophil chemotaxis to C5a (FIG. 20B). Moreover, mAb 7B11 was unable to inhibit PBMC chemotaxis to RANTES, which occurs through chemokine receptors other than CCR3. Donor to donor variation in eosinophil chemotactic responses to chemokines has been observed (Ponath, P. D., et al., *J. Exp. Med.*, 183:2437–2448 (1996)). However, in all individuals examined thus far (n=8), mAb 7B11 was able to inhibit by >95% the migration of eosinophils to eotaxin, RANTES, MCP-2, MCP-3, and MCP-4.

MAb 7B11 inhibits changes in $[Ca^{2+}]i$ by eosinophils in response to cc chemokines. Eotaxin, RANTES, MCP-2, MCP-3 and MCP-4 induce changes in $[Ca^{2+}]i$ by human eosinophils (Ponath, P. D., et al., *J. Clin. Invest.*, 97:604–612 (1996); Uguccioni, M., et al., *J. Exp. Med.*, 183:2379–2384 (1996)). To examine the agonist/antagonist function of mAb 7B11, eosinophils were assessed for $[Ca^{2+}]i$ following injection of mAb 7B11, or an irrelevant control mAb. Eosinophils incubated with the irrelevant mAb still produced changes in $[Ca^{2+}]i$ following injection of optimal amounts of eotaxin, RANTES, MCP-2, MCP-3 and MCP-4 (FIGS. 21A, 21C, 21E, 21G and 21I). C5a, a potent stimulator of eosinophil $[Ca^{2+}]i$, was used as a control.

Eosinophils incubated with 6.4 $\mu$g/ml of 7B11 mAb for 40 seconds were unable to respond to eotaxin, RANTES, MCP-2, MCP-3 and MCP-4 (FIGS. 21B, 21D, 21F, 21H and 21J). This inhibition was not due to receptor modulation from the cell surface, since this effect was rapid, and immunofluorescent staining of eosinophils incubated with mAb 7B11 at room temperature revealed intense staining. In addition, mAb7B11 was antagonistic rather than agonistic, since concentrations as high as 10 $\mu$g/ml of mAb failed to induce a change in $[Ca^{2+}]i$. 7B11 treated eosinophils showed changes in $[Ca^{2}]i$ to C5a. mAb 7B11 had no effect on the $[Ca^{2+}]i$ of butyrate differentiated HL-60 cells to MIP-1α or RANTES, a response that is mediated through receptors other than CCR3.

Figure 22A:
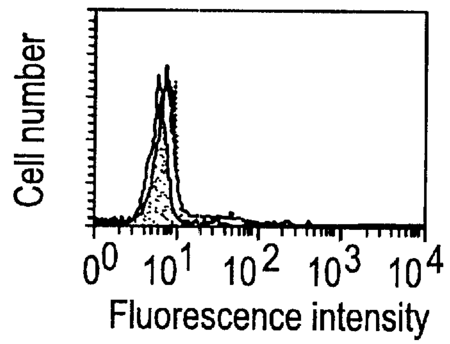
FIG. 22A is a FACs profile illustrating IL-8 receptor expression on freshly isolated eosinophils from a healthy individual. Eosinophils were stained with mAbs to CXCR1 (solid line), CXCR2 (dotted line) or a control mAb (shaded), and were analyzed by flow cytometry.
Figure 22B:
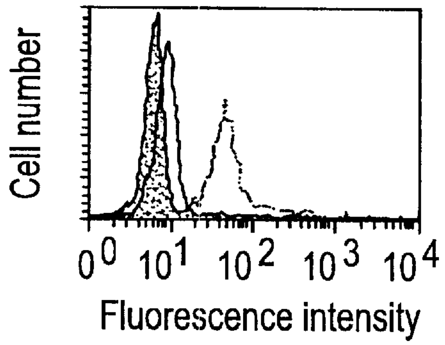
FIG. 22B is a FACs profile illustrating IL-8 receptor expression on IL-5 treated eosinophils. Eosinophils cultured with IL-5 for 5 days were stained with mAbs, as in FIG. 22A.
Figure 22C:
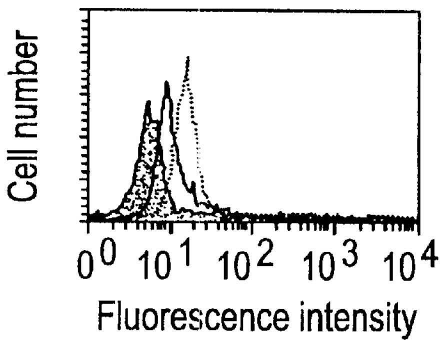
FIG. 22C is a FACs profile illustrating IL-8 receptor expression on eosinophils isolated from an eosinophilic individual, and stained with mAbs, as in FIGS. 22A and 22B.
Figure 22D:
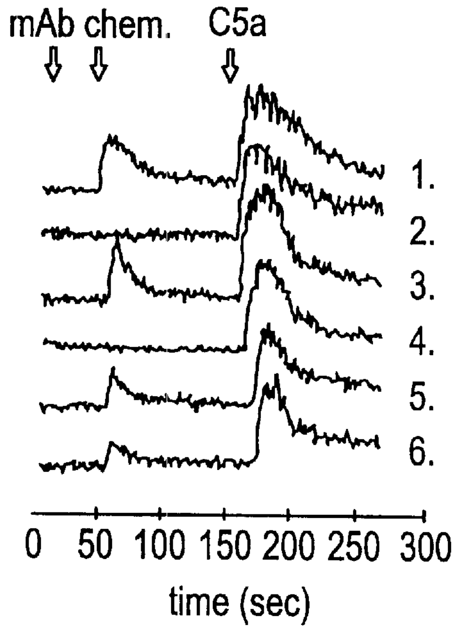
FIG. 22D are tracings illustrating inhibition of $[Ca^{2+}]i$ of day 5 IL-5 primed eosinophils to various chemokines by mAb 7B11. Methods were the same as those described in the legend of FIG. 21. The mAbs and chemokines used were: 1. control mAb, eotaxin, C5a; 2. 7B11, eotaxin, C5a; 3. control mAb, RANTES, C5a; 4. 7B11, RANTES, C5a; 5. control mAb, IL-8, C5a; 6. 7B11, IL-8, C5a. The results are representative of at least three separate experiments.

IL-5 primed eosinophils respond to CC chemokines through CCR3 but upregulate IL-8 receptors. Eosinophils from eosinophilic individuals, and normal eosinophils primed in vitro with IL-5, respond to IL-8 in chemotaxis assays (Schweizer, R. C., et al., *Blood*, 83:3697–3704 (1994); Sehmi, R., et al., *Clin. Exp. Allergy*, 23: 1027–1034 (1994)), suggesting that activated eosinophils have altered chemokine receptor expression. To test whether primed or activated eosinophils respond to CC chemokines in the same manner as do normal eosinophils, blocking experiments similar to those shown in FIGS. 20 and 21A–21J. were performed using day 5 to 7 IL-5 stimulated eosinophils, and eosinophils from an eosinophilic individual. The IL-8 receptors, CXCR1 and CXCR2, were undetectable by mAb staining on eosinophils from all normal individuals examined (n=12) (FIG. 22A). However following 5–7 days in culture in vitro with human IL-5, CXCR2 and (to a lesser degree) CXCR1 were detectable on the surface of eosinophils, as detected using anti-CXCR2 mAbs and flow cytometry (FIG. 22B), and this expression paralleled the ability of these eosinophils to migrate to IL-8 in chemotaxis assays (not shown). In the one eosinophilic donor examined (18–25% of WBC were eosinophils, for >1 year), CXCR2 was expressed on eosinophils at a slightly lower level (FIG. 22C).

mAb 7B11 was still able to block completely the calcium responses of both IL-5 primed eosinophils (FIG. 22D), and eosinophils from the eosinophilic donor, to eotaxin and RANTES (FIG. 22D), as well as MCP-2, MCP-3, and MCP-4, in a similar fashion to that described for normal eosinophils. mAb 7B11 had no effect on IL-8 responses (FIG. 22D), and MIP-1α responses were not evident in these experiments. CCR3 expression was assessed on the IL-5 primed eosinophils, and from eosinophils from numerous healthy individuals. The number of 7B11 binding sites per eosinophil from healthy individuals was calculated to be 17,400±1600 (n=12), and no significant differences were observed following IL-5 stimulation. However in the one eosinophilic donor analyzed, the number of 7B11 binding sites was found to be 26,000.

DISCUSSION

The functional effects of all of the efficacious chemokines for eosinophils characterized, including eotaxin, RANTES, MCP-2, MCP-3, and MCP-4, could be blocked completely with an anti-CCR3 mAb with potent antagonistic activity. This mAb was specific for CCR3, and no inhibitory effects on other chemoattractant receptors were observed. These results further establish that CCR3 is the principal receptor for eosinophil responses to CC chemokines, and questions an essential role for CCR1, CCR2, CCR4 or CCR5.

The predominant CC chemokine receptor on eosinophils is CCR3. This receptor is expressed at a high level, as shown by ligand binding studies and mAb staining. A recent study suggested that human eosinophils express MIP-1α receptors, either CCR1, CCR4 or CCR5, at about 1–5% of the levels of CCR3 (Daugherty, B. L., et al., *J. Exp. Med.*, 183:2349–2354 (1996)), and modest eosinophil chemotactic responses towards MIP-1α have been observed in some individuals ( see above; Ponath, P. D., et al., *J. Exp. Med.*, 183:2437–2448 (1996); Ponath, P. D., et al., *J. Clin. Invest.*, 97:604–612 (1996)). However, the results using MAB7B11 indicate MIP-1α receptor(s) contribute little to the functional responses of eosinophils to RANTES or MCP-3. Donor variation was observed in eosinophil responses to the CC chemokines, however these responses were blocked completely in all individuals, using mAb 7B11, indicating that if other CC chemokine receptors are present, they have a minor functional significance. In addition, responses of IL-5-stimulated eosinophils to CC chemokines could also be blocked by mAb 7B11, suggesting that no new receptors were upregulated on cytokine primed eosinophils, as happens for IL-2 primed T cells (Loetscher, P., et al., *J. Exp. Med.*, 184:569–577 (1996)). The relevance of IL-8 receptors on IL-5 primed or activated eosinophils is uncertain. The phenotypic and functional analyses described herein are consistent with previous reports showing that IL-5 stimulated eosinophils, or eosinophils from eosinophilic donors, respond to IL-8 in chemotaxis assays (Schweizer, R. C., et al., *Blood*, 83:3697–3704 (1994); Sehmi, R., et al., *Clin. Exp. Allergy*, 23:1027–1034 (1994)).

Thus, as described herein, a fully antagonistic mAb to a CC chemokine receptor has been identified. A CCR3 antagonist has application in the treatment of diseases such as asthma, where an inhibition of eosinophil migration to the airways is beneficial. The role of Eotaxin-CCR3 in eosinophil migration to the airways in asthma is suggested since a selective recruitment of eosinophils often occurs in this disease. Moreover, eotaxin and other chemokines are highly upregulated in the airways of asthma patients (J. Rottmann and D. Ringler), as well as in animal models of allergic airway disease (Jose, P. J., et al., *J. Exp. Med.*, 179:881–887 (1994); Gonzalo, J.-A., et al., *Immunity*, 4:1–14 (1996)).

EXAMPLE 11

Blockade of eosinophil deqranulation induced by eotaxin, RANTES and MCP-3 by anti-CCR3 monoclonal antibody 7B11. Effect of anti-CCR3 monoclonal antibody 7B11 on C5a-induced eosinophil degranulation.

Eosinophil degranulation stimulated by eotaxin, RANTES, MCP-3 or C5a was measured by the release of eosinophil peroxidase into the media (EPO) after stimulation with either eotaxin, RANTES, MCP-3 or C5a. EPO is an eosinophil enzyme present in eosinophilic specific granules.

The present study shows that the anti-CCR3 monoclonal antibody 7B11 inhibits the eosinophil degranulation stimulated by the CCR3 chemokines eotaxin, RANTES and MCP-3, while it has no effect on eosinophil degranulation stimulated by C5a. C5a binds to a different receptor and thus it serves as a negative control.

Materials and Methods

Hank's Balanced Salt Solution (HBSS, Cat. No. 14025-092) and Dulbecco's Phosphate Buffered Saline (PBS, Cat. No. 14190-144) were from Gibco BRL. Cytochalasin B (C-6762), Hydrogen Peroxide ($H_2O_2$, 3% solution, H-6520), DMSO (D-5879), Tris(hydroxymethyl)amino methane (T-1503) and o-phenylenediamine (P2903) were from Sigma Chemical Co., (St. Louis, Mo.). Polystyrene V or round bottom plates were from Costar. Purified human eosinophils were prepared as described above.

Eosinophil Degranulation Assay and Blockade by the Monoclonal Antibody 7B11.

7B11 antibody solutions were prepared in PBS at 1 and 0.1 mg/ml (100×assay final concentrations). Chemokine or C5a were dissolved in HBSS, 25 mM Hepes, 0.25% BSA buffer (assay buffer) at 2×assay final concentrations.

Eosinophils were resuspended at $2.5\times10^6$/ml in assay buffer (HBSS, 25 mM Hepes, 0.25% BSA). A 1:1000 volume of a 5 mg/ml cytochalasin B solution in 100% DMSO was added to the eosinophil suspension (5 μg/ml final concentration). 100 μl of the cell suspension were then dispensed into 96 well V bottom plates ($0.25 \times 10^6$ cells per well). 2 μl of either PBS or antibody solution (1 or 0.1 mg/ml for the 10 or 1 ug/ml final antibody concentrations, respectively) were added to the cells and the plates were placed in a 37° C. incubator for 10 min. After incubation, 100 μl of chemokine solution or buffer alone were added to the cells and incubated for 30 min. After incubation the plates were centrifuged for 5 min at 160 g at 10° C. After centrifugation supernatants were collected and assayed for the presence of eosinophil peroxidase as described below. Assays were normally performed in duplicate.

Eosinophil Peroxidase Assay.

Analysis of EPO concentrations were carried out following the protocol described in White, S. R., et al., *J. Immunol. Meth.*, 44:257–263 (1991) with some modifications. This assay is based on the oxidation of o-phenylenediamine by EPO in the presence of $H_2O_2$. Assay final concentrations of substrate and $H_2O_2$ were 16 mM and 0.01%, respectively. The substrate stock solution (27 mM substrate, 0.016% $H_2O_2$) was prepared immediately prior to use in 0.1 M Tris pH 8.0, 0.1% Triton X-100. Briefly, 75 μl of substrate solution were combined with 50 μl of sample in a flat bottom 96 well plate immediately prior to obtaining readings at 492 nm every 15 sec for 5 min. Spectrophotometric readings were performed in a microplate absorbance spectrophotometer (Dynatech MR 4000, Dynatech Laboratories, INC., Chantilly, Va). Data was collected and analyzed using the assay management software Biolinx TM version 2.1. The velocity of the reaction was calculated by interpolation between successive 3 or 4 points. Horseradish peroxidase (HRP) was used as standard. Kinetic data were extrapolated to a standard curve obtained with 2, 5, 10 and 20 ng of HRP and the activity expressed in units of EPO per million cells, with one unit corresponding to the activity that is equivalent to the activity of 1 ng of HRP. Thus, a unit of EPO is defined as the amount of protein that would give the same activity as 1 ng of HRP.

RESULTS

Figure 23A:
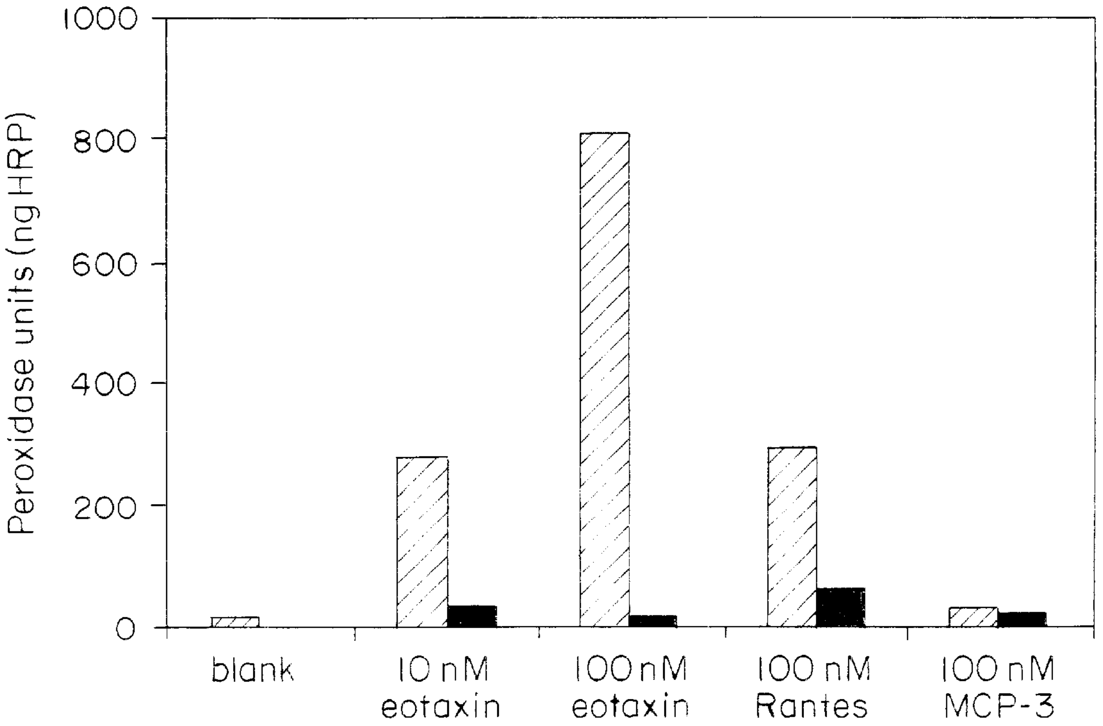
FIG. 23A is a histogram illustrating blockade of eotaxin-, RANTES- and MCP-3-induced eosinophil peroxidase (EPO) release by monoclonal antibody 7B11. Cross hatched bars indicate the amount of EPO released by either 10 nM eotaxin, 100 nM eotaxin, 100 nM RANTES or 100 nM MCP-3. Black bars indicate the amount of EPO released when 10 μg/ml of7B11 was present in the eosinophil degranulation assay. The bar marked "blank" corresponds to a no chemokine, no antibody (buffer) control.
Figure 23B:
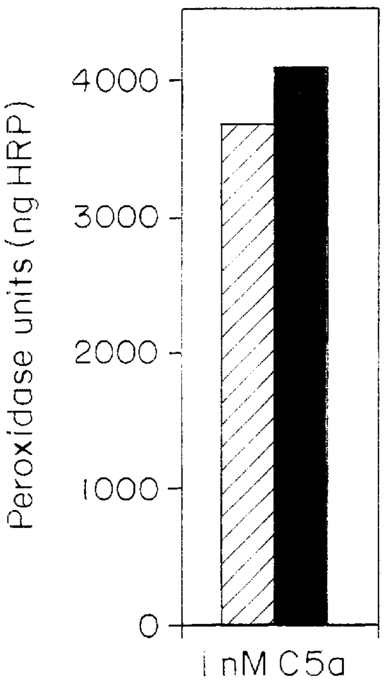
FIG. 23B is a histogram illustrating the effect of mAb 7B11 on C5a-induced eosinophil peroxidase release. The cross hatched bar indicates the amount of EPO released by 1 nM C5a. The black bar indicates the amount of EPO released when 10 μg/ml of 7B11 was present in the eosinophil degranulation assay.

In two separate experiments, the mAb 7B11 blocked eotaxin-induced peroxidase release from eosinophils. FIG. 23A shows that 7B11 at a concentration of 10 μg/ml significantly inhibited the degranulation induced by 10 or 100 nM eotaxin and by 100 nM RANTES or MCP-3. Degranulation induced by 100 nM eotaxin, RANTES or MCP-3 was inhibited by 99, 77 and 72%, respectively. Degranulation induced by 10 nM eotaxin was inhibited to 65% and 85% by 1 and 10 μg/ml of 7B11, respectively. Significantly, as shown in FIG. 23B, the mAb 7B11 did not inhibit the degranulation induced by C5a.

Figure 24A:
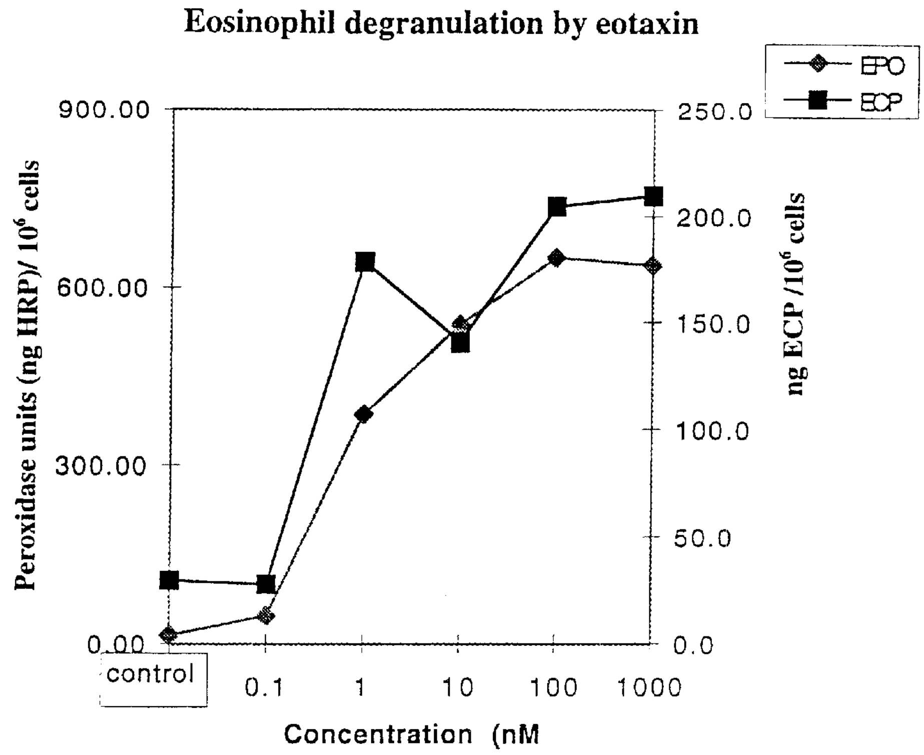
FIG. 24A is a graph illustrating eosinophil degranulation induced by eotaxin measured by release of eosinophil peroxidase (EPO) and eosinophilic cationic protein (ECP).
Figure 24B:
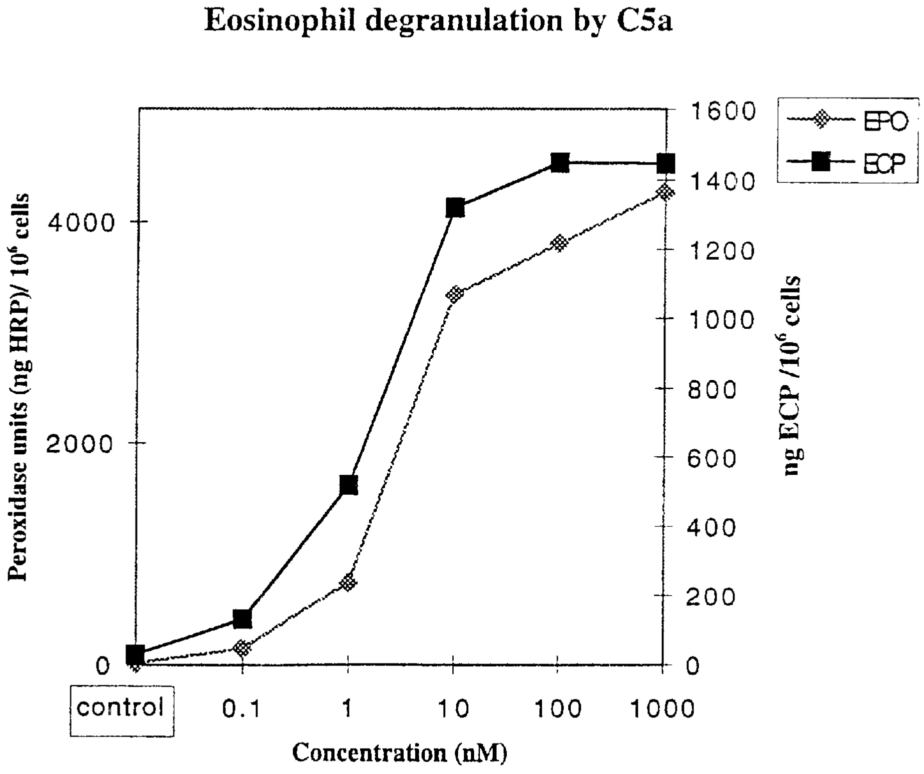
FIG. 24B is a graph illustrating eosinophil degranulation induced by C5a measured by release of eosinophil peroxidase (EPO) and eosinophilic cationic protein (ECP).
Figure 25:
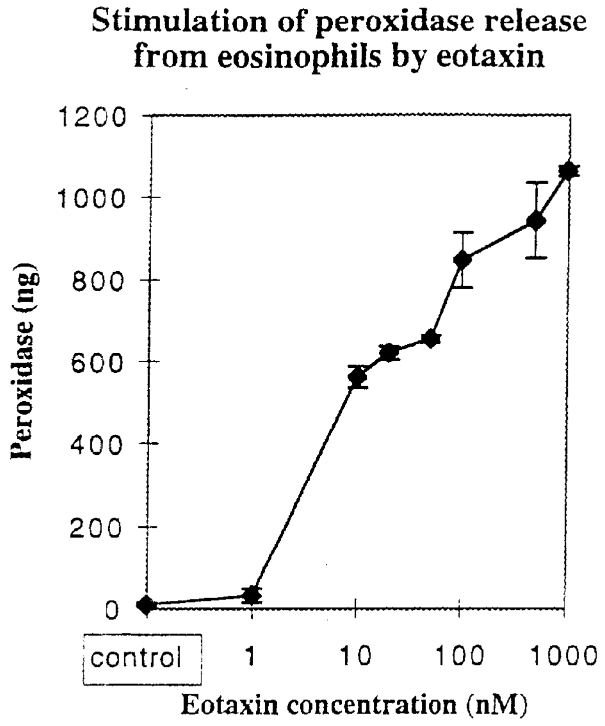
FIG. 25 is a graph illustrating stimulation of peroxidase release from eosinophils by eotaxin.
Figure 26:
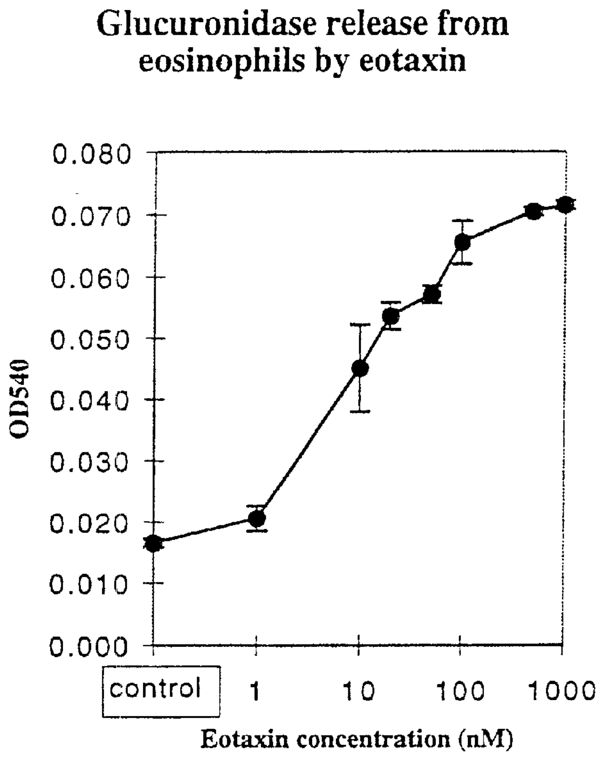
FIG. 26 is a graph illustrating stimulation of glucuronidase release from eosinophils by eotaxin.
Figure 27:
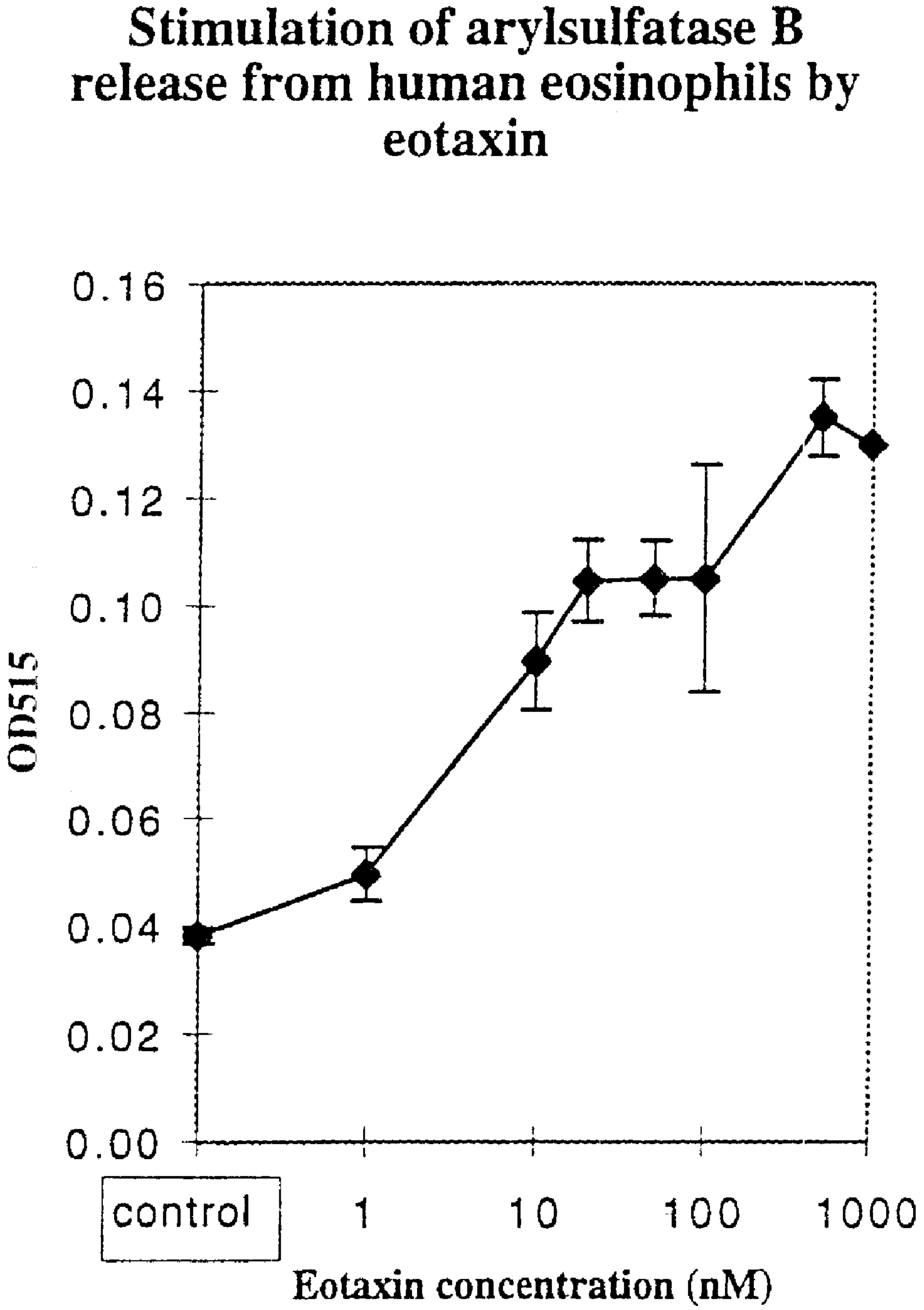
FIG. 27 is a graph illustrating stimulation of arylsulfatase B release from human eosinophils by eotaxin.

Previous studies showed that eotaxin stimulated release of EPO parallels the release of other eosinophilic granule enzymes and proteins such as eosinophil cationic protein (ECP) (FIG. 24A), glucuronidase and arylsulfatase B (FIGS. 25–27). EPO, ECP and glucuronidase are present in eosinophil specific granules and arylsufatase B is present in small granules. Thus, eotaxin induces degranulation of both specific and small granules. FIGS. 25–27 and show that the eotaxin dose response curves for EPO release parallel the dose response curves for the release of other eosinophilic proteins. These assays were essentially performed as described in the materials and methods for the eosinophil degranulation assay. The supernatants were then assayed for the presence of eosinophil granule proteins using established procedures. For ECP a commercially available radioimmunoassay kit was used (Pharmacia Diagnostics, Cat. No. 10-9165-01). Enzyme assays for glucuronidase and arylsulfatase B are described in Kroegel, C., et al., *J. of Immunol.*, 142:3518–3526 (1989).

EPO was the enzyme of choice in eosinophil degranulation studies because of convenience of assay and quantitation. EPO release by eotaxin is a reflection of eosinophil degranulation in general. Because EPO release is paralleled by the release of other eosinophil proteins and enzymes, similarly, 7B11 blockade of degranulation induced by eotaxin as measured by blockade of EPO release, should also be reflected in blockade of release of other eosinophil proteins and enzymes.

EXAMPLE 12

Basophils Express CCR3

Materials and Methods

Flow Cytometry. Cells expressing CCR3 in whole blood were identified by flow cytometry. 100 μl of heparinized whole blood was stained with 400 ng of a 7B11 (anti-CCR3)-FITC preparation and 500 ng of biotin coupled anti-human IgE (PharMingen, San Diego, Calif.) in the presence of 100 μl of PBS with 0.1% azide at room temperature for 20–30 minutes. Cells were washed once in PBS with azide and stained with 5 μl Streptavidin-Quantum Red (Sigma Immuno Chemicals, St. Louis, Mo.) for 15–30 minutes at room temperature. Red cells were lysed using 2 ml of an ammonium chloride lysing buffer and leukocytes were pelleted and resuspended in PBS for analysis on a FACSCAN flow cytometer (Becton Dickinson, Mountainview, Calif.). Visual analysis of cells from the stained populations was performed after sorting cells, stained as above, using a FACSVANTAGE flow cytometer (Becton Dickinson), and preparing Diff Quik (Baxter Scientific Products, McGaw Park, Ill.) stained slides of the collected cells.

Enumeration of number of sites/cell. Cells were stained as above for flow cytometry. After analysis of the sample, tubes containing Quantum 26 beads (Flow Cytometry Standards Corp., San Juan, PR) were used to calibrate fluorescence. The MFSF/protein ratio for the 7B11/FITC preparation was determined using Simply Cellular beads (Flow Cytometry Standards Corp.). Median channel fluorescence of the stained cells was then used to calculate the mean number of bound antibody molecules/cell.

Results

Figure 28:
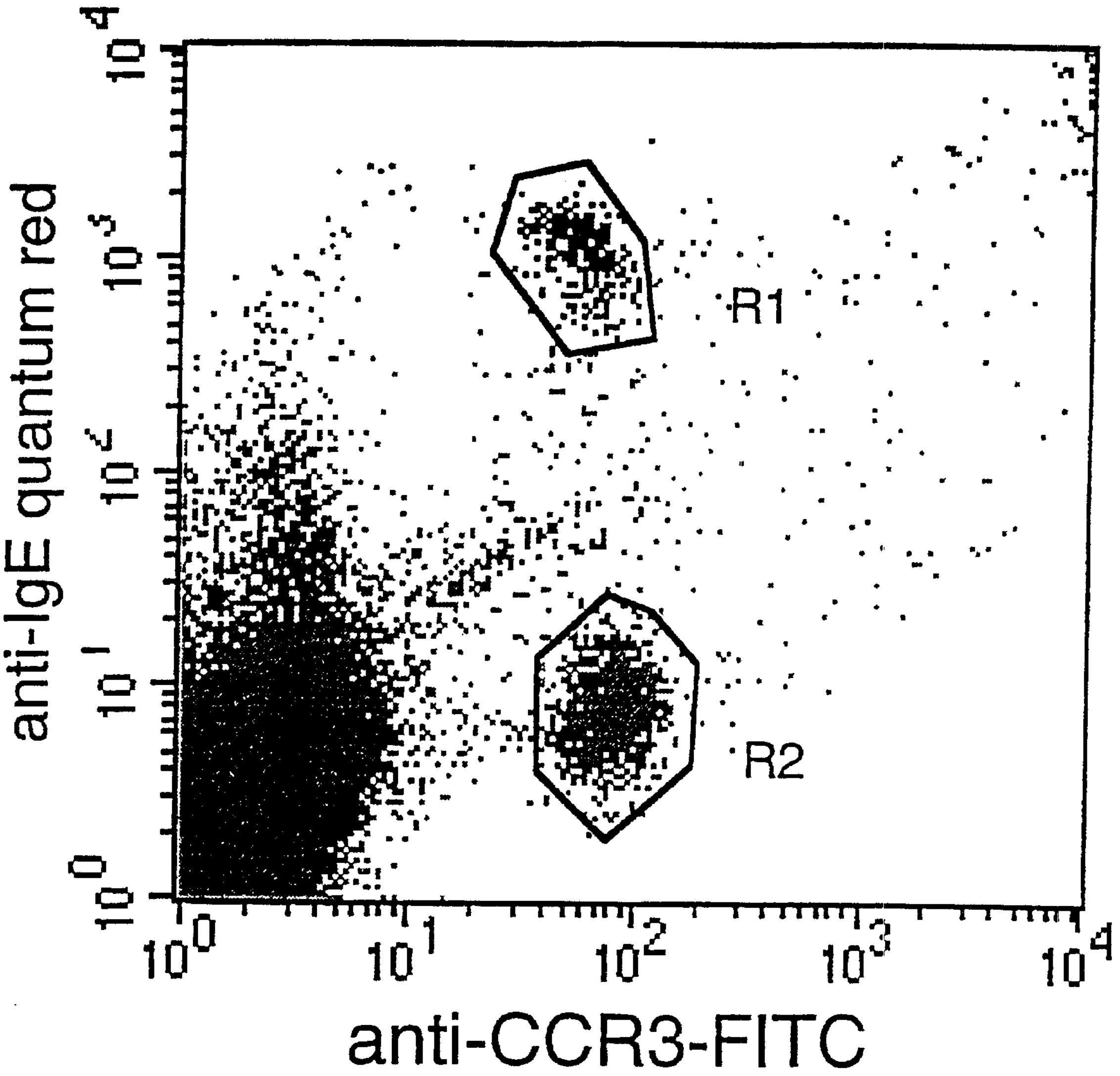
FIG. 28 illustrates expression of CCR3 on eosinophil and basophils in whole blood. Whole blood was stained with 7B11-FITC and anti-human IgE biotin followed by Streptavidin quantum Red as described in Example 12 and analyzed by flow cytometry.

The monoclonal antibody 7B11 previously shown to recognize CCR3, recognized only two populations of cells from whole blood preparations (FIG. 28). One of these populations could be shown to have high levels of IgE on its surface, the other did not. Sorted cells lacking IgE, but stained with 7B11 were 97.3%+0.6 eosinophils as identified on slides prepared from sorted cells. Cells bearing high levels of IgE on their surfaces and also stained by 7B11 appeared on stained preparations to be basophils (92%+4.6), although the method of IgE staining, cell lysis and sorting of the samples led to degranulation of the majority of the cells. Eosinophil consistently expressed slightly higher numbers of receptors/cell than basophils from a given individual ($p<0.001$, paired t-test). From analysis of 30 individuals, the average number of 7B11 binding sites/eosinophil was found to be 24,700±5700; the average number of sites/basophils was 19,000±4500.

Whole blood was stained with 7B11-FITC and anti-human IgE-biotin followed by streptavidin Quantum red and analyzed by flow cytometry. Analysis of the two color staining from whole blood indicated two populations bearing CCR3 (FIG. 28), one of these populations was double stained with anti-human IgE. Comparisons of the intensity of staining by anti-CCR3 antibody indicated that eosinophils consistently stained more intensely than basophils for expression of CCR3. Identity of cells in these two populations was confirmed by conventional histological staining and the $IgE^{(+)}$ CCR3 (+) population was found to be basophils (degranulated), while the IgE (−) CCR3 (+) population was eosinophils. Forward and side scatter using backgating of the two populations indicated that these cells light scatter properties consistent with other indications of their cell type.

EXAMPLE 13

Basophil Chemotaxis to Eotaxin and MCP-4 is Blocked by Anti-CCR3 mAb

Leukocytes were obtained from unselected healthy volunteers after informed consent, and were isolated and fractionated by discontinuous density centrifugation as described (Kurimoto, Y., et al., *J. Exp. Med.*, 170:467 (1989); Bischoff, S. C., et al., *Blood*, 79:2662 (1990)). Briefly, venous blood was anticoagulated with 10 mM EDTA, mixed with 0.25 volume of dextran (6% in NaCl 0.9%), and erythrocytes were allowed to sediment at room temperature. After 90 min, the leukocytes were collected and washed 3 times in HA buffer (20 mM Hepes, 125 mM NaCl, 5 mM KCl, 0.5 mM glucose, 0.025% bovine serum albumin). To enrich for basophil granulocytes, leukocytes were fractionated by Ficoll Hypaque density centrifugation exactly as described (Kurimoto, Y., et al., *J. Exp. Med.*, 170:467 (1989)). Purified basophile were obtained by leukocyte fractionation by discontinuous Percoll gradient centrifugation (Bischoff, S. C., et al., *Blood*, 79:2662 (1990)). The basophil-rich cell layer was collected, washed in HA buffer, resuspended in 150 ul HA buffer, and incubated for 40 min with paramagnetic beads coated with mAb against CD3 (12 ul), CD4 (15 ul), CD8 (12 ul), CD14 (5 ul), CD16 (5 ul) and CD19 (5 ul). The magnetically stained cell suspension was passed over a separation column placed in a strong magnetic field to eliminate contaminating cells (MACS system, Miltenyi Biotec GmbH, Bergisch Gladbach, FRG). The combination of Percoll gradient centrifugation and negative selection with immunomagnetic beads yielded basophil preparations of 80–95% purity (contaminated exclusively by small lymphocytes) with a recovery of 30–60% (as determined by cytocentrifuge slides stained with May Gruenwald/Giemsa and measurements of total histamine contents). Cells were finally washed 3 times in HA buffer and resuspended in HACM buffer (HA buffer supplemented with 1 mM $MgCl_2$ and 1 mM $CaI_2$).

Histamine and $LTC_4$ release.

Basophil (80–180×$10^3$/ml) in 20 mM Hepes, pH 7.4 containing 125 mM glucose and 0.025% BSA were warmed to 37° C., exposed to IL-3 (10 ng/ml) with or without anti-CCR3 (5 ug/ml) and then challenged. After 20 min the tubes were placed on ice and histamine and $LTC_4$ were measured in the supernatant (Dahinden, C. A., et al., *J. Exp. Med.*, 179:751 (1994)). Histamine release was expressed as percent of the total content of the sample (determined after cell lysis). $LTC_4$ generation was expressed as picograms $LTC_4/D_4$ /$E_4$ per nanogram total histamine (which corresponds to 1,000 basophils).

Figure 29:
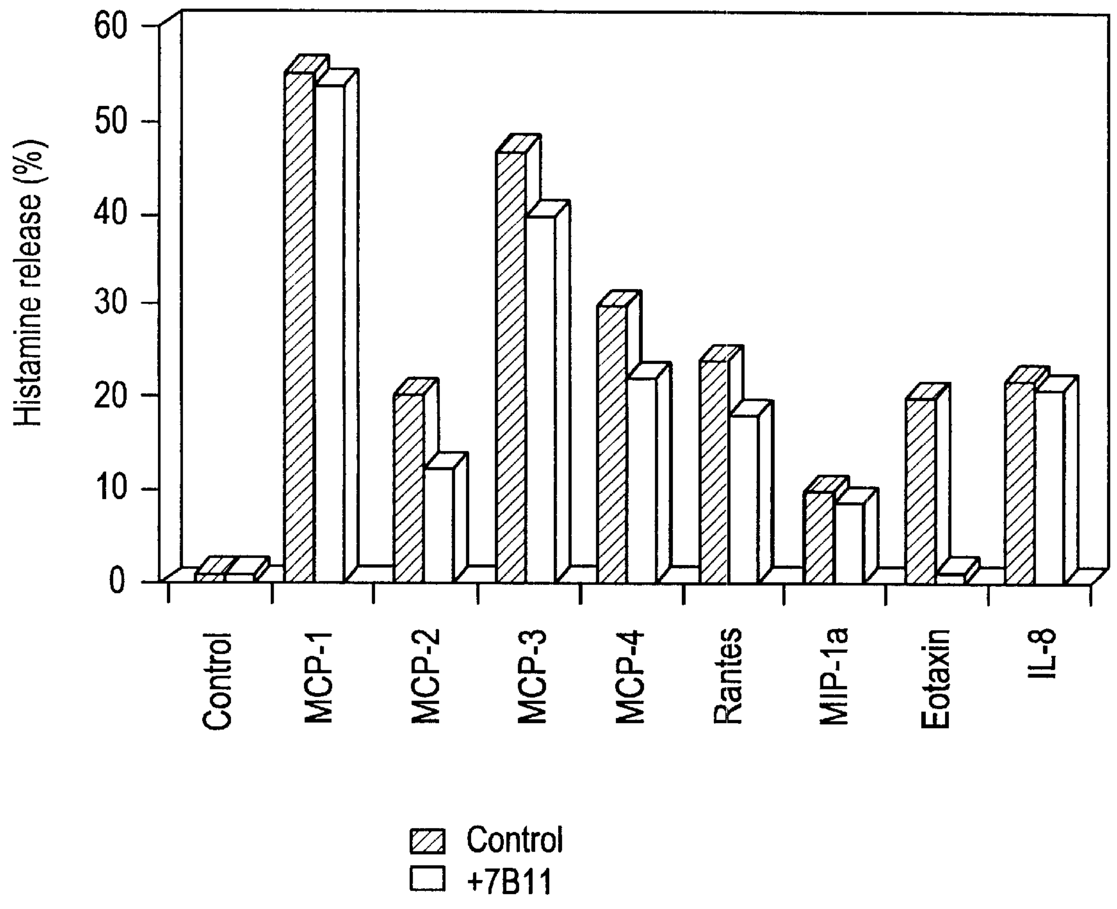
FIG. 29 is a histogram illustrating histamine release by human basophils in response to chemokines.

As shown in FIG. 29, basophils release histamine in response to chemokines, an histamine release can be blocked by MAb 7B11.

Chemotaxis

Chemokines were added to the lower wells of a 48 well chemotactic chamber (Neuro Probe, Cabin John, Md.). Cells were suspended in RPMI 1640, 20 mM Hepes and 1% PPL, pH 7.4 with or without anti-CCR3 (5 ug/ml) and placed into the top wells (50,000 cells per well). Migration across as polycarbonate filter (polyvinyl pyrrolidone free, 5 um pore size; Nucleopore Corp., Pleasanton, Calif.) was assessed after an incubation at 37° C. in 5% $CO_2$ for 50 min. Migrated cells were counted microscopically on the lower surface of the filter after staining with May-Gruenwald/Giemsa.

Figure 30A:
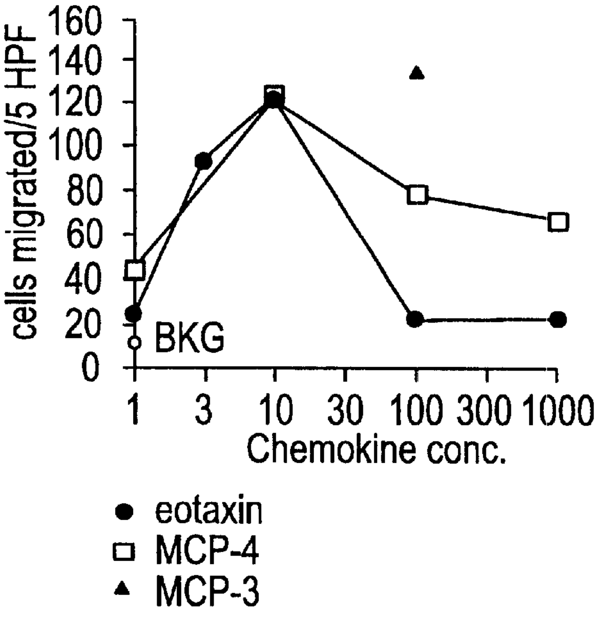
FIG. 30A is a graph illustrating that basophils chemotax in response to eotaxin and MCP-4.
Figure 30B:
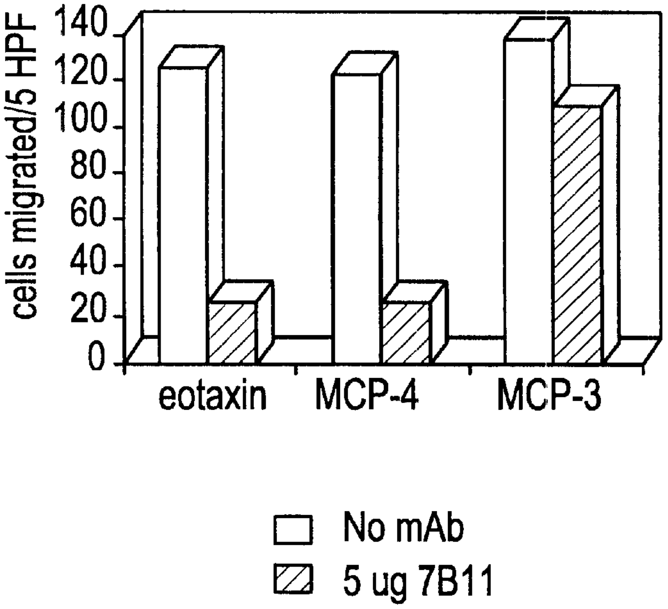
FIG. 30B is a histogram illustrating blockade of basophil chemotaxis in response to eotaxin and MCP-4 using anti-CCR3 mAb 7B11.

As shown in FIGS. 30A and 30B, basophils chemotax to eotaxin and MCP-4 and the response is blocked with anti-CCR3 mAb 7B11.

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A method of identifying an inhibitor of a human C—C chemokine receptor 3 comprising:

a) combining a compound to be tested, a host cell expressing a recombinant protein comprising a C—C chemokine receptor 3 polypeptide, and a ligand of said receptor under conditions suitable for binding of ligand to said polypeptide, wherein said polypeptide has at least 90% amino acid sequence identity with SEQ ID NO:2 or SEQ ID NO:6 and binds RANTES; and b) detecting or measuring the formation of a complex between said polypeptide and said ligand, wherein inhibition of complex formation by the compound is indicative that the compound is an inhibitor.

2. The method of claim 1, wherein said ligand is selected from the group consisting of RANTES and MCP-3.

3. The method of claim 1, wherein said ligand is labeled with a detectable label.

4. The method of claim 1, wherein the compound to be tested is an antibody or antibody fragment.

5. A method of identifying an inhibitor of a human C—C chemokine receptor 3 comprising:

a) combining a compound to be tested, a host cell expressing a recombinant protein comprising a C—C chemokine receptor 3, and a ligand of said receptor under conditions suitable for binding of ligand to said receptor, wherein the amino acid sequence of said receptor is encoded by SEQ ID NO:1; and b) detecting or measuring the formation of a complex between said receptor and said ligand, wherein inhibition of complex formation by the compound is indicative that the compound is an inhibitor.

6. The method of claim 1, wherein the amino acid sequence of said C—C chemokine receptor 3 polypeptide is selected from the group consisting of SEQ ID NO:2 and SEQ ID NO:6.

7. The method of claim 1, wherein said ligand is eotaxin.

8. The method of claim 1, wherein said ligand is selected from the group consisting of MCP-2 and MCP-4.

9. The method of claim 1, wherein the compound to be tested is an organic molecule.

10. The method of claim 5, wherein the compound to be tested is an organic molecule.

11. The method of claim 5, wherein said ligand is selected from the group consisting of RANTES and MCP-3.

12. The method of claim 5, wherein said ligand is eotaxin.

13. The method of claim 5, wherein said ligand is selected from the group consisting of MCP-2 and MCP-4.

14. The method of claim 5, wherein said ligand is labeled with a detectable label.

15. A method of identifying an inhibitor of a human C—C chemokine receptor 3 comprising:

a) combining a compound to be tested, a host cell expressing a recombinant protein comprising a C—C chemokine receptor 3 polypeptide, and a ligand of said receptor under conditions suitable for binding of ligand to said polypeptide, wherein said polypeptide has at least 90% amino acid sequence identity with SEQ ID NO:2 or SEQ ID NO:6 and binds MCP-3; and b) detecting or measuring the formation of a complex between said polypeptide and said ligand, wherein inhibition of complex formation by the compound is indicative that the compound is an inhibitor.

16. The method of claim 15, wherein the amino acid sequence of said C—C chemokine receptor 3 polypeptide is selected from the group consisting of SEQ ID NO:2 and SEQ ID NO:6.

17. The method of claim 15, wherein the compound to be tested is an organic molecule.

18. The method of claim 15, wherein the compound to be tested is an antibody or antibody fragment.

19. The method of claim 15, wherein said ligand is labeled with a detectable label.

20. The method of claim 15, wherein said ligand is selected from the group consisting of RANTES and MCP-3.

21. The method of claim 15, wherein said ligand is eotaxin.

22. The method of claim 15, wherein said ligand is selected from the group consisting of MCP-2 and MCP-4.

23. A method of identifying an inhibitor of a human C—C chemokine receptor 3 comprising:

a) combining a compound to be tested, a host cell expressing a recombinant protein comprising a C—C chemokine receptor 3 polypeptide, and a ligand of said receptor under conditions suitable for binding of ligand to said polypeptide, wherein said polypeptide has at least 90% amino acid sequence identity with SEQ ID NO:2 or SEQ ID NO:6 and binds eotaxin; and b) detecting or measuring the formation of a complex between said polypeptide and said ligand, wherein inhibition of complex formation by the compound is indicative that the compound is an inhibitor.

24. The method of claim 23, wherein the amino acid sequence of said C—C chemokine receptor 3 polypeptide is selected from the group consisting of SEQ ID NO:2 and SEQ ID NO:6.

25. The method of claim 23, wherein the compound to be tested is an organic molecule.

26. The method of claim 23, wherein the compound to be tested is an antibody or antibody fragment.

27. The method of claim 23, wherein said ligand is labeled with a detectable label.

28. The method of claim 23, wherein said ligand is selected from the group consisting of RANTES and MCP-3.

29. The method of claim 23, wherein said ligand is cotaxin.

30. The method of claim 23, wherein said ligand is selected from the group consisting of MCP-2 and MCP-4.

31. A method of identifying an inhibitor of a human C—C chemokine receptor 3 comprising:

a) combining a compound to be tested, a host cell expressing a recombinant protein comprising a C—C chemokine receptor 3 polypeptide, and a ligand of said receptor under conditions suitable for binding of ligand to said polypeptide, wherein said polypeptide has at least 90% amino acid sequence identity with SEQ ID NO:2 or SEQ ID NO:6 and binds MCP-2; and b) detecting or measuring the formation of a complex between said polypeptide and said ligand, wherein inhibition of complex formation by the compound is indicative that the compound is an inhibitor.

32. The method of claim 31, wherein the amino acid sequence of said C—C chemokine receptor 3 polypeptide is selected from the group consisting of SEQ ID NO:2 and SEQ ID NO:6.

33. The method of claim 31, wherein the compound to be tested is an organic molecule.

34. The method of claim 31, wherein the compound to be tested is an antibody or antibody fragment.

35. The method of claim 31, wherein said ligand is labeled with a detectable label.

36. The method of claim 31, wherein said ligand is selected from the group consisting of RANTES and MCP-3.

37. The method of claim 31, wherein said ligand is cotaxin.

38. The method of claim 31, wherein said ligand is selected from the group consisting of MCP-2 and MCP-4.

39. A method of identifying an inhibitor of a human C—C chemokine receptor 3 comprising:

a) combining a compound to be tested, a host cell expressing a recombinant protein comprising a C—C chemokine receptor 3 polypeptide, and a ligand of said receptor under conditions suitable for binding of ligand to said polypeptide, wherein said polypeptide has at least 90% amino acid sequence identity with SEQ ID NO:2 or SEQ ID NO:6 mid binds MCP-4; and b) detecting or measuring the formation of a complex between said polypeptide and said ligand, wherein inhibition of complex formation by the compound is indicative that the compound is an inhibitor.

40. The method of claim 39, wherein the amino acid sequence of said C—C chemokine receptor 3 polypeptide is selected from the group consisting of SEQ ID NO:2 and SEQ ID NO:6.

41. The method of claim 39, wherein the compound to be tested is an organic molecule.

42. The method of claim 39, wherein the compound to be tested is an antibody or antibody fragment.

43. The method of claim 39, wherein said ligand is labeled with a detectable label.

44. The method of claim 39, wherein said ligand is selected from the group consisting of RANTES and MCP-3.

45. The method of claim 39, wherein said ligand is cotaxin.

46. The method of claim 39, wherein said ligand is selected from the group consisting of MCP-2 and MCP-4.

47. A method of identifying an inhibitor of a human C—C chemokine receptor 3 comprising:

a) combining a compound to be tested, a host cell expressing a recombinant protein comprising a C—C chemokine receptor 3, and a ligand of said receptor under conditions suitable for binding of ligand to said receptor, wherein said C—C chemokine receptor 3 is encoded by a nucleic acid which hybridizes with a second nucleic acid selected from the group consisting of SEQ ID NO:1, SEQ ID NO:5, the complement of SEQ ID NO:1 and the compliment of SEQ ID NO:5, under hybridization conditions of 6×SSC containing 5×Denhardt's solution, 10% (w/v) dextran sulfate, 2% SDS and sheared salmon sperm DNA (100 $\mu$g/mL) at 65° C. and wash conditions of 0.2×SSC, 0.5% SDS at 65° C., and binds eotaxin; and b) detecting or measuring the formation of a complex between said receptor and said ligand, wherein inhibition of complex formation by the compound is indicative that the compound is an inhibitor.

48. The method of claim 47, wherein the compound to be tested is an organic molecule.

49. The method of claim 47, wherein the compound to be tested is an antibody or antibody fragment.

50. The method of claim 47, wherein said ligand is labeled with a detectable label.

51. The method of claim 47, wherein said ligand is selected from the group consisting of RANTES and MCP-3.

52. The method of claim 47, wherein said ligand is eotaxin.

53. The method of claim 47, wherein said ligand is selected from the group consisting of MCP-2 and MCP-4.

54. A method of identifying an inhibitor of a human C—C chemokine receptor 3 comprising:

a) combining a compound to be tested, a host cell expressing a recombinant protein comprising a C—C chemokine receptor 3, and a ligand of said receptor under conditions suitable for binding of ligand to said receptor, wherein the amino acid sequence of said receptor is encoded by SEQ ID NO:5 and said receptor binds RANTES; and b) detecting or measuring the formation of a complex between said receptor and said ligand, wherein inhibition of complex formation by the compound is indicative that the compound is an inhibitor.

55. The method of claim 54, wherein the compound to be tested is an organic molecule.

56. The method of claim 54, wherein said ligand is labeled with a detectable label.

57. The method of claim 54, wherein said ligand is selected from the group consisting of RANTES and MCP-3.

58. The method of claim 54, wherein said ligand is eotaxin.

59. The method of claim 54, wherein said ligand is selected from the group consisting of MCP-2 and MCP-4.

60. A method of identifying an inhibitor of a human C—C chemokine receptor 3 comprising:

a) combining a compound to be tested, a host cell expressing a recombinant protein comprising a C—C chemokine receptor 3, and a ligand of said receptor under conditions suitable for binding of ligand to said receptor, wherein the amino acid sequence of said receptor is encoded by SEQ ID NO:5 and said receptor binds MCP-3; and b) detecting or measuring the formation of a complex between said receptor and said ligand, wherein inhibition of complex formation by the compound is indicative that the compound is an inhibitor.

61. The method of claim 60, wherein the compound to be tested is an organic molecule.

62. The method of claim 60, wherein said ligand is labeled with a detectable label.

63. The method of claim 60, wherein said ligand is selected from the group consisting of RANTES and MCP-3.

64. The method of claim 60, wherein said ligand is eotaxin.

65. The method of claim 60, wherein said ligand is selected from the group consisting of MCP-2 and MCP-4.

66. A method of identifying an inhibitor of a human C—C chemokine receptor 3 comprising:

a) combining a compound to be tested, a host cell expressing a recombinant protein comprising a C—C chemokine receptor 3, and a ligand of said receptor under conditions suitable for binding of ligand to said receptor, wherein the amino acid sequence of said receptor is encoded by SEQ ID NO:5 and said receptor binds eotaxin; and b) detecting or measuring the formation of a complex between said receptor and said ligand, wherein inhibition of complex formation by the compound is indicative that the compound is an inhibitor.

67. The method of claim 66, wherein the compound to be tested is an organic molecule.

68. The method of claim 66, wherein said ligand is labeled with a detectable label.

69. The method of claim 66, wherein said ligand is selected from the group consisting of RANTES and MCP-3.

70. The method of claim 66, wherein said ligand is cotaxin.

71. The method of claim 66, wherein said ligand is selected from the group consisting of MCP-2 and MCP-4.

72. A method of identifying an inhibitor of a human C—C chemokine receptor 3 comprising:

a) combining a compound to be tested, a host cell expressing a recombinant protein comprising a C—C chemokine receptor 3, and a ligand of said receptor under conditions suitable for binding of ligand to said receptor, wherein the amino acid sequence of said receptor is encoded by SEQ ID NO:5 and said receptor binds MCP-2; and b) detecting or measuring the formation of a complex between said receptor and said ligand, wherein inhibition of complex formation by the compound is indicative that the compound is an inhibitor.

73. The method of claim 72, wherein the compound to be tested is an organic molecule.

74. The method of claim 72, wherein said ligand is labeled with a detectable label.

75. The method of claim 72, wherein said ligand is selected from the group consisting of RANTES and MCP-3.

76. The method of claim 72, wherein said ligand is eotaxin.

77. The method of claim 72, wherein said ligand is selected from the group consisting of MCP-2 and MCP-4.

78. A method of identifying an inhibitor of a human C—C chemokine receptor 3 comprising:

a) combining a compound to be tested, a host cell expressing a recombinant protein comprising a C—C chemokine receptor 3, and a ligand of said receptor under conditions suitable for binding of ligand to said receptor, wherein the amino acid sequence of said receptor is encoded by SEQ ID NO:5 and said receptor binds MCP-4; and b) detecting or measuring the formation of a complex between said receptor and said ligand, wherein inhibition of complex formation by the compound is indicative that the compound is an inhibitor.

79. The method of claim 78, wherein the compound to be tested is an organic molecule.

80. The method of claim 78, wherein said ligand is labeled with a detectable label.

81. The method of claim 78, wherein said ligand is selected from the group consisting of RANTES and MCP-3.

82. The method of claim 78, wherein said ligand is eotaxin.

83. The method of claim 78, wherein said ligand is selected from the group consisting of MCP-2 and MCP.

* * * * *

UNITED STATES PATENT AND TRADEMARK OFFICE

CERTIFICATE OF CORRECTION

PATENT NO. : 6,537,764 B1 Page 1 of 1
DATED : March 25, 2003
INVENTOR(S) : Craig J. Gerard et al.

It is certified that error appears in the above-identified patent and that said Letters Patent is hereby corrected as shown below:

Column 86,
Line 67, delete "cotaxin" and insert -- eotaxin --.

Column 87,
Lines 30 and 60, delete "cotaxin" and insert -- eotaxin --;
Line 42, delete "mid" and insert -- and --;

Column 88,
Line 8, delete "compliment" and insert -- complement --.

Column 89,
Line 32, delete "cotaxin" and insert -- eotaxin --.

Column 90,
Line 41, delete "MCP" and insert -- MCP-4 --.

Signed and Sealed this

Ninth Day of September, 2003

JAMES E. ROGAN
*Director of the United States Patent and Trademark Office*

```
SEQUENCE LISTING

(1) GENERAL INFORMATION:

   (iii) NUMBER OF SEQUENCES: 18

(2) INFORMATION FOR SEQ ID NO:1:

     (i) SEQUENCE CHARACTERISTICS:
          (A) LENGTH: 1689 base pairs
          (B) TYPE: nucleic acid
          (C) STRANDEDNESS: double
          (D) TOPOLOGY: linear

    (ii) MOLECULE TYPE: DNA (genomic)

    (xi) SEQUENCE DESCRIPTION: SEQ ID NO:1:

AATCCTTTTC CTGGCACCTC TGATATCCTT TTGAAATTCA TGTTAAAGAA TCCCTAGGCT      60
```

-continued

```
GCTATCACAT GTGGCATCTT TGTTGAGTAC ATGAATAAAT CAACTGGTGT GTTTTACGAA    120

GGATGATTAT GCTTCATTGT GGGATTGTAT TTTTCTTCTT CTATCACAGG GAGAAGTGAA    180

ATGACAACCT CACTAGATAC AGTTGAGACC TTTGGTACCA CATCCTACTA TGATGACGTG    240

GGCCTGCTCT GTGAAAAAGC TGATACCAGA GCACTGATGG CCCAGTTTGT GCCCCCGCTG    300

TACTCCCTGG TGTTCACTGT GGGCCTCTTG GGCAATGTGG TGGTGGTGAT GATCCTCATA    360

AAATACAGGA GGCTCCGAAT TATGACCAAC ATCTACCTGC TCAACCTGGC CATTTCGGAC    420

CTGCTCTTCC TCGTCACCCT TCCATTCTGG ATCCACTATG TCAGGGGGCA TAACTGGGTT    480

TTTGGCCATG GCATGTGTAA GCTCCTCTCA GGGTTTTATC ACACAGGCTT GTACAGCGAG    540

ATCTTTTTCA TAATCCTGCT GACAATCGAC AGGTACCTGG CCATTGTCCA TGCTGTGTTT    600

GCCCTTCGAG CCCGGACTGT CACTTTTGGT GTCATCACCA GCATCGTCAC CTGGGGCCTG    660

GCAGTGCTAG CAGCTCTTCC TGAATTTATC TTCTATGAGA CTGAAGAGTT GTTTGAAGAG    720

ACTCTTTGCA GTGCTCTTTA CCCAGAGGAT ACAGTATATA GCTGGAGGCA TTTCCACACT    780

CTGAGAATGA CCATCTTCTG TCTCGTTCTC CCTCTGCTCG TTATGGCCAT CTGCTACACA    840

GGAATCATCA AAACGCTGCT GAGGTGCCCC AGTAAAAAAA AGTACAAGGC CATCCGGCTC    900

ATTTTTGTCA TCATGGCGGT GTTTTTCATT TTCTGGACAC CCTACAATGT GGCTATCCTT    960

CTCTCTTCCT ATCAATCCAT CTTATTTGGA AATGACTGTG AGCGGACGAA GCATCTGGAC   1020

CTGGTCATGC TGGTGACAGA GGTGATCGCC TACTCCCACT GCTGCATGAA CCCGGTGATC   1080

TACGCCTTTG TTGGAGAGAG GTTCCGGAAG TACCTGCGCC ACTTCTTCCA CAGGCACTTG   1140

CTCATGCACC TGGGCAGATA CATCCCATTC CTTCCTAGTG AGAAGCTGGA AAGAACCAGC   1200

TCTGTCTCTC CATCCACAGC AGAGCCGGAA CTCTCTATTG TGTTTTAGGT AGATGCAGAA   1260

AATTGCCTAA AGAGGAAGGA CCAAGGAGAT NAAGCAAACA CATTAAGCCT TCCACACTCA   1320

CCTCTAAAAC AGTCCTTCAA ACCTTCCAGT GCAACACTGA AGCTCTTAAG ACACTGAAAT   1380

ATACACACAG CAGTAGCAGT AGATGCATGT ACCCTAAGGT CATTACCACA GGCCAGGGCT   1440

GGGCAGCGTA CTCATCATCA ACCTAAAAAG CAGAGCTTTG CTTCTCTCTC TAAAATGAGT   1500

TACCTATATT TTAATGCACC TGAATGTTAG ATAGTTACTA TATGCCGCTA CAAAAAGGTA   1560

AAACTTTTTA TATTTTATAC ATTAACTTCA GCCAGCTATT ATATAAATAA AACATTTTCA   1620

CACAATACAA TAAGTTAACT ATTTTATTTT CTAATGTGCC TAGTTCTTTC CCTGCTTAAT   1680

GAAAAGCTT                                                           1689
```

(2) INFORMATION FOR SEQ ID NO:2:

(i) SEQUENCE CHARACTERISTICS:
(A) LENGTH: 355 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:2:

```
Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Phe Gly
        35                  40                  45

Leu Leu Gly Asn Val Val Val Val Met Ile Leu Ile Lys Tyr Arg Arg
```

-continued

```
    50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Thr Lys His Leu Asp Leu Val Met Leu Val Thr Glu Val
        275                 280                 285

Ile Ala Tyr Ser His Cys Cys Met Asn Pro Val Ile Tyr Ala Phe Val
    290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355
```

(2) INFORMATION FOR SEQ ID NO:3:

(i) SEQUENCE CHARACTERISTICS:
(A) LENGTH: 1193 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 92..1156

(xi) SEQUENCE DESCRIPTION: SEQ ID NO:3:

```
TTGTGCTTAT CCGGGCAAGA ACTTATCGAA ATACAATAGA AGACCCACGC GTCCGGTTTT      60

TACTTAGAAG AGATTTTCAG GGAGAAGTGA A ATG ACA ACC TCA CTA GAT ACA       112
```

-continued

```
                                   Met Thr Thr Ser Leu Asp Thr
                                    1               5

GTT GAG ACC TTT GGT ACC ACA TCC TAC TAT GAT GAC GTG GGC CTG CTC       160
Val Glu Thr Phe Gly Thr Thr Ser Tyr Tyr Asp Asp Val Gly Leu Leu
        10                  15                  20

TGT GAA AAA GCT GAT ACC AGA GCA CTG ATG GCC CAG TTT GTG CCC CCG       208
Cys Glu Lys Ala Asp Thr Arg Ala Leu Met Ala Gln Phe Val Pro Pro
    25                  30                  35

CTG TAC TCC CTG GTG TTC ACT GTG GGC CTC TTG GGC AAT GTG GTG GTG       256
Leu Tyr Ser Leu Val Phe Thr Val Gly Leu Leu Gly Asn Val Val Val
 40                  45                  50                  55

GTG ATG ATC CTC ATA AAA TAC AGG AGG CTC CGA ATT ATG ACC AAC ATC       304
Val Met Ile Leu Ile Lys Tyr Arg Arg Leu Arg Ile Met Thr Asn Ile
                60                  65                  70

TAC CTG CTC AAC CTG GCC ATT TCG GAC CTG CTC TTC CTC GTC ACC CTT       352
Tyr Leu Leu Asn Leu Ala Ile Ser Asp Leu Leu Phe Leu Val Thr Leu
            75                  80                  85

CCA TTC TGG ATC CAC TAT GTC AGG GGG CAT AAC TGG GTT TTT GGC CAT       400
Pro Phe Trp Ile His Tyr Val Arg Gly His Asn Trp Val Phe Gly His
        90                  95                 100

GGC ATG TGT AAG CTC CTC TCA GGG TTT TAT CAC ACA GGC TTG TAC AGC       448
Gly Met Cys Lys Leu Leu Ser Gly Phe Tyr His Thr Gly Leu Tyr Ser
    105                 110                 115

GAG ATC TTT TTC ATA ATC CTG CTG ACA ATC GAC AGG TAC CTG GCC ATT       496
Glu Ile Phe Phe Ile Ile Leu Leu Thr Ile Asp Arg Tyr Leu Ala Ile
120                 125                 130                 135

GTC CAT GCT GTG TTT GCC CTT CGA GCC CGG ACT GTC ACT TTT GGT GTC       544
Val His Ala Val Phe Ala Leu Arg Ala Arg Thr Val Thr Phe Gly Val
                140                 145                 150

ATC ACC AGC ATC GTC ACC TGG GGC CTG GCA GTG CTA GCA GCT CTT CCT       592
Ile Thr Ser Ile Val Thr Trp Gly Leu Ala Val Leu Ala Ala Leu Pro
            155                 160                 165

GAA TTT ATC TTC TAT GAG ACT GAA GAG TTG TTT GAA GAG ACT CTT TGC       640
Glu Phe Ile Phe Tyr Glu Thr Glu Glu Leu Phe Glu Glu Thr Leu Cys
        170                 175                 180

AGT GCT CTT TAC CCA GAG GAT ACA GTA TAT AGC TGG AGG CAT TTC CAC       688
Ser Ala Leu Tyr Pro Glu Asp Thr Val Tyr Ser Trp Arg His Phe His
    185                 190                 195

ACT CTG AGA ATG ACC ATC TTC TGT CTC GTT CTC CCT CTG CTC GTT ATG       736
Thr Leu Arg Met Thr Ile Phe Cys Leu Val Leu Pro Leu Leu Val Met
200                 205                 210                 215

GCC ATC TGC TAC ACA GGA ATC ATC AAA ACG CTG CTG AGG TGC CCC AGT       784
Ala Ile Cys Tyr Thr Gly Ile Ile Lys Thr Leu Leu Arg Cys Pro Ser
                220                 225                 230

AAA AAA AAG TAC AAG GCC ATC CGG CTC ATT TTT GTC ATC ATG GCG GTG       832
Lys Lys Lys Tyr Lys Ala Ile Arg Leu Ile Phe Val Ile Met Ala Val
            235                 240                 245

TTT TTC ATT TTC TGG ACA CCC TAC AAT GTG GCT ATC CTT CTC TCT TCC       880
Phe Phe Ile Phe Trp Thr Pro Tyr Asn Val Ala Ile Leu Leu Ser Ser
        250                 255                 260

TAT CAA TCC ATC TTA TTT GGA AAT GAC TGT GAG CGG AGC AAG CAT CTG       928
Tyr Gln Ser Ile Leu Phe Gly Asn Asp Cys Glu Arg Ser Lys His Leu
    265                 270                 275

GAC CTG GTC ATG CTG GTG ACA GAG GTG ATC GCC TAC TCC CAC TGC TGC       976
Asp Leu Val Met Leu Val Thr Glu Val Ile Ala Tyr Ser His Cys Cys
280                 285                 290                 295

ATG AAC CCG GTG ATC TAC GCC TTT GTT GGA GAG AGG TTC CGG AAG TAC      1024
Met Asn Pro Val Ile Tyr Ala Phe Val Gly Glu Arg Phe Arg Lys Tyr
                300                 305                 310
```

-continued

```
CTG CGC CAC TTC TTC CAC AGG CAC TTG CTC ATG CAC CTG GGC AGA TAC      1072
Leu Arg His Phe Phe His Arg His Leu Leu Met His Leu Gly Arg Tyr
            315                 320                 325

ATC CCA TTC CTT CCT AGT GAG AAG CTG GAA AGA ACC AGC TCT GTC TCT      1120
Ile Pro Phe Leu Pro Ser Glu Lys Leu Glu Arg Thr Ser Ser Val Ser
        330                 335                 340

CCA TCC ACA GCA GAG CCG GAA CTC TCT ATT GTG TTT TAGGTAGATG           1166
Pro Ser Thr Ala Glu Pro Glu Leu Ser Ile Val Phe
    345                 350                 355

CAGAAAATTG CCTAAAGAGG AAGGACC                                        1193
```

(2) INFORMATION FOR SEQ ID NO:4:

(i) SEQUENCE CHARACTERISTICS:
(A) LENGTH: 355 amino acids
(B) TYPE: amino acid
(D) TOPOLOGY: linear (ii) MOLECULE TYPE: protein (xi) SEQUENCE DESCRIPTION: SEQ ID NO:4:

```
Met Thr Thr Ser Leu Asp Thr Val Glu Thr Phe Gly Thr Thr Ser Tyr
  1               5                  10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Val Met Ile Leu Ile Lys Tyr Arg Arg
     50                  55                  60

Leu Arg Ile Met Thr Asn Ile Tyr Leu Leu Asn Leu Ala Ile Ser Asp
 65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
        275                 280                 285
```

-continued

Ile Ala Tyr Ser His Cys Cys Met Asn Pro Val Ile Tyr Ala Phe Val
    290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

(2) INFORMATION FOR SEQ ID NO:5:

(i) SEQUENCE CHARACTERISTICS:
(A) LENGTH: 1116 base pairs
(B) TYPE: nucleic acid
(C) STRANDEDNESS: double
(D) TOPOLOGY: linear (xi) SEQUENCE DESCRIPTION: SEQ ID NO:5:

CAGGGAGAAG TGAAATGACA ACCTCACTAG ATACAGTTGA GACCTTTGGT ACCACATCCT 60

ACTATGATGA CGTGGGCCTG CTCTGTGAAA AAGCTGATAC CAGAGCACTG ATGGCCCAGT 120

TTGTGCCCCC GCTGTACTCC CTGGTGTTCA CTGTGGGCCT CTTGGGCAAT GTGGTGGTGG 180

TGATGATCCT CATAAAATAC AGGAGGCTCC GAATTATGAC CAACATCTAC CTGCTCAACC 240

TGGCCATTTC GGACCTGCTC TTCCTCGTCA CCCTTCCATT CTGGATCCAC TATGTCAGGG 300

GGCATAACTG GGTTTTTGGC CATGGCATGT GTAAGCTCCT CTCAGGGTTT TATCACACAG 360

GCTTGTACAG CGAGATCTTT TTCATAATCC TGCTGACAAT CGACAGGTAC CTGGCCATTG 420

TCCATGCTGT GTTTGCCCTT CGAGCCCGGA CTGTCACTTT TGGTGTCATC ACCAGCATCG 480

TCACCTGGGG CCTGGCAGTG CTAGCAGCTC TTCCTGAATT TATCTTCTAT GAGACTGAAG 540

AGTTGTTTGA AGAGACTMTT TGCAGTGCTC TTTACCCAGA GGATACAGTA TATAGCTGGA 600

GSSATTTCCA CACTCTGAGA ATGACCATCT TCTGTCTCGT TCTCCCTCTG CTCGTTATGG 660

CCATCTGCTA CACAGGAATC ATCAAAACGC TGCTGAGGTG CCCCAGTAAA AAAAAGTACA 720

AGGCCATCCG GCTCATTTTT GTCATCATGG CGGTGTTTTT CATTTTCTGG ACACCCTACA 780

ATGTGGCTAT CCTTCTCTCT TSCYWWYMAW YCATCTTATT TGGAAATGAC TGTGAGCGGM 840

MGARSMWYYK GGACCTGGTC ATGCTGGTGA CAGAGGTGAT CGCCTACTCC CACTGCTGCA 900

TGAACCCGGT GATCTACGCC TTTGTTGGAG AGAGGTTCCG GAAGTACCTG CGCCACTTST 960

TCCACAGGCA CTTGCTCATG CACCTGGGCA GATACATCCC ATTCCTTCCT AGTGAGAAGC 1020

TGGAAAGAAC CAGCTCTGTC TCTCCATCCA CAGCAGAGCC GGAACTCTCT ATTGTGTTTT 1080

AGGTAGATGC AGAAAATTGC CTAAAGAGGA AGGACC 1116

(2) INFORMATION FOR SEQ ID NO:6:

(i) SEQUENCE CHARACTERISTICS:
(A) LENGTH: 355 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:6:

Met Thr Thr Ser Leu Asp Thr Val Glu Thr Phe Gly Thr Thr Ser Tyr

-continued

```
1               5                   10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Val Met Ile Leu Ile Lys Tyr Arg Arg
    50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Xaa Cys Ser Ala Leu Tyr Pro Glu Asp Thr Val
            180                 185                 190

Tyr Ser Trp Xaa Xaa Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Xaa Xaa Xaa Xaa Ile Leu Phe Gly Asn Asp
            260                 265                 270

Cys Glu Arg Xaa Xaa Xaa Xaa Asp Leu Val Met Leu Val Thr Glu Val
        275                 280                 285

Ile Ala Tyr Ser His Cys Cys Met Asn Pro Val Ile Tyr Ala Phe Val
    290                 295                 300

Gly Glu Arg Phe Arg Lys Tyr Leu Arg His Xaa Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355
```

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: single
(D) TOPOLOGY: linear (ix) FEATURE:
(A) NAME/KEY: modified_base -continued (B) LOCATION: 19
(D) OTHER INFORMATION: /mod_base= i (ix) FEATURE:
(A) NAME/KEY: modified_base
(B) LOCATION: 24
(D) OTHER INFORMATION: /mod_base= i (xi) SEQUENCE DESCRIPTION: SEQ ID NO:7:

TACCTGCTSA ACCTGGCCNT GGCNG 25

(2) INFORMATION FOR SEQ ID NO:8:

(i) SEQUENCE CHARACTERISTICS:
(A) LENGTH: 25 base pairs
(B) TYPE: nucleic acid
(C) STRANDEDNESS: single
(D) TOPOLOGY: linear (ix) FEATURE:
(A) NAME/KEY: modified_base
(B) LOCATION: 9
(D) OTHER INFORMATION: /mod_base= i (ix) FEATURE:
(A) NAME/KEY: modified_base
(B) LOCATION: 14
(D) OTHER INFORMATION: /mod_base= i (xi) SEQUENCE DESCRIPTION: SEQ ID NO:8:

ACCTGGCCNT GGCNGACCTM CTCTT 25

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(A) NAME/KEY: modified_base
(B) LOCATION: 18
(D) OTHER INFORMATION: /mod_base= i (xi) SEQUENCE DESCRIPTION: SEQ ID NO:9:

GACCGYTACC TGGCCATNGT CCAYGCC 27

(2) INFORMATION FOR SEQ ID NO:10:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(A) NAME/KEY: modified_base
(B) LOCATION: 10
(D) OTHER INFORMATION: /mod_base= i (xi) SEQUENCE DESCRIPTION: SEQ ID NO:10:

GGCRTGGACN ATGGCCAGGT ARCGGTC 27

(2) INFORMATION FOR SEQ ID NO:11:

(i) SEQUENCE CHARACTERISTICS:
(A) LENGTH: 27 base pairs
(B) TYPE: nucleic acid
(C) STRANDEDNESS: single
(D) TOPOLOGY: linear -continued (ix) FEATURE:
(A) NAME/KEY: modified_base
(B) LOCATION: 1
(D) OTHER INFORMATION: /mod_base= i (ix) FEATURE:
(A) NAME/KEY: modified_base
(B) LOCATION: 6
(D) OTHER INFORMATION: /mod_base= i (ix) FEATURE:
(A) NAME/KEY: modified_base
(B) LOCATION: 16
(D) OTHER INFORMATION: /mod_base= i (ix) FEATURE:
(A) NAME/KEY: modified_base
(B) LOCATION: 18
(D) OTHER INFORMATION: /mod_base= i (xi) SEQUENCE DESCRIPTION: SEQ ID NO:11:

NACCANRTTG TAGGGNRNCC ARMARAG 27

(2) INFORMATION FOR SEQ ID NO:12:

(i) SEQUENCE CHARACTERISTICS:
(A) LENGTH: 28 base pairs
(B) TYPE: nucleic acid
(C) STRANDEDNESS: single
(D) TOPOLOGY: linear (ix) FEATURE:
(A) NAME/KEY: modified_base
(B) LOCATION: 8
(D) OTHER INFORMATION: /mod_base= i (ix) FEATURE:
(A) NAME/KEY: modified_base
(B) LOCATION: 10
(D) OTHER INFORMATION: /mod_base= i (ix) FEATURE:
(A) NAME/KEY: modified_base
(B) LOCATION: 23
(D) OTHER INFORMATION: /mod_base= i (xi) SEQUENCE DESCRIPTION: SEQ ID NO:12:

TGTAGGGNRN CCARMARAGR AGNARGAA 28

(2) INFORMATION FOR SEQ ID NO:13:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(A) NAME/KEY: modified_base
(B) LOCATION: 12
(D) OTHER INFORMATION: /mod_base= i (ix) FEATURE:
(A) NAME/KEY: modified_base
(B) LOCATION: 15
(D) OTHER INFORMATION: /mod_base= i (ix) FEATURE:
(A) NAME/KEY: modified_base
(B) LOCATION: 16
(D) OTHER INFORMATION: /mod_base= i (xi) SEQUENCE DESCRIPTION: SEQ ID NO:13:

-continued

```
GAAGGCGTAG ANSANNGGGT TGASGCA                                     27


(2) INFORMATION FOR SEQ ID NO:14:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ix) FEATURE:
          (A) NAME/KEY: modified_base
          (B) LOCATION: 4
          (D) OTHER INFORMATION: /mod_base= i

    (ix) FEATURE:
          (A) NAME/KEY: modified_base
          (B) LOCATION: 7
          (D) OTHER INFORMATION: /mod_base= i

    (ix) FEATURE:
          (A) NAME/KEY: modified_base
          (B) LOCATION: 8
          (D) OTHER INFORMATION: /mod_base= i

    (xi) SEQUENCE DESCRIPTION: SEQ ID NO:14:

AGANSANNGG GTTGASGCAG CWGTG                                       25


(2) INFORMATION FOR SEQ ID NO:15:

     (i) SEQUENCE CHARACTERISTICS:
          (A) LENGTH: 48 base pairs
          (B) TYPE: nucleic acid
          (C) STRANDEDNESS: double
          (D) TOPOLOGY: linear

    (ix) FEATURE:
          (A) NAME/KEY: CDS
          (B) LOCATION: 16..48

    (xi) SEQUENCE DESCRIPTION: SEQ ID NO:15:

AAGCTTCCAG CAGCC ATG GAC TAC AAG GAC GAC GAT GAC AAA GAA TTC      48
                 Met Asp Tyr Lys Asp Asp Asp Asp Lys Glu Phe
                   1               5                  10


(2) INFORMATION FOR SEQ ID NO:16:

     (i) SEQUENCE CHARACTERISTICS:
          (A) LENGTH: 11 amino acids
          (B) TYPE: amino acid
          (D) TOPOLOGY: linear

    (ii) MOLECULE TYPE: protein

    (xi) SEQUENCE DESCRIPTION: SEQ ID NO:16:

Met Asp Tyr Lys Asp Asp Asp Asp Lys Glu Phe
  1               5                  10


(2) INFORMATION FOR SEQ ID NO:17:

     (i) SEQUENCE CHARACTERISTICS:
          (A) LENGTH: 27 base pairs
          (B) TYPE: nucleic acid
          (C) STRANDEDNESS: single
          (D) TOPOLOGY: linear

    (xi) SEQUENCE DESCRIPTION: SEQ ID NO:17:

TTAAGAATTC ACAACCTCAC TAGATAC                                     27


(2) INFORMATION FOR SEQ ID NO:18:
```

-continued

```
    (i) SEQUENCE CHARACTERISTICS:
         (A) LENGTH: 18 base pairs
         (B) TYPE: nucleic acid
         (C) STRANDEDNESS: single
         (D) TOPOLOGY: linear

   (xi) SEQUENCE DESCRIPTION: SEQ ID NO:18:

CATAGTGGAT CCAGAATG                                                   18
```